(12) United States Patent
Shi et al.

(10) Patent No.: US 8,263,608 B2
(45) Date of Patent: Sep. 11, 2012

(54) MELANOCORTIN RECEPTOR-SPECIFIC SPIRO-PIPERIDINE COMPOUNDS

(75) Inventors: Yi-Qun Shi, East Brunswick, NJ (US); John H. Dodd, Flemington, NJ (US); Elizabeth G. Rowley, Kendal Park, NJ (US); Gary L. Olson, Mountainside, NJ (US); Axel Metzger, East Windsor, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

(21) Appl. No.: 13/074,070

(22) Filed: Mar. 29, 2011

(65) Prior Publication Data
US 2011/0178080 A1    Jul. 21, 2011

Related U.S. Application Data

(63) Continuation of application No. PCT/US2009/058708, filed on Sep. 29, 2009.

(60) Provisional application No. 61/101,089, filed on Sep. 29, 2008.

(51) Int. Cl.
*A61K 31/415* (2006.01)
*A61K 31/445* (2006.01)
*A61K 31/454* (2006.01)
*A61K 31/4545* (2006.01)
*C07D 221/00* (2006.01)
*C07D 233/00* (2006.01)

(52) U.S. Cl. ............. 514/278; 514/323; 546/15; 546/17; 546/18; 546/184; 546/192; 548/300.1

(58) Field of Classification Search .................. 514/323; 546/184, 192; 548/300.1
See application file for complete search history.

(56) References Cited

U.S. PATENT DOCUMENTS

| | | | |
|---|---|---|---|
| 6,043,366 A | 3/2000 | Adam et al. | |
| 6,713,487 B2 * | 3/2004 | Yu et al. | 514/278 |
| 6,979,691 B2 * | 12/2005 | Yu et al. | 514/322 |
| 7,053,101 B2 | 5/2006 | Jordan et al. | |
| 7,067,525 B2 * | 6/2006 | Yu et al. | 514/278 |
| 7,329,673 B2 | 2/2008 | Guo et al. | |
| 7,402,564 B1 | 7/2008 | Schteingart et al. | |
| 2008/0249122 A1 | 10/2008 | Bignan et al. | |

OTHER PUBLICATIONS

Patani et al., Chem Rev, 1996, vol. 96 (8), especially p. 3149.*
PCT International Search Report (PCT/ISA/210) and PCT Written Opinion of International Searching Authority in International application No. PCT/US09/58708, as mailed on Nov. 16, 2009.

* cited by examiner

*Primary Examiner* — Susannah Chung
(74) *Attorney, Agent, or Firm* — Stephen A. Slusher

(57) ABSTRACT

Melanocortin receptor-specific compounds of formula I below:

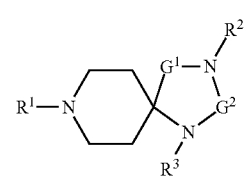

wherein the variables are as defined in the specification, and enantiomers, diastereomers and pharmaceutically acceptable salts thereof. Compounds disclosed herein bind to one or more melanocortin receptors and may be an agonist, a partial agonist, an antagonist, an inverse agonist or an antagonist of an inverse agonist as to one or more melanocortin receptors, and may be employed for treatment of one or more melanocortin receptor-associated conditions or disorders.

15 Claims, No Drawings

MELANOCORTIN RECEPTOR-SPECIFIC SPIRO-PIPERIDINE COMPOUNDS

CROSS-REFERENCE TO RELATED APPLICATIONS

This Application is a continuation application of International Application Number PCT/US2009/058708, entitled "Melanocortin Receptor-Specific Spiro-Piperidine Compounds", filed on Sep. 29, 2009, which in turn claims priority to and the benefit of the filing of U.S. Provisional Patent Application Ser. No. 61/101,089, entitled "New Compounds", filed on Sep. 29, 2008, and the specification thereof of each is incorporated herein by reference.

FIELD OF THE INVENTION

The present invention relates to spiro-piperidine compounds that bind to one or more melanocortin receptors and are agonists, antagonists, mixed agonist-antagonists, inverse agonist or antagonists of inverse agonists with respect to one or more melanocortin receptors, and use thereof for the treatment of metabolic, immune, inflammation-related and other melanocortin receptor-mediated disorders.

BACKGROUND

The listing or discussion of a prior-published document in this specification should not necessarily be taken as an acknowledgement that the document is part of the state of the art or is common general knowledge.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R), expressed primarily in cells in the hypothalamus, midbrain and brainstem, and melanocortin-5 receptors (MC5-R), expressed in a wide distribution of tissues.

In general, compounds specific for MC1-R are believed to be useful for dermatologic applications, treatment of certain cancers such as melanoma, and regulation of inflammatory processes, among other indications. Compounds specific for MC3-R or MC4-R are believed to be useful in regulation of energy homeostasis, including use as agents for attenuating food intake and body weight gain, for use in treatment of cachexia, as a weight gain aid, or alternatively for treatment of obesity, and generally for food intake and metabolism-related purposes. Compounds specific for MC3-R and MC4-R can further be used as agents for treatment of sexual dysfunction, including male erectile dysfunction and female sexual dysfunction. Such compounds may also have application in treatment of drug addiction, including alcohol abuse or addiction, as anxiolytic agents, and for treatment of depression. MC1-R agonists can be used as tanning agents to increase melanin production in the skin, acting as chemo-preventive agents against harmful effects of UV solar radiation. Compounds specific for MC1-R or MC3-R or both may be useful in regulation of inflammatory processes.

There is a significant need for compounds with high specificity for discrete melanocortin receptors, as well as for compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

SUMMARY OF THE INVENTION

In one embodiment, the invention provides a compound of formula I:

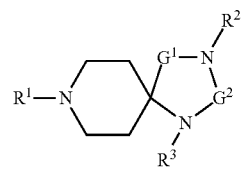

or an enantiomer, stereoisomer or diastereoisomer thereof, or a pharmaceutically acceptable salt thereof, wherein:
$G^1$ and $G^2$ independently represent $(CH_2)_{1-2}$ or $C(O)$;
$R^1$ represents
H,
$R^x$,
$X^1$—$R^5$ or
$N(H)R^6$;
$R^5$ represents
$R^x$,
$OR^{7a}$,
$N(R^{7b})R^{7c}$ or
a structural fragment of the formula

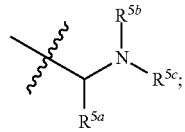

$R^{5b}$ and $R^{5c}$ independently represent H or $R^x$,
or $R^{5b}$ and $R^{5b}$, together with the N-atom to which they are attached, represent $Het^A$,
or $R^{5b}$ represents H or alkyl and $R^{5c}$ represents $X^2$—$R^8$;
$X^1$ and $X^2$ independently represent $C(O)$ or $S(O)_2$;
$R^8$ represents
$R^x$,
$OR^{7a}$,
$N(R^{7b})R^{7c}$ or
a structural fragment of the formula

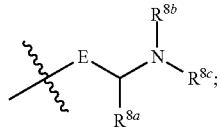

$R^{7a}$ represents $R^x$;
$R^{7b}$ and $R^{7c}$ independently represent H or $R^x$;
E represents a direct bond or phenylene;
$R^{5a}$ and $R^{8a}$ independently represent H or $R^x$;
$R^{8b}$ and $R^{8c}$ independently represent H or $R^x$,
or $R^{8b}$ and $R^{8c}$, together with the N-atom to which they are attached, represent $Het^B$;
$Het^A$ and $Het^B$ independently represent a 5- or 6-membered fully saturated, partly unsaturated or wholly aromatic heterocyclic group containing a N-atom (the atom to which either $R^{5b}$ and $R^{5c}$ or $R^{8b}$ and $R^{8c}$ are attached) and optionally containing one to three further heteroatoms selected from N, O and/or S, which heterocyclic group is optionally fused to a benzene ring and is optionally substituted by one or more substituents selected from $R^x$, halo, $OR^{9a}$, $S(O)_pR^{9b}$, CN, $N_3$, $NO_2$, =O, $B^3-C(O)-B^4-R^{9c}$, $N(R^{9d})R^{9e}$ and $N(OH)R^{9f}$;

$R^6$ represents $C(O)-X^3-R^x$;

$X^3$ represents O or NH;

$R^2$ and $R^3$ independently represent H or $R^x$;

$R^x$ represents, independently at each occurrence, alkyl, alkenyl, alkynyl, cycloalkyl (which latter four groups are optionally substituted by one or more substituents selected from alkyl, alkenyl, alkynyl, cycloalkyl, aryl, $Het^1$, halo, $OR^{4a}$, $S(O)_nR^{4b}$, CN, $N_3$, $NO_2$, =O, $B^1-C(O)-B^2-N(H)-C(=NH)-NH_2$, $N(R^{4d})R^{4e}$ and $N(OH)R^{4f}$), aryl or $Het^2$;

$R^{4a}$ to $R^{4f}$ and $R^{9a}$ to $R^{9f}$ independently represent H, alkyl, alkenyl, alkynyl, cycloalkyl (which latter four groups are optionally substituted by one or more substituents selected from alkyl, alkenyl, alkynyl, cycloalkyl, aryl, $Het^3$, halo, OH, alkoxy, $NH_2$, N(H)alkyl and $N(alkyl)_2$), aryl or $Het^4$;

each aryl independently represents a $0_{6-14}$ carbocyclic aromatic group, which group may comprise one, two or three rings, at least one of which rings must be aromatic, and which aryl group is optionally substituted by one or more substituents selected from alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $Het^5$, halo, $OR^{10a}$, $S(O)_qR^{10b}$, CN, $N_3$, $NO_2$, =O, $B^5-C(O)-B^6-R^{10c}$, $N(R^{10d})R^{10e}$ and $N(OH)R^{10f}$), phenyl (which latter group is optionally substituted by one or more substituents selected from OH, halo, alkyl and alkoxy), $Het^6$, halo, $OR^{11a}$, $S(O)_rR^{11b}$, CN, $N_3$, $NO_2$, $B^7-C(O)-B^8-R^{11c}$, $N(R^{11d})R^{11e}$ and $N(OH)R^{11f}$;

$R^{10a}$ to $R^{10f}$ and $R^{11a}$ to $R^{11f}$ independently represent H, alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $Het^9$, halo, OH, alkoxy, $NH_2$, N(H)alkyl and $N(alkyl)_2$), phenyl (which latter group is optionally substituted by one or more substituents selected from OH, halo, alkyl and alkoxy) or $Het^7$;

$Het^1$ to $Het^7$ independently represent 4- to 14-membered heterocyclic groups containing one or more heteroatoms selected from O, N and/or S, which heterocyclic groups may comprise one, two or three rings and may be substituted by one or more substituents selected from alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $Het^a$, halo, $OR^{12a}$, $S(O)_tR^{12b}$, CN, $N_3$, $NO_2$, =O, $B^9-C(O)-B^{10}-R^{12c}$, $N(R^{12d})R^{12e}$ and $N(OH)R^{12f}$), phenyl (which latter group is optionally substituted by one or more substituents selected from OH, halo, alkyl and alkoxy), $Het^b$, halo, $OR^{13a}$, =O, $S(O)_uR^{13b}$, CN, $N_3$, $NO_2$, $B^{11}-C(O)-B^{12}-R^{13c}$, $N(R^{13d})R^{13e}$ and $N(OH)R^{13f}$;

$R^{12a}$ to $R^{12f}$ and $R^{13a}$ to $R^{13f}$ independently represent H, alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $He^c$, halo, OH, alkoxy, $NH_2$, N(H)alkyl and $N(alkyl)_2$), phenyl (which latter group is optionally substituted by one or more substituents selected from OH, halo, alkyl and alkoxy) or $Het^d$;

$B^1$ to $B^{12}$ independently represent a direct bond, O, S or $N(R^{14})$;

n, p, q, r, t and u independently represent 0, 1 or 2;

$R^{14}$ represents H, alkyl, phenyl (which latter group is optionally substituted by one or more substituents selected from OH, halo, alkyl and alkoxy), cycloalkyl (which latter group is optionally substituted by one or more substituents selected from OH, =O, halo, alkyl and alkoxy) or $Het^e$;

$Het^a$ to $Het^e$ independently represent 5- or 6-membered heterocyclic groups containing one to four heteroatoms selected from O, N and/or S, which heterocyclic groups may be substituted by one or more substituents selected from halo, =O and alkyl; and unless otherwise specified alkyl, alkenyl, alkynyl and cycloalkyl groups, as well as the alkyl part of alkoxy groups, may be substituted by one or more halo atoms.

The invention further provides pharmaceutical compositions comprising a compound of formula I and a pharmaceutically acceptable carrier. Such pharmaceutical compositions may be employed in a method for affecting melanocortin receptor function in a human or non-human mammal, the method comprising the step of administering the pharmaceutical composition. Such pharmaceutical composition may further be employed in a method for treating a condition responsive to changes in melanocortin receptor function in a human or non-human mammal, comprising the step of administering the pharmaceutical composition to the human or non-human mammal in a pharmaceutically effective amount.

The present invention further provides compounds that are agonists or partial agonists of a melanocortin receptor, including one or more of MC1-R, MC3-R, MC4-R, or MC5-R. The compounds alternatively are antagonists of a melanocortin receptor, including one or more of MC1-R, MC3-R, MC4-R, or MC5-R. The compounds alternatively are inverse agonists or partial inverse agonists of a melanocortin receptor, including one or more of MC1-R, MC3-R, MC4-R, or MC5-R. The compounds alternatively are antagonists of an inverse agonist of a melanocortin receptor, including one or more of MC1-R, MC3-R, MC4-R, or MC5-R.

The invention further includes methods for altering a disorder or condition associated with the activity of a melanocortin receptor, comprising administering to a patient a pharmaceutically effective amount a compound of this invention. In one embodiment the disorder or condition is an eating disorder such as cachexia. In another embodiment the disorder or condition is obesity, diabetes, related metabolic syndrome and/or associated impairment of energy homeostasis. In another embodiment the disorder or condition is sexual dysfunction such as erectile dysfunction or female sexual dysfunction. In another embodiment the disorder or condition is an inflammatory process or dysfunction.

One object of the present invention is to provide conformationally constrained and optically pure isomers of spiro-piperidine compounds, wherein the pendant group substituents are amino acid moieties, amino acid side chain moieties or derivatives thereof, such that the resulting ring compound biologically mimics a relevant reverse turn peptide structure.

Another object of the present invention is to provide methods for the synthesis of optically pure spiro-piperidine compounds.

Another object of the present invention is to provide spiro-piperidine core compounds wherein pendant groups are provided, which pendant groups are or include amino acid side chain moieties.

Another object of the present invention is to provide a spiro-piperidine compound wherein such compound is specific for one or more melanocortin receptors.

Another object of the present invention is to provide a method for synthesis of spiro-piperidine compounds of the invention.

Other objects, advantages and novel features, and the further scope of applicability of the present invention will be set forth in part in the detailed description to follow, and in part will become apparent to those skilled in the art upon examination of the following, or may be learned by practice of the invention.

DETAILED DESCRIPTION

1. Compounds of the Invention

The invention relates to compounds of formula I as described above.

Compounds of the invention are useful for treating conditions in mammals associated with the activity of a melanocortin receptor, such as eating disorders, for example, cachexia, obesity, diabetes or related metabolic syndrome, or associated impairment of energy homeostasis, or sexual dysfunction such as erectile dysfunction or female sexual dysfunction.

In certain embodiments, the compounds of formula I are those in which:
(1) $G^1$ and $G^2$ independently represent $CH_2$ or $C(O)$;
(2) $R^1$ represents
  H,
  aryl or
  $C(O)—R^5$;
(3) $R^5$ represents a structural fragment of the formula

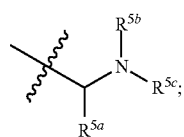

(4) $R^{5a}$ represents
  H,
  alkyl, cycloalkyl (which latter two groups are optionally substituted by one or more substituents selected from alkyl, cycloalkyl, aryl, $Het^1$, halo, $OR^{4a}$, $S(O)_nR^{4b}$, $B^1—C(O)—B^2—R^{4c}$, $N(H)—C(=NH)—NH_2$ and $N(R^{4d})R^{4e}$),
  aryl or
  $Het^2$;
(5) $R^{5b}$ represents H or alkyl;
(6) $R^{5c}$ represents $X^2—R^8$;
(7) $X^2$ represents $C(O)$ or $S(O)_2$;
(8) $R^8$ represents
  H,
  alkyl, cycloalkyl (which latter two groups are optionally substituted by one or more substituents selected from alkyl, cycloalkyl, aryl, $Het^1$, halo, $OR^{4a}$, $S(O)_nR^{4b}$, $B^1—C(O)—B^2—R^{4c}$, $N(H)—C(=NH)—NH_2$ and $N(R^{4d})R^{4e}$),
  aryl,
  $Het^2$,
  O-alkyl or
  a structural fragment of the formula

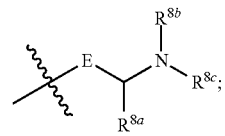

(9) E represents a direct bond or 1,4-phenylene;
(10) $R^{8a}$ represents
  H,
  alkyl, cycloalkyl (which latter two groups are optionally substituted by one or more substituents selected from alkyl, cycloalkyl, aryl, $Het^1$, halo, $OR^{4a}$, $S(O)_nR^{4b}$, $B^1—C(O)—B^2—R^{4c}$, $N(H)—C(=NH)—NH_2$ and $N(R^{4d})R^{4e}$),
  aryl or
  $Het^2$;
(11) $R^{8b}$ and $R^{8c}$ independently represent
  H,
  alkyl, cycloalkyl (which latter two groups are optionally substituted by one or more substituents selected from alkyl, cycloalkyl, aryl, $Het^1$, halo, $OR^{4a}$ and $N(R^{4d})R^{4e}$)
  aryl or
  $Het^2$;
  or $R^{8b}$ and $R^{8c}$, together with the N-atom to which they are attached, represent a 5- or 6-membered fully saturated or wholly aromatic heterocyclic group containing a N-atom (the atom to which $R^{8b}$ and $R^{8c}$ are attached) and optionally containing one or two further heteroatoms selected from N, O and/or S, which heterocyclic group is optionally substituted by one or more substituents selected from alkyl and halo;
(13) $R^2$ represents
  H,
  alkyl, cycloalkyl (which latter two groups are optionally substituted by one or more substituents selected from alkyl, cycloalkyl, aryl, $Het^1$, halo, $OR_{4a, S(O)_n}R^{4b}$, $B^1—C(O)—B^2—R^{4c}$ and $N(R^{4d})R^{4e}$),
  aryl or
  $Het^2$,
(14) $R^3$ represents
  alkyl optionally substituted by one cycloalkyl, aryl or $Het^1$ substituent,
  cycloalkyl optionally substituted by one or two substituents selected from alkyl and halo,
  aryl or
  $Het^2$,
(15) $R^{4a}$ to $R^{4f}$ represent
  H,
  alkyl optionally substituted by one or two substituents selected from cycloalkyl, aryl, $Het^3$, halo, OH, alkoxy, $NH_2$, N(H)alkyl and N(alkyl)$_2$, cycloalkyl optionally substituted by one or two substituents selected from alkyl and halo,
aryl or
Het$^4$;
(16) each aryl independently represents a $C_{6-10}$ carbocyclic aromatic group, which group may comprise one or two rings, at least one of which rings must be aromatic, and which aryl group is optionally substituted by one or more substituents selected from
alkyl optionally substituted by one or more substituents selected from phenyl (which latter group is optionally substituted by one or more substituents selected from OH, halo, alkyl and alkoxy), He$^5$, halo, OR$^{10a}$, S(O)$_q$R$^{10b}$ and N(R$^{10d}$)R$^{10e}$,
halo
OR$^{11a}$,
S(O)$_r$R$^{11b}$,
S(O)$_r$R$^{11b}$,
CN and
N(R$_{11d}$)R$^{113}$;
(17) R$^{10a}$ to R$^{10f}$ and R$^{11a}$ to R$^{11f}$ independently represent
H,
alkyl optionally substituted by one or two substituents selected from cycloalkyl, phenyl (which latter group is optionally substituted by one or more substituents selected from OH, halo, alkyl and alkoxy), Het$^9$, halo, OH, alkoxy, NH$_2$, N(H)alkyl and N(alkyl)$_2$,
cycloalkyl optionally substituted by one or two substituents selected from alkyl and halo,
phenyl (which latter group is optionally substituted by one or more substituents selected from OH, halo, alkyl and alkoxy) or
Het$^7$;
(18) Het$^1$ to Het$^7$ independently represent 5- to 10-membered heterocyclic groups containing one to four heteroatoms selected from O, N and/or S, which heterocyclic groups may comprise one or two rings and may be substituted by one or more substituents selected from
alkyl optionally substituted by one to three substituents selected from phenyl, halo, OR$^{12a}$ and N(R$^{12d}$)R$^{12e}$,
halo,
OR$^{13a}$,
=O and
N(R$^{13d}$)R$^{13e}$;
(19) R$^{12a}$ to R$^{12f}$ and R$^{13a}$ to R$^{13f}$ independently represent
H,
alkyl optionally substituted by one to three substituents selected from halo, OH, alkoxy, NH$_2$, N(H)alkyl and N(alkyl)$_2$,
phenyl or
Het$^d$;
(20) B$^1$ represents a direct bond or N(R$^{14}$);
(21) B$^2$ represents a direct bond, O or N(R$^{14}$);
(22) R$^{14}$ represents H or methyl;
(23) Het$^a$ to Het$^e$ independently represent 5- or 6-membered fully saturated or wholly aromatic heterocyclic groups containing one to three heteroatoms selected from O, N and/or S, which heterocyclic groups may be substituted by one or more substituents selected from halo, =O and alkyl.

In certain further embodiments, the compounds of formula I are those in which:
(1) G$^1$ represents C(O);
(2) G$^2$ represent C(O) or, particularly, CH$_2$;
(3) R$^1$ represents
H,
phenyl optionally substituted by a $C_{1-4}$ alkyl group (which latter group is optionally substituted by one or two substituents selected from halo, OR$^{10a}$ and N(R$^{10d}$)R$^{10e}$), or
C(O)—R$^5$;
(4) R$^{5a}$ represents
H,
$C_{1-6}$ alkyl optionally substituted by a phenyl (which latter group is optionally substituted by one or two substituents selected from $C_{1-4}$ alkyl, trifluoromethyl, halo (e.g. fluoro or chloro), OR$^{11a}$ and CN) or pyridinyl (e.g.pyridin-3-yl or pyridin-4-yl) group or
phenyl optionally substituted by one or two substituents selected from $C_{1-4}$ alkyl, trifluoromethyl, halo (e.g. fluoro or chloro), OR$^{11a}$ and CN;
(5) R$^{5b}$ represents H or methyl;
(6) R$^8$ represents
$C_{1-6}$ alkyl optionally substituted by one to three substituents selected from Het$^1$, halo and N(R$^{4d}$)R$^{4e}$,
$C_{5-6}$ cycloalkyl,
phenyl optionally substituted by one or two substituents selected from $C_{1-4}$ alkyl (which latter group is optionally substituted by one or two substituents selected from Het$^5$, halo, OR$^{10a}$ and N(R$^{10d}$)R$^{10e}$), halo and OR$^{11a}$,
Het$^2$,
O—($C_{1-6}$ alkyl) or
a structural fragment of the formula (7) R$^{8a}$ represents
H or
$C_{1-4}$ alkyl optionally substituted by a Het$^1$ group;
(8) R$^{8b}$ represents H or $C_{1-2}$ alkyl,
R$^{8c}$ represents
H,
$C_{1-6}$ alkyl optionally substituted by one or two substituents selected from phenyl (which latter group is optionally substituted by one or two substituents selected from halo and) OR$^{11a}$), Het$^1$, halo, OR$^{4a}$ and N(R$^{4d}$)R$^{4e}$ or
$C_{5-6}$ cycloalkyl,
or R$^{8b}$ and R$^{8c}$, together with the N-atom to which they are attached, represent a 5- or 6-membered fully saturated or wholly aromatic heterocyclic group containing a N-atom (the atom to which R$^{8b}$ and R$^{8c}$ are attached) and optionally containing one further heteroatom selected from N and O, which heterocyclic group is optionally substituted by one or two $C_{1-2}$ alkyl substituents;
(9) R$^2$ represents
H,
$C_{1-6}$ alkyl optionally substituted by one or two substituents selected from phenyl (which latter group is optionally substituted by one or two substituents selected from halo and) OR$^{11a}$), Het$^1$, halo, OR$^{4a}$, B$^1$—C(O)—B$^2$—R$^{4c}$ and N(R$^{4d}$)R$^{4a}$), or $C_{5-6}$ cycloalkyl,
(10) R$^3$ represents
$C_{1-4}$ alkyl optionally substituted by one phenyl (which latter group is optionally substituted by one or two halo (e.g. chloro) substituents) or pyridinyl (e.g. pyridin-3-yl) group, C$_{5-6}$ cycloalkyl or phenyl optionally substituted by one or two substituents selected from halo (e.g. chloro) and OR$^{11a}$,

(11) R$^{4a}$ and R$^{4d}$ independently represent H or C$_{1-2}$ alkyl;

(12) R$^{4c}$ and R$^{4e}$ independently represent

H,

C$_{1-6}$ alkyl optionally substituted by one or two substituents selected from phenyl (which latter group is optionally substituted by one or two substituents selected from C$_{1-2}$ alkyl, halo and OR$^{11a}$), Het$^3$, halo, OH, C$_{1-2}$ alkoxy and NH$_2$, C$_{5-6}$ cycloalkyl, phenyl optionally substituted by one or two substituents selected from halo and OR$^{11a}$ or Het$^4$;

(13) R$^{10a}$ and R$^{10d}$ independently represent H or C$_{1-2}$ alkyl;

(14) R$^{10e}$ represents

H,

C$_{1-6}$ alkyl optionally substituted by one or two substituents selected from phenyl, Het$^9$, halo, OH, C$_{1-2}$ alkoxy and NH$_2$ or C$_{5-6}$ cycloalkyl;

($_{15}$) R$^{11a}$ represents H or, particularly, C$_{1-2}$ alkyl;

(16) Het$^1$, Het$^4$, Het$^5$ and Het$^9$ independently represent a 5- or 6-membered, monocyclic, fully saturated or wholly aromatic heterocyclic group containing one to three heteroatoms selected from O, N and/or S, which heterocyclic group may be substituted by one or more substituents selected from C$_{1-2}$ alkyl, OH, halo and =O;

(17) Het$^2$ and Het$^3$ independently represent a 5- to 10-membered, fully saturated, partly aromatic or wholly aromatic heterocyclic group containing one to three heteroatoms selected from O, N and/or S, which heterocyclic group may comprise one or two rings and be substituted by one or more substituents selected from C$_{1-2}$ alkyl, OH, halo and =O;

(18) B$^1$ represents a direct bond or N(H);

(19) B$^2$ represents a direct bond, O, N(H) or N(CH$_3$).

Compounds of formula I that may be mentioned are compounds of formula Ia,

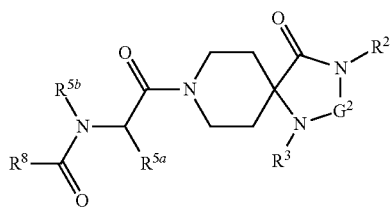

Ia or an enantiomer, stereoisomer or diastereoisomer thereof, or a pharmaceutically acceptable salt thereof, wherein R$^2$, R$^3$, R$^{5a}$, R$^{5b}$, R$^8$ and G$^2$ are as hereinbefore defined.

Compounds of formula Ia that may be mentioned are compounds of formula Ib,

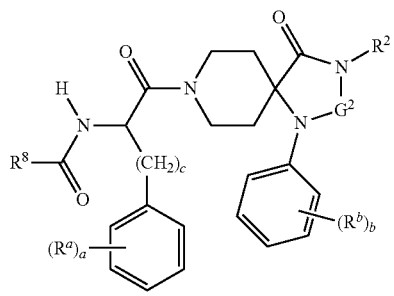

Ib or an enantiomer, stereoisomer or diastereoisomer thereof, or a pharmaceutically acceptable salt thereof, wherein:

R$^a$ represents, independently at each occurrence, CN, trifluoromethyl, methoxy, fluoro or, particularly, chloro;

R$^b$ represents, independently at each occurrence, fluoro or, particularly, chloro;

a and b independently represent 0, 1 or 2;

c represents 0 or 1; and

R$^2$, R$^8$ and G$^2$ are as hereinbefore defined.

In particular embodiments, the compounds of formula Ia are those in which:

(1) R$^{5a}$ represents

H,

C$_{1-4}$ alkyl, methyl substituted by a phenyl (which latter group is optionally substituted by one or two substituents selected from trifluoromethyl, fluoro, chloro, methoxy and CN) or pyridinyl (e.g.pyridin-3-yl or pyridin-4-yl) group or phenyl optionally substituted by one or two substituents selected from trifluoromethyl, fluoro, chloro, methoxy and CN;

(2) R$^{5b}$ represents H;

(3) R$^8$ represents

C$_{1-4}$ alkyl optionally substituted by one or two substituents selected from piperidinyl (e.g. piperidin-1-yl), morpholinyl (e.g. morpholin-1-yl), piperazinyl (e.g. piperazin-1-yl), 4-methylpiperazinyl (e.g. 4-methylpiperazin-1-yl), imidazolyl (e.g. imidazol-1-yl or midazol-5-yl), 1-methylimidazolyl (e.g. 1-methylimidazol-5-yl), and N(R$^{4d}$)R$^{4e}$, C$_{5-6}$ cycloalkyl, pyrrolidinyl (e.g. pryyolidin-2-yl), piperidinyl (e.g. piperidin-2-yl, piperidin-3-yl or piperidin-4-yl), pyridinyl (e.g. pyridin-2-yl, pyridin-3-yl or pyridin-4-yl), 1,2,3,4-tetrahydroisoquinolinyl (e.g. 1,2,3,4-tetrahydroisoquinolin-1-yl or, particularly, 1,2,3,4-tetrahydroisoquinolin-3-yl), O—(C$_{1-4}$ alkyl) or a structural fragment of the formula

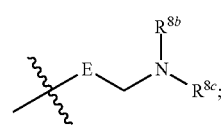

(4) R$^{8b}$ represents

H or methyl,

R$^{8c}$ represents

H,

C$_{1-4}$ alkyl, $C_{1-2}$ alkyl substituted by a phenyl, OH, methoxy or $NH_2$ group or $C_{5-6}$ cycloalkyl, or $R^{8b}$ and $R^{8c}$, together with the N-atom to which they are attached, represent a piperidin-1-yl, morpholin-1-yl, piperazin-1-yl, 4-methylpiperazin-1-yl or imidazol-1-yl group;

(5) $R^2$ represents

H, $C_{1-4}$ alkyl optionally substituted by a OH, phenyl (which latter group is optionally substituted by one or two halo (e.g. chloro) groups), pyridinyl (e.g. pyridin-2-yl or pyridin-3-yl), triazolyl (e.g. 1,2,4-triazol-1-yl), piperidinyl (e.g. piperidin-1-yl) or morpholinyl (e.g. morpholin-1-yl) group, $C_{5-6}$ cycloalkyl or a structural fragment of the formula

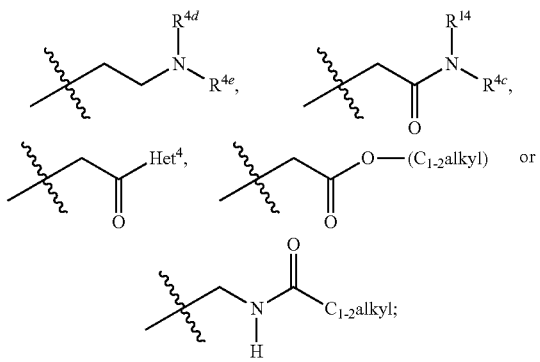

(6) $R^{4c}$ represents $C_{1-5}$ alkyl, $C_{1-2}$ alkyl substituted by a phenyl (which latter group is optionally substituted by one or two substituents selected from $C_{1-2}$ alkyl and methoxy), or indolyl (e.g. indol-3-yl) group, $C_{5-6}$ cycloalkyl or phenyl;

(7) represents H or $C_{1-2}$ alkyl;

(8) $R^{4a}$ represents

H, $C_{1-4}$ alkyl, $C_{1-2}$ alkyl substituted by a phenyl (which latter group is optionally substituted by one or two halo groups), thienyl (e.g. thien-2-yl), OH or methoxy group or $C_{5-6}$ cycloalkyl;

(9) $R^{14}$ represents methyl or, particularly, H;

(10) $Het^4$ represents piperazin-1-yl optionally substituted (e.g. in the 4-position) by $C_{1-2}$ alkyl;

(11) $R^3$ represents methyl substituted by a phenyl or, particularly, pyridinyl (e.g.pyridin-3-yl) group, $C_{5-6}$ cycloalkyl or phenyl optionally substituted by one or two chloro groups;

(12) $G^2$ represents $CH_2$ or C(O).

Further, in particular embodiments, the compounds of formula Ib are those in which:

(1) $R^8$ represents $C_{2-4}$ alkyl (e.g. $C_{1-3}$ alkyl, such as n-propyl) terminally substituted by $NH_2$ or, particularly 1,2,3,4-tetrahydroisoquinolinyl (e.g. 1,2,3,4-tetrahydroisoquinolin-1-yl or, particularly, 1,2,3,4-tetrahydroisoquinolin-3-yl);

(2) $R^a$ and $R^b$ independently represent halo (e.g. chloro);

(3) a represents 0 or, particularly, 1 or 2;

(4) b represents 1 or, particularly, 0;

(5) c represents 0 or, particularly, 1;

(6) $G^2$ represents $CH_2$ or C(O).

Compounds of formula I that may be mentioned are compounds of formula 1c,

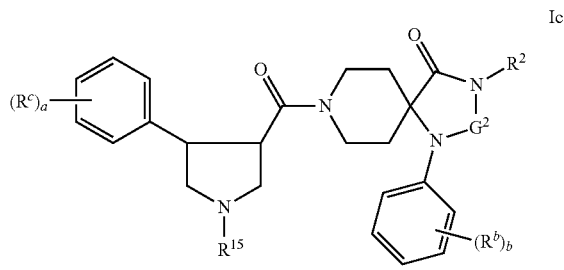

or an enantiomer, stereoisomer or diastereoisomer thereof, or a pharmaceutically acceptable salt thereof, wherein:

$R^b$ represents, independently at each occurrence, fluoro or chloro;

$R^c$ represents, independently at each occurrence, —OH, halo, alkyl or alkoxy;

a and b independently represent 0, 1 or 2;

$R^{15}$ represents alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $Het^a$, halo, $OR^{12a}$, $S(O)_tR^{12b}$, CN, $N_3$, $NO_2$, =O, $B^9$—C(O)—$B^{10}$—$R^{12c}$, $N(R^{12d})R^{12e}$ and $N(OH)R^{12d}$), phenyl (which latter group is optionally substituted by one or more substituents selected from OH, halo, alkyl and alkoxy), $Het^b$, halo, $OR^{13a}$, =O, $S(O)_uR^{13b}$, CN, $N_3$, $NO_2$, $B^{11}$—C(O)—$B^{12}$—$R^{13c}$, $N(R^{13d})R^{13e}$ and $N(OH)R^{13f}$;

$G^2$ represents $CH_2$ or C(O); and $R^2$ is as hereinbefore defined.

Hereinafter, references to compounds of formula I are, unless the context indicates otherwise, intended to include references to compounds of formula Ia and/or formula Ib and/or formula Ic. Conversely, where reference is made to particular embodiments of the compounds of formula Ia or Ib or Ic, these embodiments apply equally, where relevant, to compounds of formula I.

2. Isomeric Purity and Isolation

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass the racemic form of compounds of the invention as well as all enantiomers and stereoisomers, that is, both the stereomerically pure form (e.g., geometrically pure, enantiomerically pure, or diastereomerically pure) and enantiomeric and stereoisomeric mixtures.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically enriched form when the compound has an enantiomeric excess of greater than about 80% ee, preferably greater than about 90% ee. As used herein, a racemic mixture means about 50% of one enantiomer and about 50% of its corresponding enantiomer relative to all chiral centers in the molecule. Thus, the invention encompasses all enantiomerically pure, enantiomerically enriched, and racemic mixtures of compounds of the invention.

Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

When administered to a patient, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, the compounds of the invention are purified by conventional techniques. As used herein, "purified" means that when isolated, the isolate contains at least 95%, preferably at least 98%, of a single compound of the invention (or an enantiomeric or diastereomeric mixture thereof) by weight of the isolate.

3. Definitions

"treat", "treating" and "treatment"

The terms "treat," "treating" and "treatment," as used herein, contemplate an action that occurs while a patient is suffering from the specified disease or disorder, which reduces the severity of the disease or disorder.

"pharmaceutically effective amount"

As used herein, the term "pharmaceutically effective amount" means the amount of a compound of the invention that will elicit a biological or medical response in the mammal that is being treated by a medical doctor or other clinician.

"prophylactically effective", "preventing" or "preventive"

As used herein, the term "prophylactically effective" or "preventive" means the amount of a compound of the invention that will prevent or inhibit affliction or mitigate affliction of a mammal with a medical condition that a medical doctor or other clinician is trying to prevent, inhibit, or mitigate before a patient begins to suffer from the specified disease or disorder.

"pharmaceutically acceptable salt(s)"

The term "pharmaceutically acceptable salt(s)", as used herein includes but is not limited to salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

"alkyl"

As used herein, the term "alkyl" means a saturated, monovalent, unbranched or branched hydrocarbon chain. Examples of alkyl groups include, but are not limited to, $C_{1-6}$ alkyl groups, such as methyl, ethyl, propyl, isopropyl, 2-methyl-1-propyl, 2-methyl-2-propyl, 2-methyl-1-butyl, 3-methyl-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl and octyl.

"alkenyl"

As used herein, the term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to $C_{2-6}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene) pentenyl.

"alkynyl"

As used herein, the term "alkynyl" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $C_{2-6}$ alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl.

"aryl"

As indicated above, "aryl" groups of the present invention are $C_{6-14}$ carbocyclic aromatic groups. These aryl groups may comprise one, two or three rings, at least one of which rings must be aromatic. Examples of suitable aryl groups include, but are not limited to, phenyl, anthacenyl, fluorenyl, indenyl, azulenyl and naphthyl as well as part-aromatic, bi- or tricyclic moieties such as indanyl or 5,6,7,8-tetrahydronaphthyl. Preferably, an aryl group is a phenyl ring.

$Het^1$ to $Het^{10}$, $Het^a$ to $Het^e$, $Het^A$ and $Het^B$

Heterocyclic groups $Het^1$ to $Het^7$ and $Het^a$ to $Het^e$ may be fully saturated, partly unsaturated, wholly aromatic or partly aromatic in character. Values of heterocyclic ($Het^1$ to $Het^7$ and $Het^a$ to $Het^e$) groups that may be mentioned include 1-azabicyclo[2.2.2]octanyl, benzimidazolyl, benzo[c]isoxazolidinyl, benzisoxazolyl, benzodioxanyl, benzodioxepanyl, benzodioxolyl, benzofuranyl, benzofurazanyl, benzomorpholinyl, 2,1,3-benzoxadiazolyl, benzoxazolidinyl, benzoxazolyl, benzopyrazolyl, benzo[e]pyrimidine, 2,1,3-benzothiadiazolyl, benzothiazolyl, benzothienyl, benzotriazolyl, chromanyl, chromenyl, cinnolinyl, 2,3-dihydrobenzimidazolyl, 2,3-dihydrobenzo[b]furanyl, 1,3-dihydrobenzo-[c]furanyl, 1,3-dihydro-2,1-benzisoxazolyl 2,3-dihydropyrrolo[2,3-b]pyridinyl, dioxanyl, furanyl, hexahydro-pyrimidinyl, hydantoinyl, imidazolyl, imidazo[1, 2-a]pyridinyl, imidazo[2,3-b]thiazolyl, indolyl, isoquinolinyl, isoxazolidinyl, isoxazolyl, maleimido, morpholinyl, naphtho[1,2-b]furanyl, oxadiazolyl, 1,2- or 1,3-oxazinanyl, oxazolyl, phthalazinyl, piperazinyl, piperidinyl, purinyl, pyranyl, pyrazinyl, pyrazolyl, pyridazinyl, pyridinyl, pyrimidinyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydro-benzimidazolyl, 4,5,6,7-tetrahydrobenzopyrazolyl, 5,6,7,8-tetrahydro-benzo[e]-pyrimidine, tetrahydrofuranyl, 1,2,3,4-tetrahydroisoquinolinyl, tetrahydropyranyl, 3,4,5,6-tetrahydropyridinyl, 1,2,3,4-tetrahydropyrimidinyl, 3,4,5,6-tetrahydropyrimidinyl, 1,2,3,4-tetrahydroquinolinyl, tetrazolyl, thiadiazolyl, thiazolidinyl, thiazolyl, thienyl, thieno[5,1-c]pyridinyl, thiochromanyl, triazinyl, triazolyl, 1,3,4-triazolo[2,3-b]pyrimidinyl, xanthenyl and the like.

Values of $Het^1$ that may be mentioned include imidazolyl (e.g. imidazol-1-yl), morpholinyl (e.g. morpholin-4-yl), piperazinyl (e.g. piperazin-1-yl), piperidinyl (e.g. piperidin-1-yl) and pyridinyl (e.g. pyridin-2-yl, pyridin-3-yl or pyridin-4-yl).

Values of $Het^2$ that may be mentioned include morpholinyl (e.g. morpholin-4-yl), piperidinyl (e.g. piperidin-1-yl, piperidin-2-yl, piperidin-3-yl or piperidin-4-yl), pyridinyl (e.g. pyridin-2-yl, pyridin-3-yl or pyridin-4-yl), pyrrolidinyl (e.g. pyrrolidin-2-yl), 1,2,3,4-tetrahydroisoquinolinyl (e.g. 1,2,3,4-tetrahydroisoquinolin-1-yl or 1,2,3,4-tetrahydroisoquinolin-3-yl) and triazinyl (e.g. 1,2,4-triazin-1-yl).

Values of $Het^3$ that may be mentioned include indolyl (e.g. indol-3-yl) and thienyl (e.g. thien-2-yl).

Values of $Het^4$ that may be mentioned include piperazinyl (e.g. piperazin-1-yl).

Values of $Het^5$ that may be mentioned include imidazolyl (e.g. imidazol-1-yl or imidazol-5-yl), morpholinyl (e.g. morpholin-4-yl), piperazinyl (e.g. piperazin-1-yl) and piperidinyl (e.g. piperidin-1-yl).

Values of $Het^9$ that may be mentioned include imidazolyl (e.g. imidazol-1-yl or imidazol-5-yl), morpholinyl (e.g. morpholin-4-yl), piperazinyl (e.g. piperazin-1-yl) and piperidinyl (e.g. piperidin-1-yl).

Heterocyclic groups $Het^A$ and $Het^B$ may be fully saturated, partly unsaturated or wholly aromatic in character. As mentioned above, the groups $Het^A$ and $Het^B$ may also be fused to a benzene ring. In this respect, values of $Het^A$ and $Het^B$ groups that may be mentioned include benzimidazolyl, benzomorpholinyl, benzopyrazolyl, benzotriazolyl, 2,3-dihydrobenzimidazolyl, hexahydropyrimidinyl, hydantoinyl, imidazolyl, indolyl, isoxazolidinyl, maleimido, morpholinyl, piperazinyl, piperidinyl, pyrazolyl, pyrrolidinyl, pyrrolinyl, pyrrolyl, 1,2,3,4-tetrahydroisoquinolinyl, 1,2,3,4-tetrahydropyrimidinyl, 3,4,5,6-tetrahydropyrimidinyl, 1,2,3,4-tetrahydroquinolinyl, tetrazolyl, thiazolidinyl, triazolyl and the like.

Values of $Het^B$ that may be mentioned include imidazolyl (e.g. imidazol-1-yl), morpholinyl (e.g. morpholin-4-yl), piperazinyl (e.g. piperazin-1-yl) and piperidinyl (e.g. piperidin-1-yl).

"cycloalkyl"

As used herein, the term "cycloalkyl" means a $C_{3-12}$ (e.g. $C_{3-7}$) monocyclic or polycyclic saturated ring comprising carbon and hydrogen atoms and having no carbon-carbon multiple bonds. Examples of cycloalkyl groups include, but are not limited to, $C_{3-7}$ cycloalkyl groups, such as cyclopropyl, cyclobutyl, cyclopentyl, cyclohexyl, and cycloheptyl.

"alkoxy"

As used herein, the term "alkoxy" means an —O-alkyl group, wherein alkyl is as defined above. Preferably, the alkyl chain of an alkyloxy group is from 1 to 6 carbon atoms in length.

"halogen", "halo"

As used herein, the term "halogen" means fluorine, chlorine, bromine, or iodine. Correspondingly, the meaning of the term "halo" encompasses fluoro, chloro, bromo, and iodo.

4. Synthesis of Compounds of the Invention

The compounds of the invention can be obtained via standard, synthetic methodology. Some convenient methods are illustrated in Schemes 1 to 8 below. Starting materials useful for preparing the compounds of the invention and intermediates therefor, are commercially available or can be prepared from commercially available materials using known synthetic methods and reagents.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed or converted to the desired group at a later stage of the synthesis and compounds bearing such protecting groups thus are of importance primarily as chemical intermediates (although some derivatives also exhibit biological activity). Accordingly, the precise structure of the protecting group is not critical.

Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schroder and Lubke, Academic Press, London and New York, 1965; "Methoden der organischen Chemie", Houben-Weyl, 4th Edition, Vol.15/I, Georg Thieme Verlag, Stuttgart 1974; "Protective Groups in Organic Synthesis", 4th Revised edition T.W. Greene & P.G.M. Wutz, Wiley, New York, December 2006, the disclosures of which are incorporated herein by reference.

Scheme 1 illustrates one methodology for the synthesis of compounds of the invention of the formula 1-5.

Scheme 1

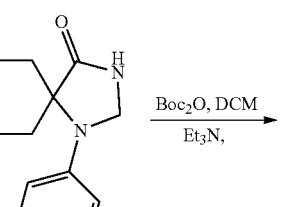

1-1

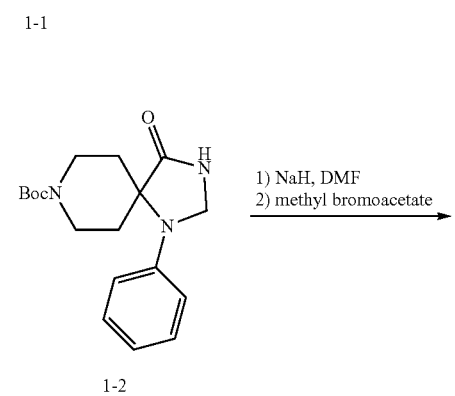

1-2

17

-continued

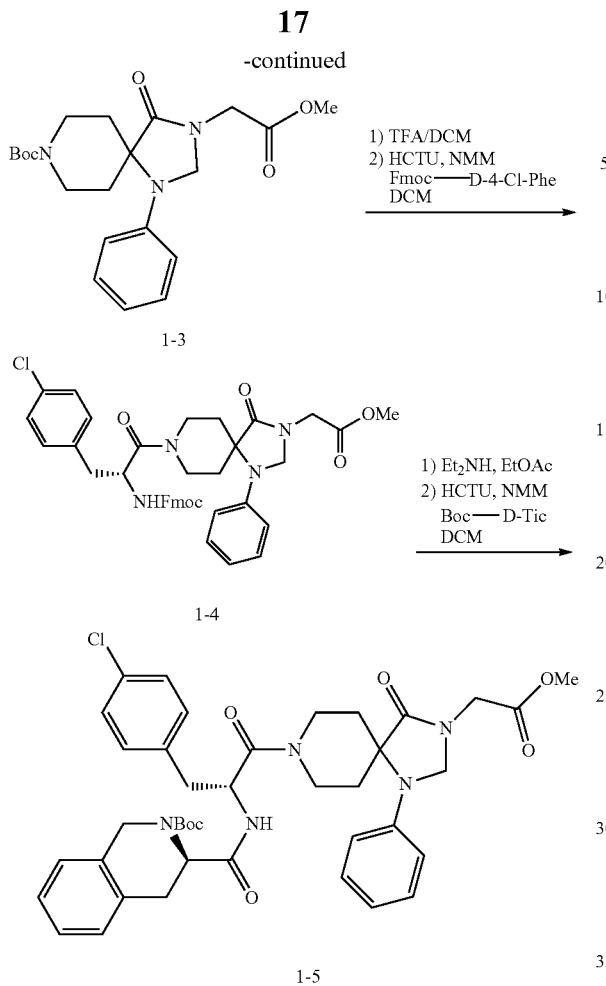

1-3

1-4

1-5

Method for Scheme 1

1-Phenyl-1,3,8-triazaspiro[4.5]-decan-4-one (1-1) and triethylamine ($Et_3N$) (1 eq.) were dissolved in dichloromethane (DCM). To this mixture was added di-t-butyl dicarbonate ($Boc_2O$) (1 eq.). The reaction mixture was stirred at room temperature for 16 hours. The solvent was removed and the residue was purified on a silica gel column to give product 1-2.

To a suspension of sodium hydride (1.2 eq.) in dry dimethylformamide (DMF) was added a solution of compound 1-2 in dimethylformamide slowly at room temperature. The reaction mixture was stirred for 2 hours. To this solution was added bromoacetyl methyl ester. The reaction was carried out at room temperature overnight. The solvent was removed and the residue was purified on a silica gel column to give product 1-3.

Compound 1-3 was treated by 50% trifluoroacetate (TFA) in DCM for 1 hour at room temperature. After removal of solvent the residue was neutralized by N-methylmorpholine (NMM) in DCM. To this solution was added NMM (1 eq.), Fmoc-D-4-Cl-Phe-OH (1 eq.) and HCTU (1 eq.). The mixture was stirred at room temperature overnight. The solvent was removed and the residue was purified on a silica gel column to give product 1-4.

Compound 1-4 was dissolved in 33% diethylamine ($Et_2NH$) in ethylacetate (EtOAc). The mixture was stirred for 3 hours and the solvent was removed. The residue was dissolved in DCM and to the solution were added NMM (1.2 eq.), Boc-D-Tic-OH (1.2 eq.) and HCTU (1.2 eq.). The reac-

18 tion was carried out overnight at room temperature. After removal of solvent the residue was purified on a silica gel column to give product 1-5.

Scheme 2 illustrates one methodology for the synthesis of compounds of the invention of the formulas 2-2, 2-3 and 2-5.

Scheme 2

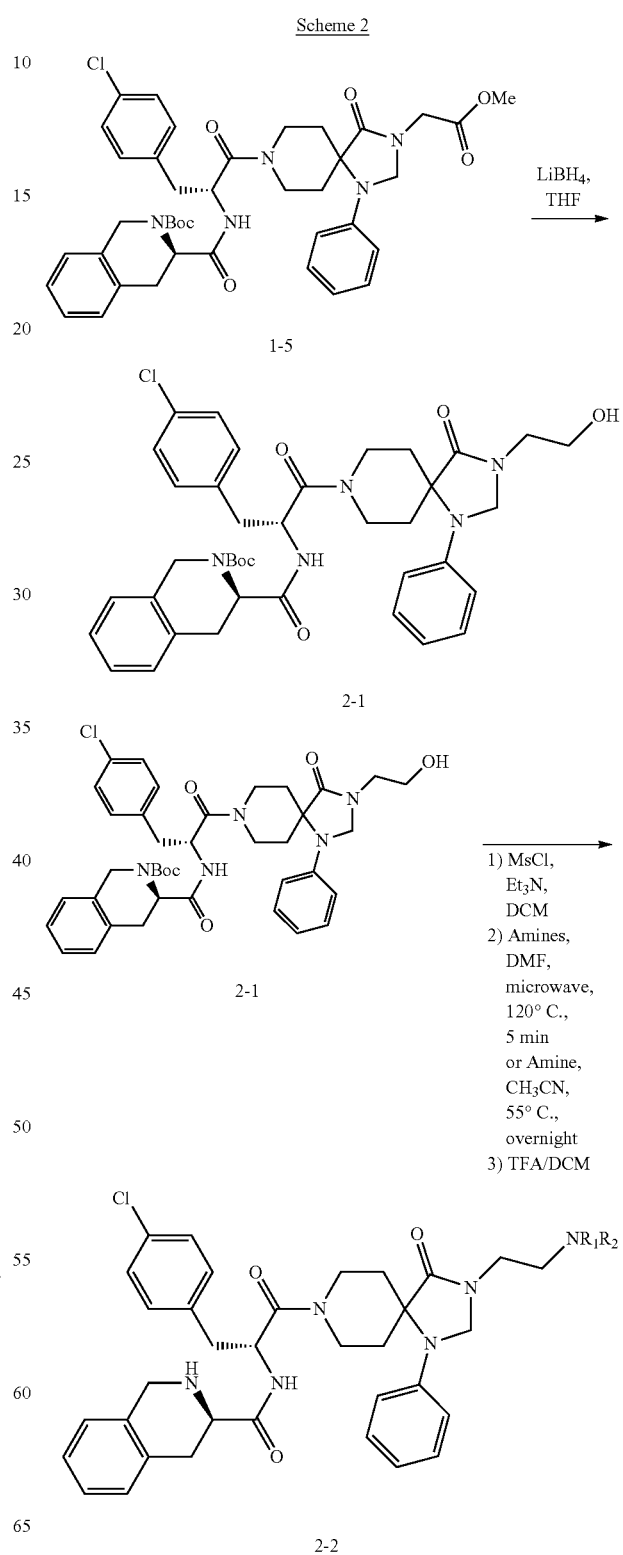

1-5

2-1

2-1

2-2

-continued

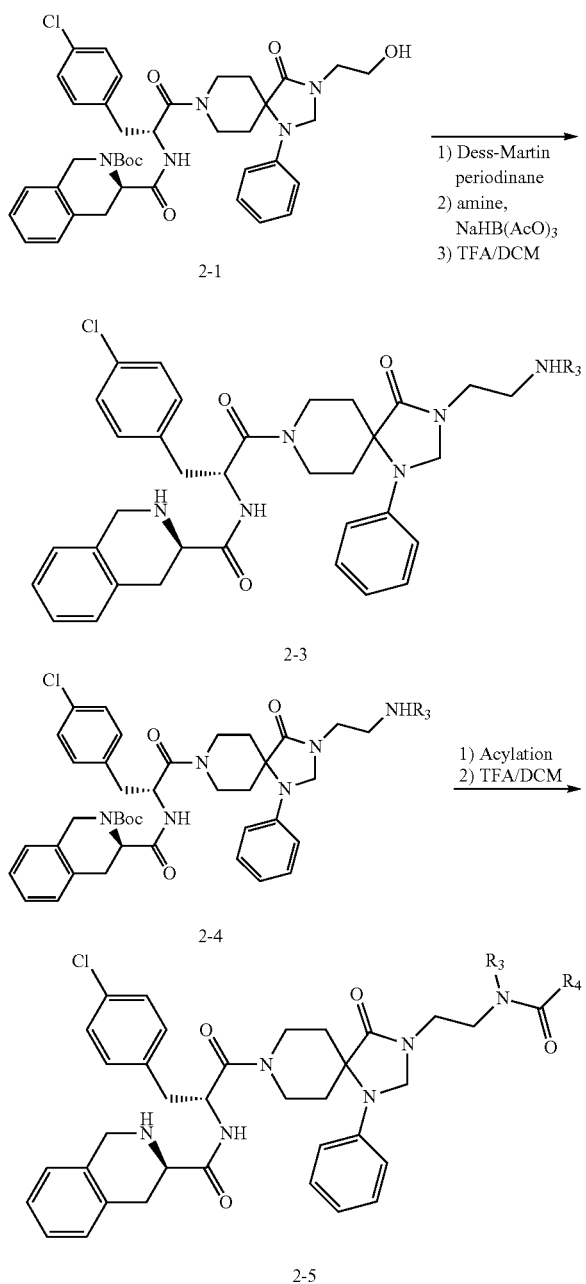

2-1

2-3

2-4

2-5

Methods for Scheme 2

Compound 1-5 was dissolved in tetrahydrofuran (THF). To this solution was added lithium borohydride (LiBH$_4$) (2 eq.) in one portion. The mixture was stirred at room temperature for 1.5 hours. After removal of solvent the residue was purified on a silica gel column to give product 2-1.

Compound 2-1 was dissolved in DCM. To this solution was added triethylamine (2 eq.) and methanesulfonyl chloride (MsCl) (2 eq.) at 0° C. The solution was stirred at room temperature for 1.5 hours and the solvent was removed. The residue was partitioned between ethyl acetate and water. The organic phase was washed by water, brine and dried over sodium sulfate. The solvent was removed and the mesylated product was used for next step reaction without purification.

This mesylated compound was mixed with desired amine (10 eq.) in dimethylformamide. The reaction was carried out under microwaved condition at 120° C. for 5 minutes by using microwave synthesizer (CEM Explorer). The solvent was removed subsequently and the residue was purified on a silica gel column. The obtained product then was treated by trifluoroacetic acid (TFA) for 1 hour. After removal of solvent the residue was purified by HPLC to give pure product 2-2.

Alternatively, this mesylated compound was dissolved in CH$_3$CN, a large excess of amine was added (10% of the total volume) and the mixture was heated overnight at 55° C. Volatiles were removed and the residue was purified on preparative. HPLC. The purified product was treated with TFA/CH$_2$Cl$_2$ (1:1 v/v) for 10 minutes. Volatiles were removed and the product was lyophilized from water/acetonitrile.

Alternatively, compound 2-1 was dissolved in DCM. To this solution was added Dess-Martin periodinane (1.2 eq.). The mixture was stirred for 2 hours at room temperature. The reaction was diluted with ether and a saturated sodium bicarbonate/sodium thiosulfate solution was added. The mixture was stirred for 10 minutes. The organic phase was washed by sodium bicarbonate solution, brine and dried over sodium sulfate. The solvent was removed and the resulting aldehyde product was used for next step reaction without further purification.

The above-mentioned compound was mixed with desired amine (2 eq.) in the presence of 4 Å molecular sieves in dry THF. The mixture was stirred for 2 hours. To this mixture was added triacetoxyborohydride (2 eq.). The reaction mixture was stirred at room temperature overnight. The solvent was evaporated and ethyl acetate and water was added. The organic phase was washed by water, brine and dried over sodium sulfate. After removal of solvent the residue was purified on a silica gel column. The product was treated by 30% TFA in DCM for 1 hour at room temperature. The solvent was removed and the residue was purified by HPLC to give product 2-3.

To compound 2-4 1.0 mL DCM N,N'-diisopropylethylamine (4 eq.) was added followed by acetic anhydride (2 eq.). The mixture was stirred for 3 hours at room temperature, then 1 mL of methanol was added. Stirring was continued for 1 hour at room temperature. Volatiles were removed in vacuo and to the residue in 1 mL DCM was added 1 mL TFA. The mixture was stirred at room temperature for 30 minutes and then volatiles were removed in vacuo. The residue was purified by HPLC to give 2-5.

Scheme 3 illustrates one methodology for the synthesis of compounds of the invention of the formula 3-2.

Scheme 3

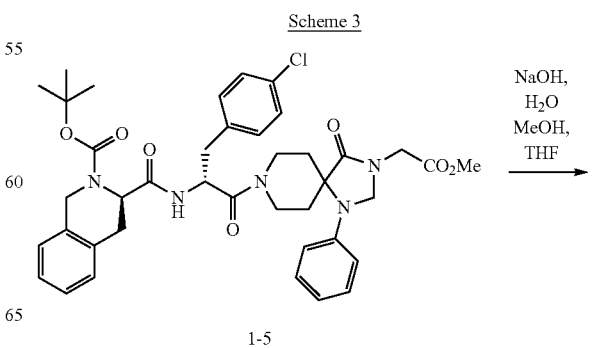

1-5

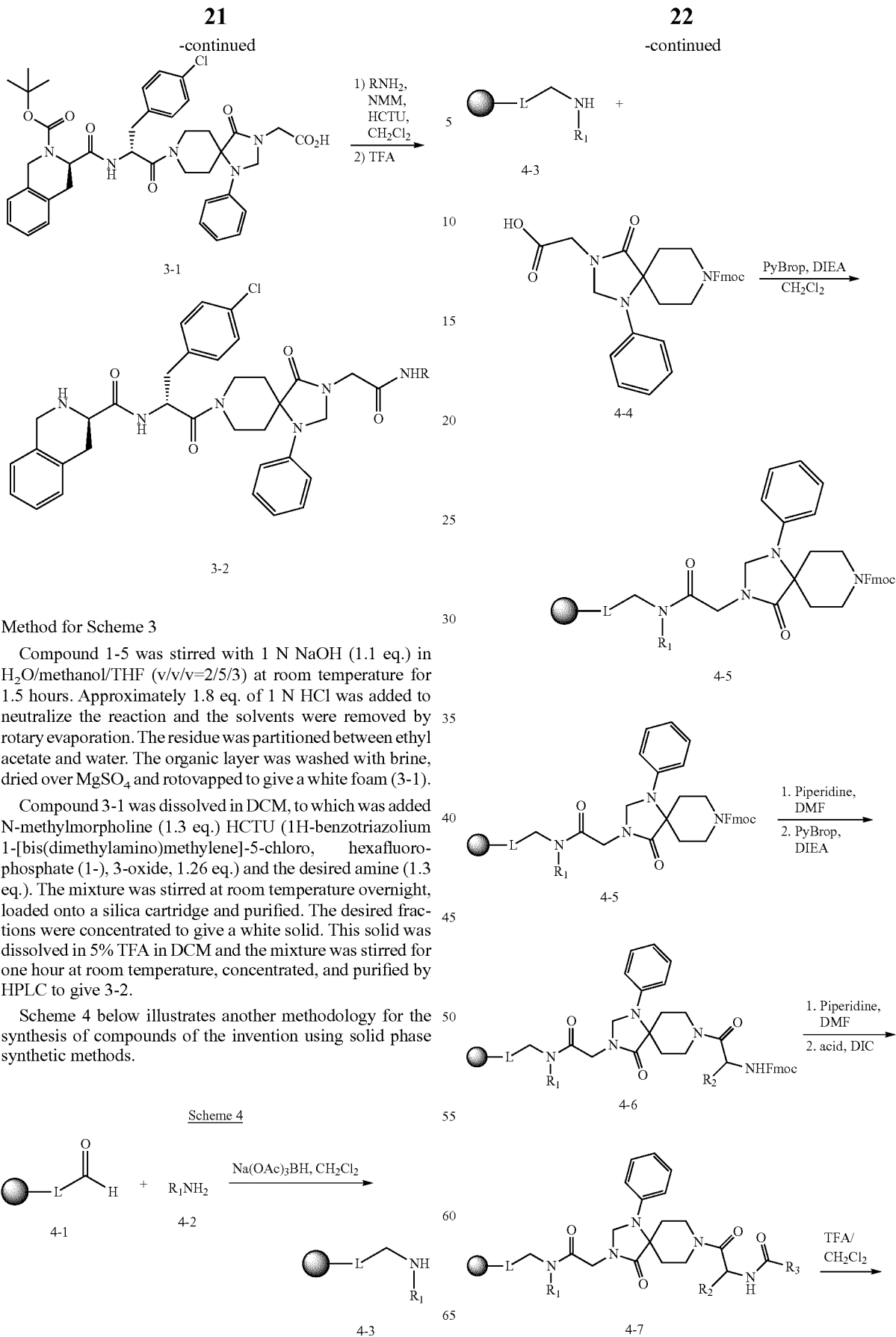

Method for Scheme 3

Compound 1-5 was stirred with 1 N NaOH (1.1 eq.) in $H_2O$/methanol/THF (v/v/v=2/5/3) at room temperature for 1.5 hours. Approximately 1.8 eq. of 1 N HCl was added to neutralize the reaction and the solvents were removed by rotary evaporation. The residue was partitioned between ethyl acetate and water. The organic layer was washed with brine, dried over $MgSO_4$ and rotovapped to give a white foam (3-1).

Compound 3-1 was dissolved in DCM, to which was added N-methylmorpholine (1.3 eq.) HCTU (1H-benzotriazolium 1-[bis(dimethylamino)methylene]-5-chloro, hexafluorophosphate (1-), 3-oxide, 1.26 eq.) and the desired amine (1.3 eq.). The mixture was stirred at room temperature overnight, loaded onto a silica cartridge and purified. The desired fractions were concentrated to give a white solid. This solid was dissolved in 5% TFA in DCM and the mixture was stirred for one hour at room temperature, concentrated, and purified by HPLC to give 3-2.

Scheme 4 below illustrates another methodology for the synthesis of compounds of the invention using solid phase synthetic methods.

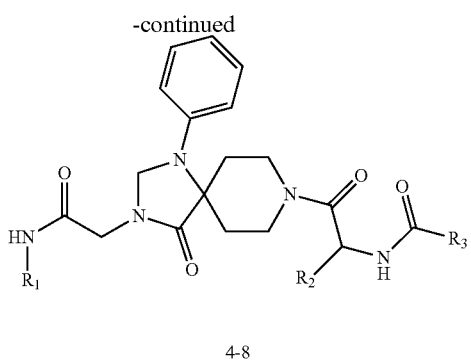

4-8

Method for Scheme 4

Reductive Amination with a Primary Amine To a shaking vessel containing a suspension of 1.0 g (0.4 mmol/g, 0.4 mmol, 1.0 eq.; ArgoGel-MB CHO) of resin-bound o-methoxybenzaldehyde 4-1 in 18 mL of methylene chloride was added 9 mmol (0.5 M, 22.5 eq.) of an amine 4-2. The resin suspension was shaken for 15 seconds and 1.91 g (9 mmol, 0.5 M, 22.5 eq.) of sodium triacetoxyborohydride was added as a solid. This suspension was shaken for 16 hours at 25° C. The shaking vessel was then drained, and the resin was washed with methanol (two times), methylene chloride (two times), methanol (two times), then again with methylene chloride (two times). The resulting resin-bound secondary amine 4-3 gave a positive result with the bromophenol blue staining test. The resin was dried in vacuo.

Acylation with Fmoc-3-carboxymethyl-1-phenyl-1,3,8-triazaspiro[4.5]decan-4-one (4-4) To 1.0 g (0.35 mmol/g, 0.35 mmol) of resin-bound secondary amine 4-3 in 20 mL of methylene chloride was added 2.56 g of Fmoc-3-carboxymethyl-1-phenyl-1,3,8-triazaspiro[4.5]decan-4-one (0.25 M, 5 mmol) (4-4) followed by 1.74 mL of N,N-diisopropylethylamine (0.5 M, 10 mmol, 1.29 g). This mixture was shaken until the acid dissolved and then 2.33 g of PyBrop (0.25 M, 5 mmol) was added. The resulting mixture was shaken at 25° C. for 16 hours. The shaking vessel was drained and the resin was washed with methylene chloride (two times), methanol (two times), methylene chloride (two times), and methylene chloride (two times). The resulting resin-bound amide 4-5 gave a negative result with the bromophenol blue staining test. The resin was dried in vacuo.

Fmoc deprotection To 1.0 g (0.35 mmol/g, 0.35 mmol) of the resin bound Fmoc-protected piperidine derivative 4-5 in a shaking vessel was added 20 mL of a 20% v/v solution of piperidine in dimethylformamide. The resin suspension was shaken for 1 hour at 25° C. The shaking vessel was then drained and the resin was washed with dimethylformamide (two times), methylene chloride (two times), methanol (two times) and methylene chloride (two times). The resulting resin-bound secondary amine gave a positive result with the bromophenol blue staining test. The resin was used without drying.

Acylation with an Fmoc-protected Amino acid To 0.5 g (0.35 mmol/g, 0.35 mmol) of resin-bound secondary amine in 8 mL of methylene chloride was added 2 mmol of a Fmoc-protected amino acid (0.25 M) followed by 0.7 mL of N,N-diisopropylethylamine (0.5 M, 4 mmol, 0.51 g). This mixture was shaken until the acid dissolved before 0.93 g of PyBrop (0.25 M, 5 mmol) were added. The resulting mixture was shaken at 25° C. for 18 hours. The shaking vessel was drained and the resin was washed with methylene chloride (two times), methanol (two times), methylene chloride (two times), and methylene chloride (two times). The resulting resin-bound amide 4-6 gave a negative result with the bromophenol blue staining test. The resin was dried in vacuo.

N-Fmoc deprotection To 1.0 g (0.35 mmol/g, 0.35 mmol) of the resin bound Fmoc-protected amino acid 4-6 in a shaking vessel was added 20 mL of a 20% v/v solution of piperidine in dimethylformamide. The resin suspension was shaken for 1 hour at 25° C. The shaking vessel was then drained and the resin was washed with dimethylformamide (two times), methylene chloride (two times), methanol (two times) and methylene chloride (two times). The resulting resin-bound amine gave a positive result with the bromophenol blue staining tests. The resin was used without drying. Acylation A solution of 5 mmol of an acid (0.5 M) in 10 mL of dimethylformamide/ methylene chloride (1:1) was added to 0.32 g of resin-bound amine in a shaking vessel. A portion of 0.38 mL (2.5 mmol, 0.25 M) of DIC was then added. The resulting resin suspension was shaken at 25° C. for 21 hours. The shaking flask was then drained and washed with dimethylformamide (two times), methylene chloride (two times), methanol (two times) and again with methylene chloride (two times). The resulting resin-bound amino acid derivative 4-7 gave a negative result with the bromophenol blue test. This was died in vacuo.

The ligand 4-8 was cleaved from the resin by stirring the resin suspension in a mixture of 5 mL of methylene chloride and 5 mL of trifluoroacetic acid for 1.5 hours at 25° C. Boc-protecting groups, if present, were also cleaved during this procedure. The resin was filtered off and the solution concentrated in vacuo to give crude product 4-8. The crude compound was purified using preparative HPLC.

Scheme 5 below illustrates the synthetic route for construction of the spiro-piperidines of formula 5-10.

Scheme 5

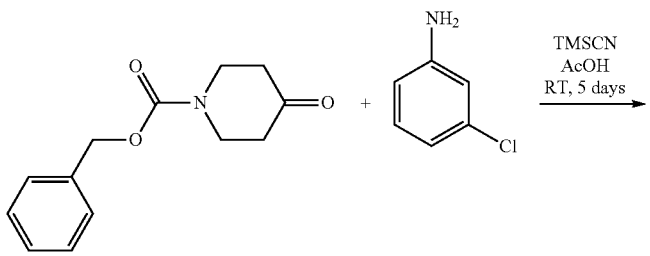

5-1

-continued
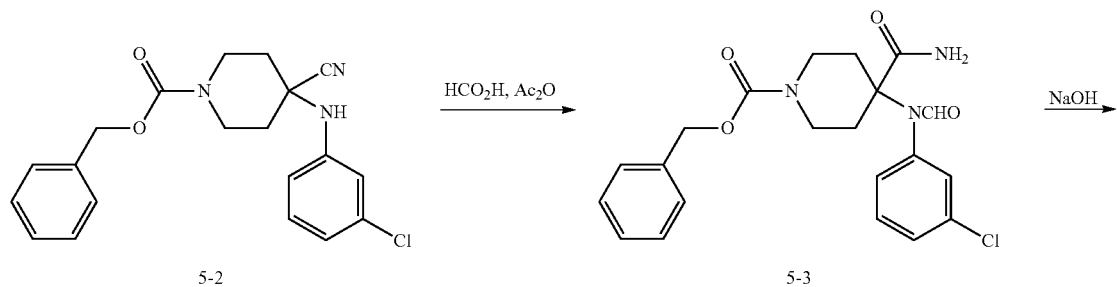
5-2    5-3
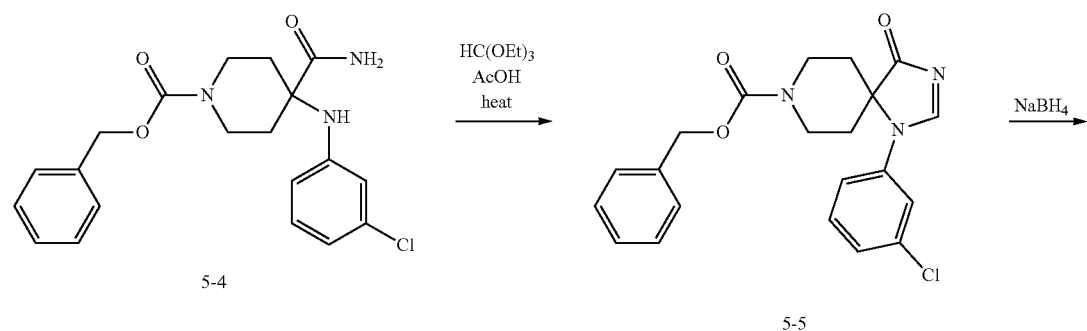
5-4    5-5
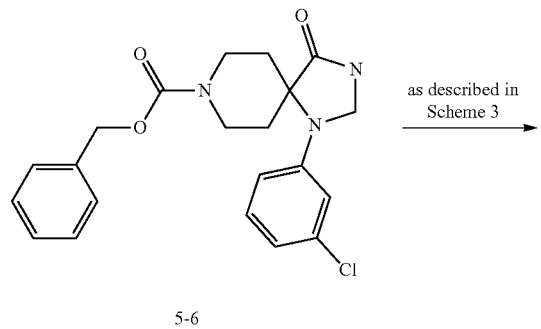
5-6
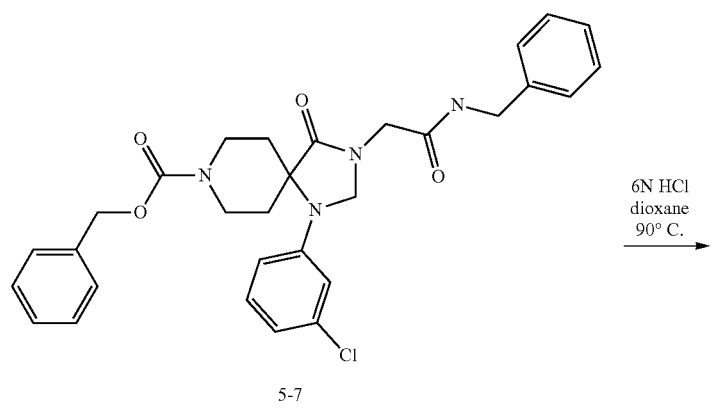
5-7

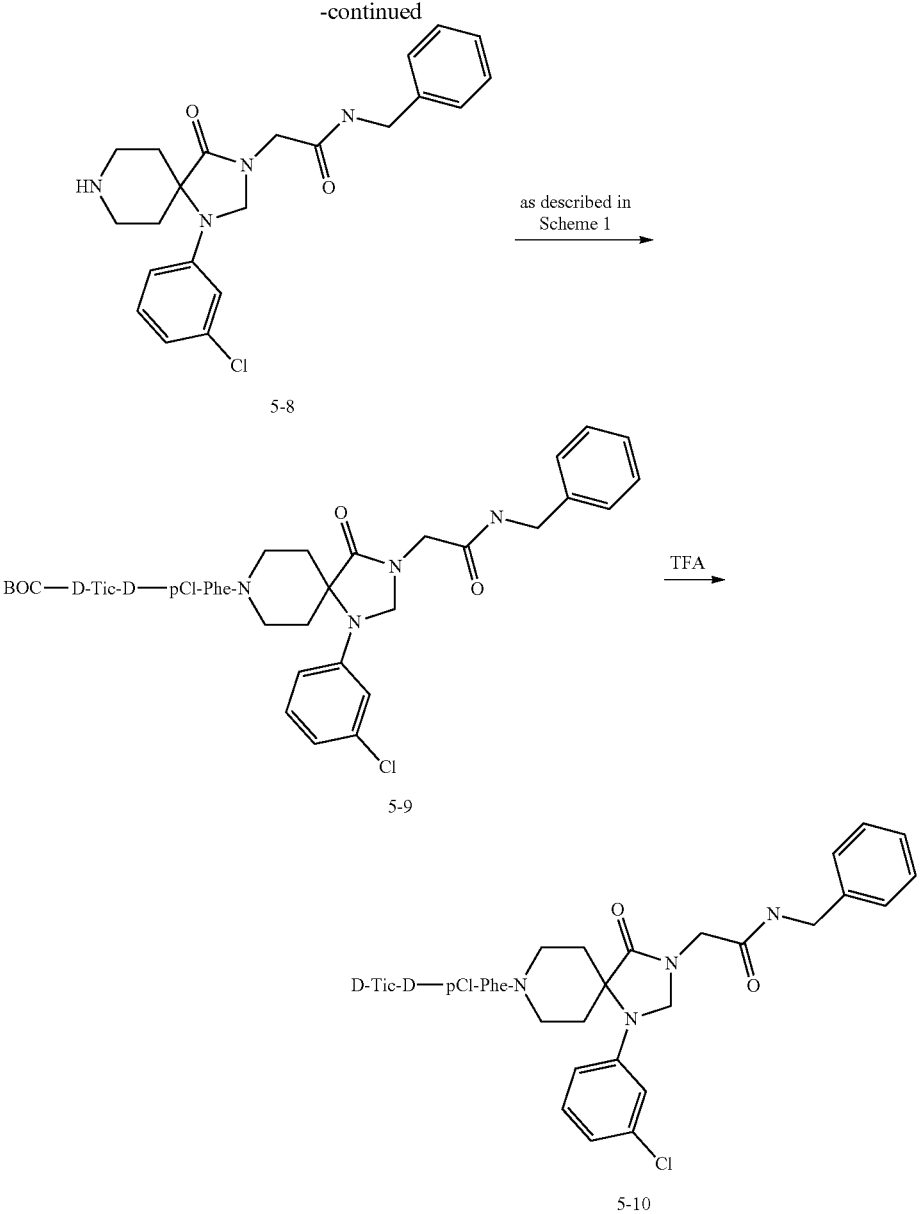

Method for Scheme 5

A solution of one equivalent each of ketone 5-1, 3-chloroaniline, and trimethylsilylcyanide in acetic acid was stirred at room temperature for five days. The reaction is poured into cold 7 N $NH_4OH$. The resulting precipitate was dried and purified by column chromatography to give compound 5-2. The synthetic methodology employed in the foregoing reaction is well known, for example, see *J. Org. Chem.* 1999, 64:5504-5510, which is hereby incorporated herein by reference.

Compound 5-2 was stirred in a 1:1 mixture of formic acid and acetic anhydride for six days at room temperature. The mixture was poured into dichloromethane and washed with 1N NaOH and brine, and dried over $MgSO_4$. Purification by column chromatography gave compound 5-3.

Compound 5-3 was dissolved in methanol and stirred overnight with a large excess of 10 N NaOH. After the methanol was removed by rotary evaporation, the aqueous residue was extracted with ethyl acetate. The organic extracts were dried over $MgSO_4$ and concentrated to give compound 5-4.

Compound 5-4 and one equivalent of triethyl orthoformate were refluxed in toluene and acetic acid for two days to give compound 5-5. The synthetic methodology employed in the foregoing reaction is well known, for example, see *Bioorg. Med. Chem. Lett.* 2006, 16:349-353, hereby incorporated herein by reference.

Compound 5-5 was treated with one equivalent of sodium borohydride in methanol to give compound 5-6, for example, using the procedure described in *Bioorg. Med. Chem. Lett.* 2006, 16:349-353.

Compound 5-6 was converted to compound 5-7 using the procedures described above for the conversion of 1-5 to 3-2 in Scheme 3 using benzylamine for the amine.

Compound 5-7 was dissolved in 1,4-dioxane. 6N hydrochloric acid was added and the reaction was heated at 90° C. for 3 hours. The solvents were evaporated and the residue was partitioned between ethyl acetate and sodium bicarbonate solution. The organic layer was dried over MgSO$_4$ and concentrated to give 5-8.

Compound 5-8 was converted to compound 5-9 using the procedures described in above for the conversion of 1-3 to 1-5 in Scheme 1. However, initial removal of the Boc protecting group is not necessary.

Compound 5-9 was stirred in a 1:1 mixture of dichloromethane and trifluoroacetic acid for one hour at room temperature. The reaction mixture was concentrated and purified by preparative HPLC to give the target compound 5-10.

Scheme 6 below illustrates a methodology for the synthesis of compounds of the invention that are derivatives of compounds of the class 4-6.

Scheme 6

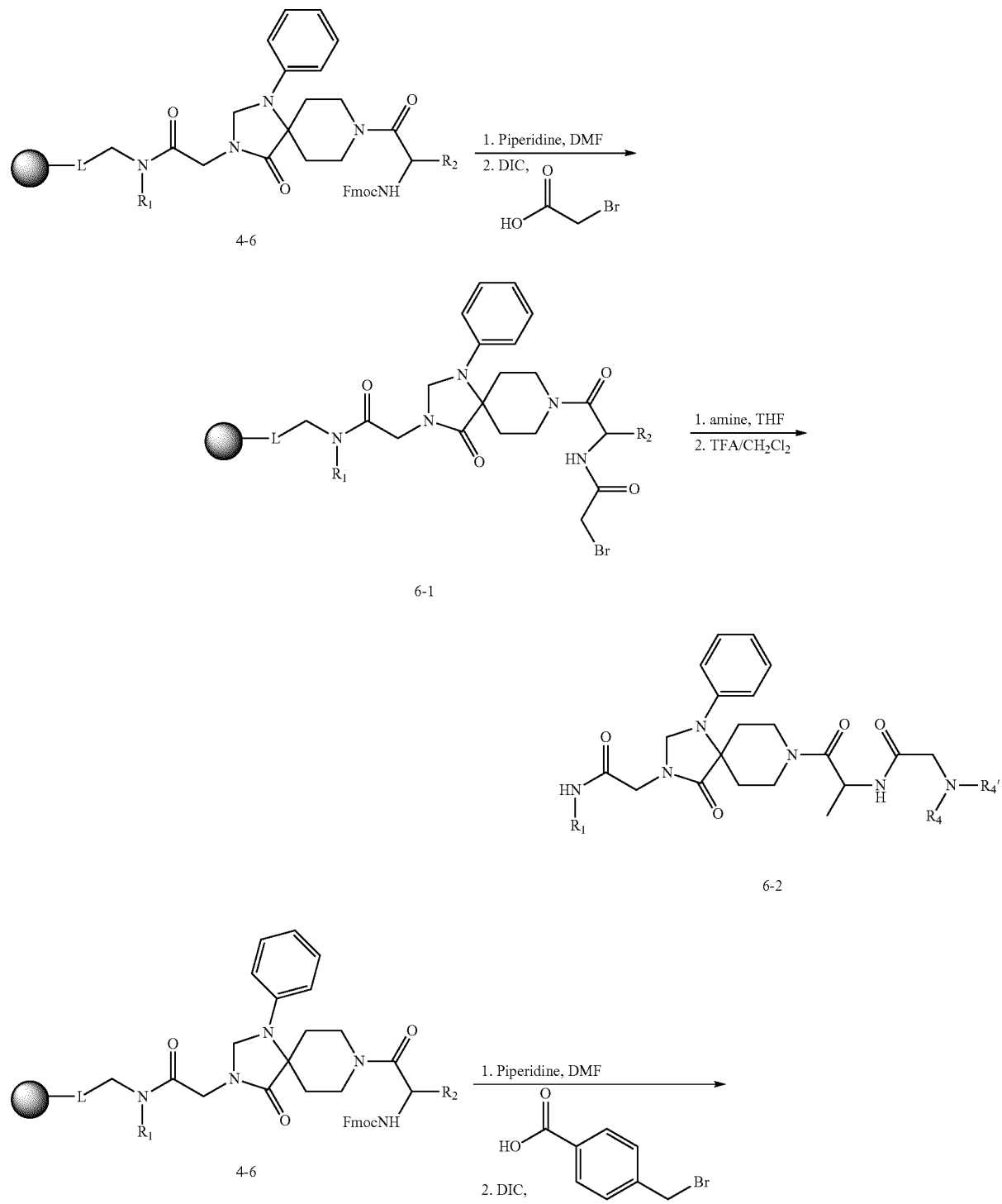

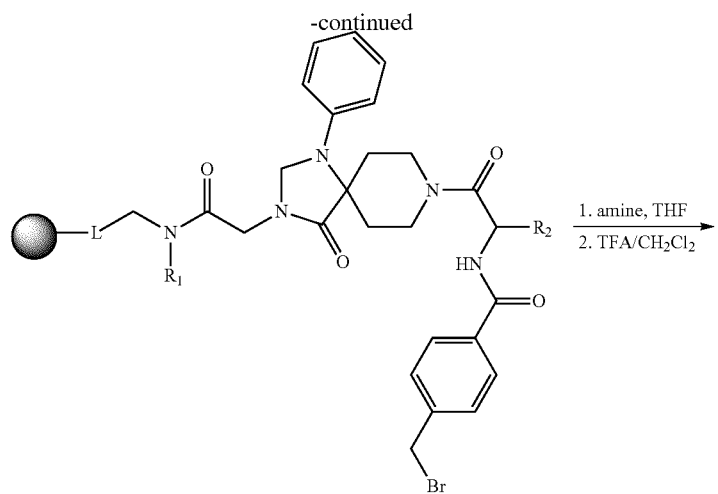
6-3
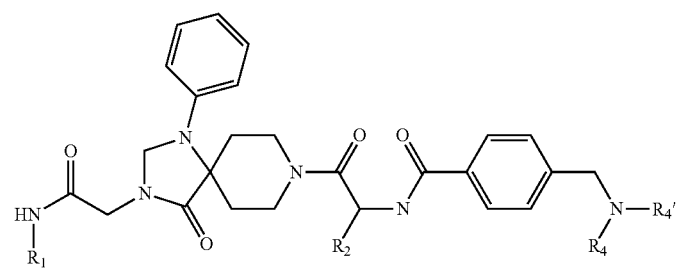
6-4
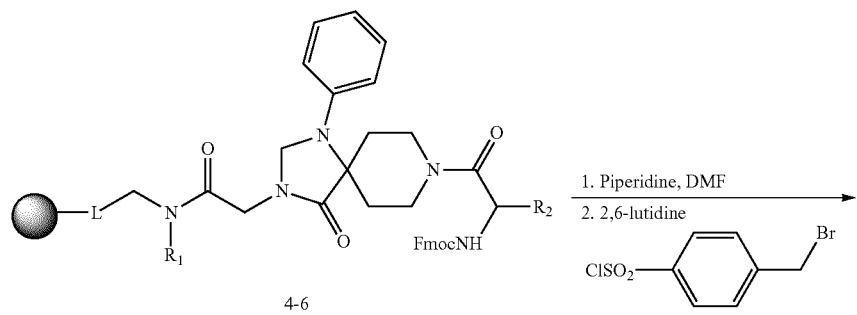
4-6
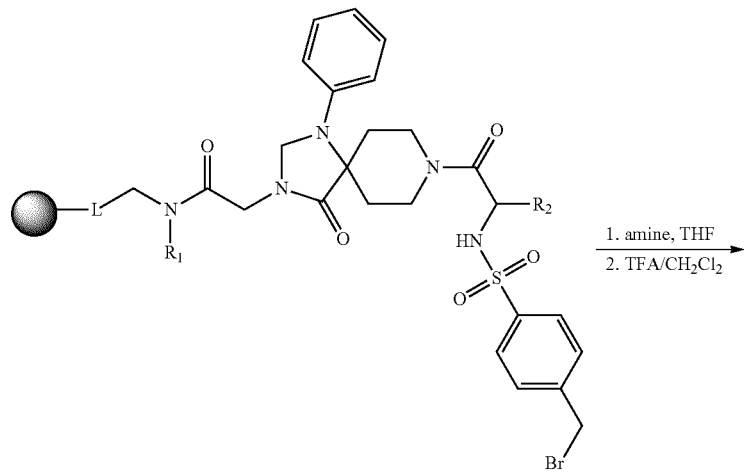
6-5

-continued

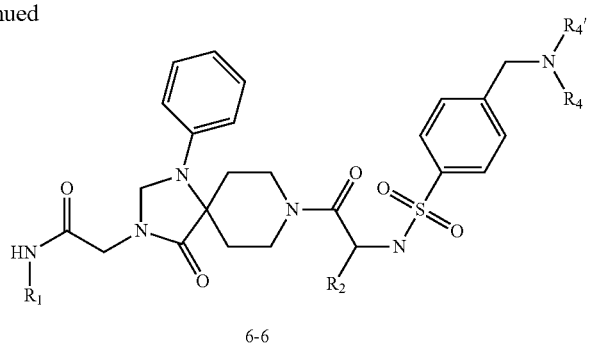

6-6

Method for Scheme 6

Fmoc deprotection To 1.0 g (0.35 mmol/g, 0.35 mmol) of the resin bound Fmoc-protected piperidine derivative 4-5 in a shaking vessel was added 20 mL of a 20% v/v solution of piperidine in dimethylformamide. The resin suspension was shaken for 1 hour at 25° C. The shaking vessel was then drained and the resin was washed with dimethylformamide (two times), methylene chloride (two times), methanol (two times) and methylene chloride (two times). The resulting resin-bound primary amine gave a positive result with the bromophenol blue staining test. The resin was used without drying.

Acylation with Bromoacetic Acid To 1.0 g (0.35 mmol/g, 0.35 mmol) of resin-bound primary amine a solution of 420 mg (3 mmol, 0.50 M) of bromoacetic acid in 6 mL of $CH_2Cl_2$/DMF (1:1) was added. A portion of 0.24 mL (1.5 mmol, 0.25 M) of DIC was then added. The resulting resin suspension was shaken at 25° C. for 18 hours. The shaking vessel was drained and the resin was washed with methylene chloride (two times), methanol (two times), methylene chloride (two times), methanol (two times), and methylene chloride (two times). The resulting resin-bound amide gave a negative result with the bromophenol blue staining test.

Acylation with 4-Bromomethylbenzoic acid To 1.0 g (0.35 mmol/g, 0.35 mmol) of the resin-bound primary amine was added a solution of 6 mmol (1.0 M) of 4-bromomethylbenzoic acid in 6 mL of $CH_2Cl_2$ followed by 0.47 mL (3.0 mmol, 0.50 M) of DIC. The resulting resin suspension was shaken at 25° C. for 18 hours. The shaking vessel was drained and the resin was washed with methylene chloride (two times), methanol (two times), methylene chloride (two times), methanol (two times), and methylene chloride (two times). The resulting resin-bound amide gave a negative result with the bromophenol blue staining test.

Sulfonylation with 4-Bromomethylphenylsulfonyl chloride To 1.0 g (0.35 mmol/g, 0.35 mmol) of the resin-bound primary amine in 3 mL of $CH_2Cl_2$ and 3 mL of 2,6-lutidine was added a solution of 6 mmol (1.0 M) of 4-bromomethylphenylsulfonyl chloride. The resulting resin suspension was shaken at 25° C. for 18 hours. The shaking vessel was drained and the resin was washed with methylene chloride (two times), methanol (two times), methylene chloride (two times), methanol (two times), and methylene chloride (two times). The resulting resin-bound sulfonamide gave a negative result with the bromophenol blue staining test.

N-Alkylation with an Amine To 0.5 g (0.35 mmol/g, 0.35 mmol) of the resin-bound bromomethyl-derivative 6-1, 6-3 or 6-5 in 6 mL of THF was added 6 mmol of an amine and the resin suspension was shaken at 25° C. for 20 hours. The shaking vessel was drained and the resin was washed with methylene chloride (two times), methanol (two times), methylene chloride (two times), methanol (two times), and methylene chloride (two times).

The ligands 6-2, 6-4 or 6-6 were cleaved from the resin by stirring the resin suspension in a mixture of 5 mL of methylene chloride and 5 mL of trifluoroacetic acid for 1.5 hours at 25° C. The resin was filtered off and the solution concentrated in vacuo to yield crude products 6-2, 6-4 or 6-6. The crude compounds were purified using preparative HPLC.

Scheme 7 below illustrates the synthetic route for construction of the spiro piperidines of formula 7-7.

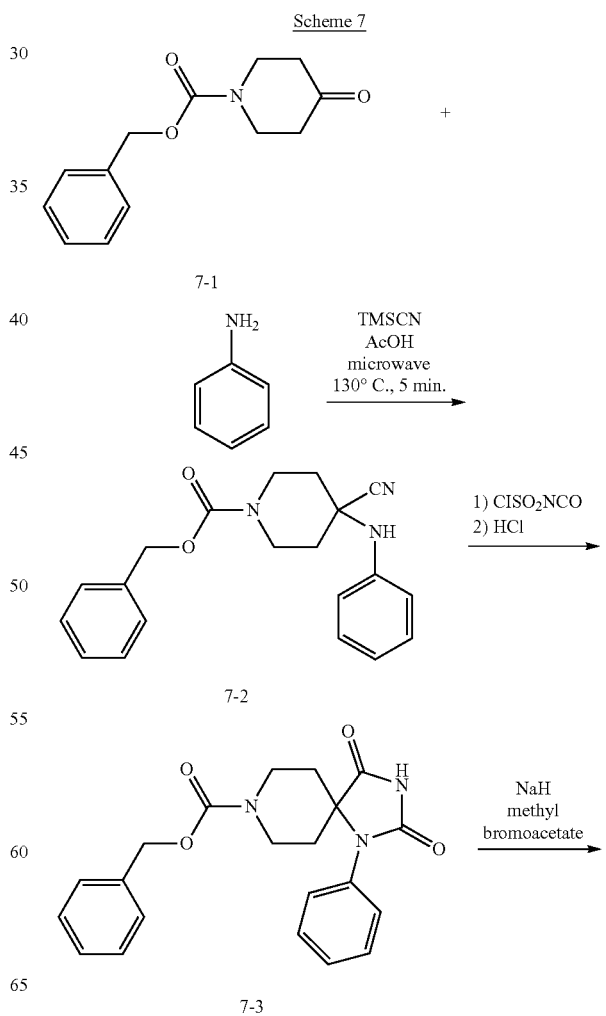

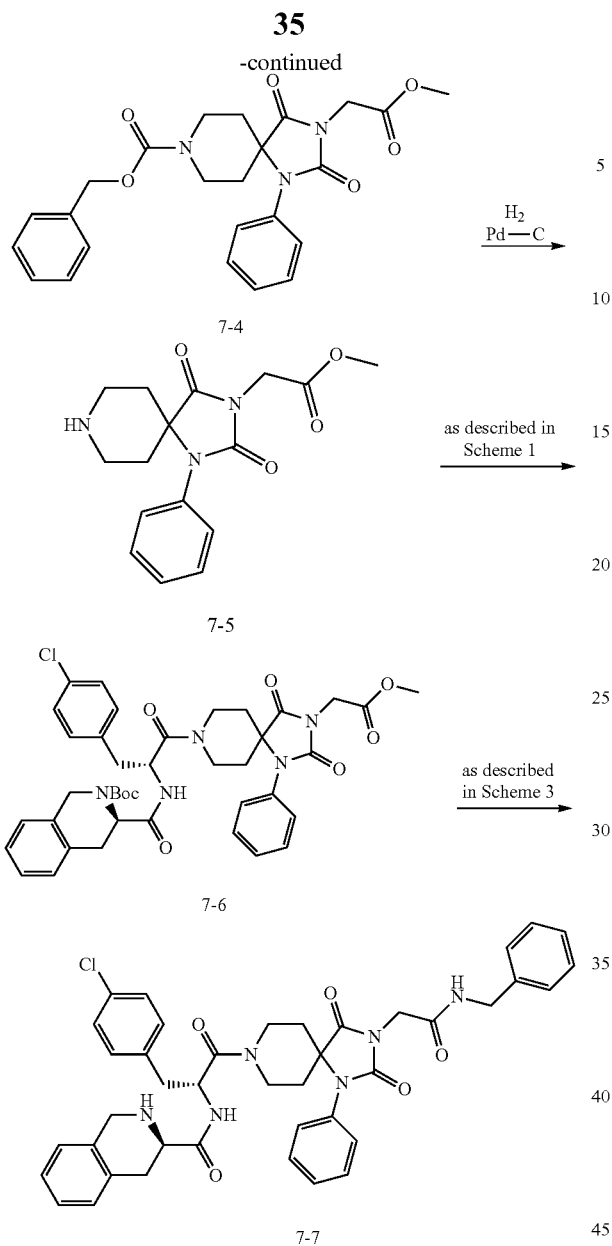
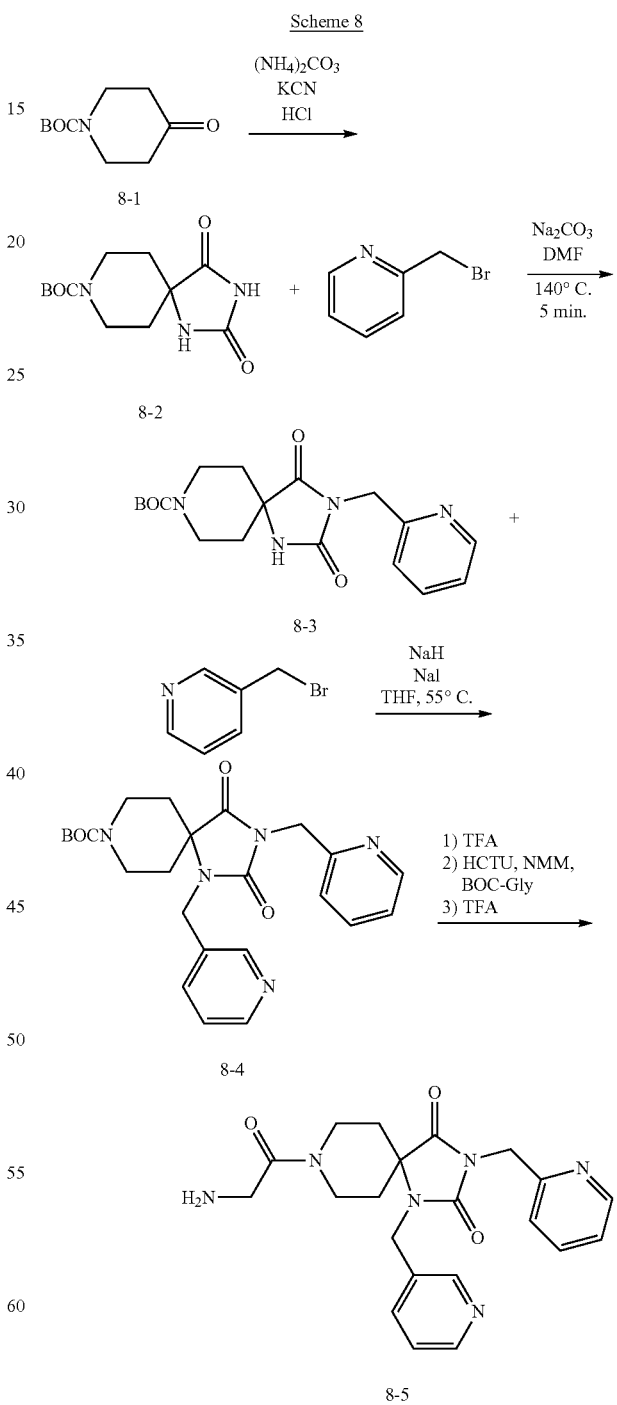

A solution of one equivalent each of ketone 7-1, aniline, and trimethylsilylcyanide in acetic acid was microwaved at 130° C. for 5 minutes. The reaction was poured into cold 7 N NH₄OH and then extracted with ethyl acetate. The ethyl acetate solution was dried and concentrated and the residue was purified by column chromatography to give compound 7-2.

One equivalent of chlorosulfonylisocyanate was added to compound 7-2 in dichloromethane. A white precipitate forms immediately. After 30 minutes the solvent was evaporated. 1N HCl was added to the residue along with a minimum amount of tetrahydrofuran required to get all the solids to dissolve. The solution was heated at 90° C. for one hour. After cooling the solids were filtered off, washed with water and toluene, and allowed to air dry to give compound 7-3. This procedure is described in J. Org. Chem. 1990, 55:4207, incorporated herein by reference.

Compound 7-4 was made using the procedure for making compound 1-3 in Scheme 1, except that tetrahydrofuran was used as the solvent.

Compound 7-4 was dissolved in ethanol and stirred with a catalytic amount of 10% palladium on carbon under a hydrogen atmosphere. Filtering off the catalyst and concentrating the filtrate gave compound 7-5.

Compound 7-5 was converted to compound 7-6 using the procedures described for the conversion of 1-3 to 1-5 in Scheme 1. However, the initial removal of the Boc protecting group is not necessary.

Compound 7-6 was converted to compound 7-7 using the procedures described above for the conversion of 1-5 to 3-2 in Scheme 3 using benzylamine for the amine.

Scheme 8 below illustrates the synthetic route for construction of the spiro piperidines of formula 8-5.

A mixture of Boc-piperidone (8-1) (1 eq.), 1N hydrochloric acid (1 eq.), ammonium carbonate (2 eq.) and potassium cyanide (2 eq.) were dissolved in 1:1 methanol:tetrahydrofuran and stirred in a stoppered flask at room temperature overnight. The volatile components were evaporated and the residue was slurried with water. The solids were filtered, washed with water and dried to give compound 8-2. This procedure is a modification of that described in *Organic Syntheses* 2005, 81:213, incorporated herein by reference.

A mixture of compound 8-2 (1 eq.), 2-(bromomethyl)pyridine hydrobromide (1 eq.), and sodium carbonate (4 eq.) in dimethylformamide were microwaved at 140° C. for 5 minutes. The resulting mixture was dissolved in ethyl acetate and washed with water, aqueous lithium chloride solution and brine. The organic layer was dried and concentrated to give compound 8-3.

Compound 8-3 was dissolved in tetrahydrofuran. Sodium hydride (4 eq.) was added. After 10 minutes a catalytic amount of sodium iodide and 1.2 equivalents of 3-(bromomethyl)pyridine hydrobromide were added. The mixture was heated at 55° C. under a $N_2$ atmosphere for 6 hours. After quenching with a small amount of methanol, the reaction mixture was concentrated and purified on silica gel eluting with methanol/dichloromethane to give compound 8-4.

Compound 8-4 was deprotected and coupled with Boc-glycine using the procedures described in Scheme 1 to give compound 8-5.

Scheme 9

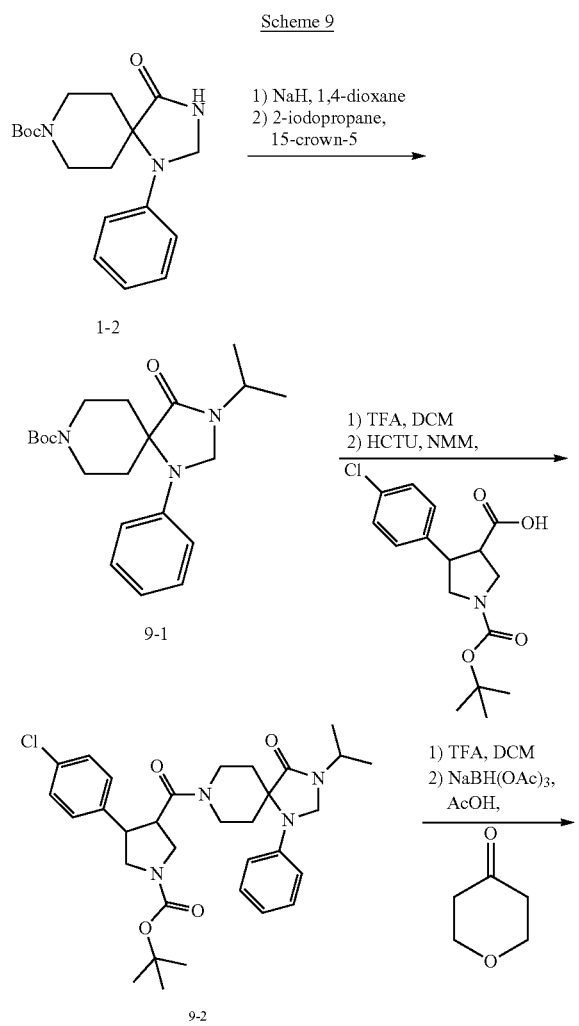

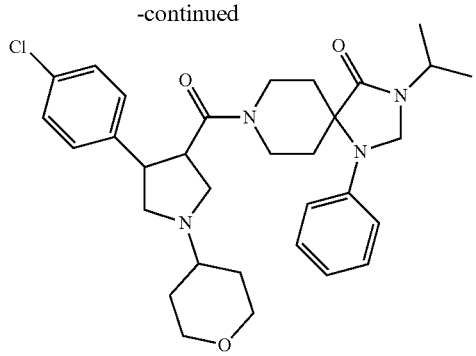

9-3

Method for Scheme 9

Compound 1-2 was dissolved in 1,4-dioxane and treated with 1.4 equivalents of sodium hydride. After stirring for 10 minutes at room temperature, 1.4 equivalents of 2-iodopropane and 1 drop of 15-crown-5 were added and the mixture was refluxed overnight. The solvent was evaporated and the residue was purified by silica gel chromatography to give product 9-1.

Compound 9-1 was treated by 50% TFA in DCM for 1 hour at room temperature. After removal of solvent the residue was neutralized by NMM in DCM. To this solution was added NMM (1 eq.), BOC-(±)-trans-4-(4-chlorophenyl)pyrrolidine-3-carboxylic acid (1.2 eq.) and HCTU (1 eq.). After stirring at room temperature for two hours the reaction mixture was washed with 1 N NaOH, dried, and concentrated to give crude product 9-2.

Compound 9-2 was treated by 50% TFA in DCM at room temperature overnight. After removal of the solvent the residue was dissolved in dichloromethane and washed with 6N NaOH, dried, and concentrated. The resulting material was dissolved in 1,2-dichloroethane. Tetrahydro-4H-pyran-4-one (2 equivalents), sodium triacetoxyborohydride (2 equivalents), and 1 drop of glacial acetic acid were added and the mixture was heated in a microwave oven for 20 minutes at 150° C. The resulting mixture was washed with aqueous sodium bicarbonate solution, concentrated, and purified by prep HPLC to give product 9-3.

5. Formulations and Administration

The compounds may be formulated by any means known in the art, including but not limited to tablets, capsules, caplets, suspensions, powders, lyophilized forms, gels, ophthalmic preparations and aerosols and may be mixed and formulated with buffers, binders, stabilizers, anti-oxidants and other agents known in the art. The compounds may be administered by any systemic, partially systemic or local means known in the art, including but not limited to intravenous injection, subcutaneous injection, administration through mucous membranes, oral administration, dermal administration, skin patches, aerosols, ocular, creams, gels and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed.

When formulated with a pharmaceutically acceptable carrier, the compound of this invention may be present in the pharmaceutical composition in a concentration from 0.1 to 99.5% (such as from 0.5 to 95%) by weight of the total mixture. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, such that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

In one preferred route of administration, compounds and pharmaceutical compositions of this invention are administered directly into the lung. Intrapulmonary administration may be performed by means of a metered dose inhaler, a device allowing self-administration of a metered bolus of a compound and pharmaceutical composition of this invention when actuated by a patient during inspiration. Both dry powder inhalation and nebulized aerosols may be employed. Thus it is possible and contemplated that compounds and pharmaceutical compositions of this invention may in one aspect be in a dried and particulate form. In one embodiment, the particles are between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the constructs may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

Nasal administration is another preferred route of administration, and in one embodiment a relatively higher proportion of the compound is delivered to the brain by means of nasal administration than is delivered if the compound is systemically administered, such as by injection. In part, nasal administration by-passes, or partially by-passes, the blood-brain barrier, permitting more effective dosing to the central nervous system. Nasal administration may be by means of a liquid spray, gel or powder. By "nasal administration" is meant any form of intranasal administration of any of the compounds and pharmaceutical compositions of this invention. Thus in one embodiment, compounds and pharmaceutical compositions of this invention include an aqueous solution, such as a solution including saline, citrate or other common excipients or preservatives, formulated for intranasal administration. In another embodiment, compounds and pharmaceutical compositions of this invention include a dry or powder formulation, formulated for intranasal administration. A preparation for nasal administration can take a variety of forms, such as for administration in nasal drops, nasal spray, gel, ointment, cream, powder or suspension. A variety of dispensers and delivery vehicles are known in the art, including single-dose ampoules, metered dose devices, atomizers, nebulizers, pumps, nasal pads, nasal sponges, nasal capsules, and the like. For dry powder delivery of the compound, it is possible and contemplated to use any of a number of devices, including but not limited to the DirectHaler Nasal device made by Direct-Haler NS, controlled particle dispersion devices made by Kurve Technology, and devices made by OptiNose AS. In general, the methods, teachings and devices disclosed in U.S. Pat. Nos. 6,648,848, 6,715,485, and 6,811,543 are incorporated here by reference. In any of the foregoing methods of nasal administration, any of a variety of strategies and compounds to increase permeability of the nasal mucosa may be employed, including but not limited to small-molecule permeation enhancers and tight junction-modulator peptides.

The pharmaceutical composition can be in a solid, semi-solid, or liquid form. For a solid form, the compound and other components may be mixed together by blending, tumble mixing, freeze-drying, solvent evaporation, co-grinding, spray-drying, and other techniques known in the art. A semi-solid pharmaceutical composition suitable for intranasal administration can take the form of an aqueous or oilbased gel or ointment. For example, the compound and other components can be mixed with microspheres of starch, gelatin, collagen, dextran, polylactide, polyglycolide or other similar materials that form hydrophilic gels. In one embodiment the microspheres can be internally loaded or coated with compound, and upon administration form a gel that adheres to the nasal mucosa. In another embodiment, the formulation is liquid, it being understood that this includes an aqueous solution, an aqueous suspension, an oil solution, an oil suspension, or an emulsion, depending on the physicochemical properties of the compound and other components.

For liquid formulations, excipients necessary or desirable for formulation, stability, and/or bioavailability are included in the pharmaceutical composition. Exemplary excipients include sugars (such as glucose, sorbitol, mannitol, or sucrose), uptake enhancers (such as chitosan), thickening agents and stability enhancers (such as celluloses, polyvinyl pyrrolidone, starch, and the like), buffers, preservatives, and/or acids and bases to adjust the pH. In one embodiment, an absorption promoting component is included in the pharmaceutical composition. Exemplary absorption promoting components include surfactant acids, such as cholic acid, glycocholic acid, taurocholic acid, and other cholic acid derivatives, chitosan and cyclodextrins.

The pharmaceutical composition may further include optional components, such as humectants, preservatives and the like. A humectant or moisturizing agent can be employed to decrease water loss from the pharmaceutical composition and optionally moisturize nasal mucosa. Exemplary humectants include hygroscopic materials such as glycerine, propylene glycol, polyethylene glycol, polysaccharides and the like. Preservatives may be employed, to prevent or limit bacteria and other microbial growth. One such preservative that may be employed is benzalkonium chloride, such as 0.05% benzalkonium chloride. Other preservatives include benzyl alcohol, methylparaben, propylparaben, butylparaben, chlorobutanol, phenethyl alcohol, phenyl mercuric acetate and the like.

The pharmaceutical composition may also include rheology modifying agents, such as for varying the viscosity of the pharmaceutical composition. Exemplary rheology modify agents include polyers and similar materials, such as sodium carboxymethyl cellulose, algin, carageenans, carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch, xanthan gum and combinations of the foregoing. Such agents may also and further service as bioadhesives, to extend the residence time of a compound of the invention within the nasal mucosa.

For certain applications, such as treatment of Crohn's disease or other inflammatory diseases or conditions of the bowel, it is desirable to deliver one or compounds of the invention into the intestinal tract, such as into the small intestine or the large intestine. This may be accomplished by the use of any of a variety of enteric coatings, pH-dependent soluble coatings, pH-lowering agents, absorption enhancement agents and the like. By way of example, published international application WO 02/072075 and U.S. Pat. No. 5,912,014 are incorporated by reference. The compound of this invention is preferably formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will rapidly disintegrate in the small intestine to release the active drug substance. One enteric coating solution that may be used includes cellulose acetate phthalate, and optionally other ingredients such as ammonium hydroxide, triacetin, ethyl alcohol, methylene blue, and purified water. Cellulose acetate phthalate is a polymer that has been used in the pharmaceutical industry for enterically coating individual dosage forms such as tablets and capsules, and is not soluble in water at a pH of less than about 5.8. Enteric coatings including cellulose acetate phthalate provide protection against the acidic environment of the stomach, but begin to dissolve in environment of the duodenum (pH of about 6-6.5), and are completely dissolved by the time the dosage form reaches the ileum (pH of about 7-8). In addition to cellulose acetate phthalate, other enteric coating materials are known and may be used with compounds of this invention, including without limitation hydroxypropylmethylethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach, and may be selected such that the enteric coating dissolves at a pH of approximately at least 6.0, more preferable at a pH of from about 6.0 to about 8.0. In one preferred aspect, the enteric coating dissolves and breaks down in the proximity of the ileum.

Any of a variety of permeation enhancers may be employed, to increase uptake in the intestines upon dissolution of the enteric coating. In one aspect, permeation enhancers increase either paracellular or transcellular transport systems. An increase in paracellular transport can be achieved by opening the tight junctions of the cells; an increase in transcellular transport can be achieved by increasing the fluidity of the cell membrane. Representative, non-limiting examples of such permeation enhancers include calcium chelators, bile salts (such as sodium cholate), and fatty acids. The compound of this invention may be in an enteric-coated individual dosage form that includes a fatty acid, such as for example oleate, palmitate, stearate, sodium caprate, or conjugated linoleic acid, in an enteric-coated capsule, to increase paracellular transport.

In one aspect, the individual dosage form, such as a tablet or capsule, optionally further includes common pharmaceutical binders such as povidone, diluents, glidants, fillers such as microcrystalline cellulose, lubricants such as magnesium stearate, disintegrants such as croscarmellose sodium, preservatives, colorants and the like in their usual known sizes and amounts. In some embodiments, peptides or polypeptides that act as substrates for intestinal proteases are further added.

Depending on the formulation and route of administration, if in an aqueous solution compounds and pharmaceutical compositions of this invention are appropriately buffered by means of saline, acetate, phosphate, citrate, acetate or other buffering agents, which are at any physiologically acceptable pH, generally from about pH 4 to about pH 8. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed.

The compounds and pharmaceutical compositions of this invention may be formulated for and administered by means of an injection, typically a deep intramuscular injection, such as in the gluteal or deltoid muscle, of a time release injectable formulation. In one embodiment, a compound or pharmaceutical composition of this invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In another embodiment a compound or pharmaceutical composition of this invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a construct of this invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of construct, the biodegradation rate of the polymer, and other factors known to those of skill in the art.

For ocular indications, compounds of this invention are formulated for administration in a form and by a method resulting in delivery of a compound of this invention to the eye or to a portion or part of the eye. In one aspect for the treatment of diseases of the eye, ophthalmic preparations for ocular administration including between about 0.0000001% and about 5% by weight solutions or suspensions of a compound of this invention in an acceptable ophthalmic formulation may be used. Emulsions, ointments, gels, ocular inserts, biodegradable ocular inserts, liposomes, microparticles, nanoparticles, nanospheres or ion pairing formulations may also be employed, which may, in some instances, result in increasing the ocular residence times of the compound of this invention.

In one aspect, an ophthalmic solution is employed, for direct administration to the eye, such as by way of eye drops. The ophthalmic solutions are preferably maintained in a pH range between about pH 3.5 to 9.0, and preferably about pH 6.5 and pH 7.2, with a suitable buffer. The pH may be adjusted by any known means, such as by use of HCl or NaOH. Buffers may include acetate, boric acid, sodium borate, potassium citrate, citric acid, sodium bicarbonate, TRIS, various mixed phosphate buffers (such as combinations of $Na_2HPO_4$, $NaH_2PO_4$ and $KH_2PO_4$) and mixtures thereof. Generally, buffers will be used in amounts ranging from about 0.05% to 2.5% (w/v), and preferably from about 0.1% to 1.5% percent; buffers should be as close to physiological ion concentrations as possible to minimize potential irritation but still maintain drug product pH over the shelf life of the product. The ophthalmic solutions employed in the present invention may be made from purified water, and in one aspect preferably from a physiological saline solution. Additional tonicity enhancing agents may be employed, including either ionic or non-ionic tonicity enhancing agents, or both. Ionic tonicity enhancing agents include alkali metal or earth metal halides, such as $CaCl_2$, KBr, KCl, LiCl, NaI, NaBr, NaCl, $Na_2SO_4$ or boric acid. Non-ionic tonicity enhancing agents include urea, glycerol, sorbitol, mannitol, propylene glycol, or dextrose. The aqueous solutions of the present invention are typically adjusted with tonicity agents to approximate an osmotic pressure equivalent to a 0.9% (w/v) solution of sodium chloride or a 2.5% solution of glycerol. However, tonicity ranges equivalent to between 0.7% and 1.5% NaCl are generally considered to be acceptable. The solutions can also contain conventional, pharmaceutically acceptable preservatives, stabilizers, cosolvents and/or penetration enhancers as well as viscoelastic substances included in artificial tear preparations. Pharmaceutically acceptable preservatives include quaternary ammonium compounds such as benzalkonium chloride, benzoxonium chloride or the like; alkyl-mercury salts of thiosalicylic acid such as thiomersal, phenylmercuric nitrate, phenylmercuric acetate or phenylmercuric borate; sodium perborate; sodium chlorite; parabens, such as methylparaben or propylparaben; alcohols such as chlorobutanol, benzyl alcohol or phenyl ethanol; guanidine derivatives such as chlorohexidine or polyhexamethylene biguanide; sorbic acid; boric acid; or peroxide forming preservatives, or combinations of two or more of the foregoing. Pharmaceutically acceptable antioxidants and chelating agents may be used including various sulphites (such as sodium metabisulphite, sodium thiosulphate, sodium bisulfite, or sodium sulfite), a-tocopherol, ascorbic acid, acetylcysteine, 8-hydroxyquinolome, antipyrine, butylated hydroxyanisole or butylated hydroxytoluene, EDTA, and others. Cosolvents such as alcohols and others may also be used. Various substances can also be used to enhance formulation stability, such as cyclodextrins.

Penetration enhancers may be employed in ophthalmic solutions, including compounds such as surfactants, certain organic solvents such as dimethylsulphoxide and other sulphoxides, dimethylacetamide and pyrrolidine, certain amides of heterocyclic amines, glycols (e.g. propylene glycol), propylene carbonate, oleic acid, alkylamines and derivatives, various cationic, anionic and nonionic surfactants, amphoteric surfactants and the like. Additional penetration enhancers that may be employed include cetylpyridinium chloride, ionophores such as lasalocid, benzalkonium chloride, polysorbates such as polysorbate 20 (Tween® 20), parabens, saponins, various polyoxyethylene ether compounds such as Brij® 35, Brij® 78 or Brij® 98, ethylenediaminetetraacetic acid (EDTA), bile salts, and bile acids (such as sodium cholate, sodium taurocholate, sodium glycodeoxycholate, sodium taurodeoxycholate, taurocholic acid, chenodeoxycholic acid and ursodeoxycholic acid), capric acid, azone, fucidic acid, hexamethylene lauramide, saponins, hexamethylene octanamide, and decylmethyl sulfoxide. Ion pairing formulations utilizing charged excipients or counter ions to shield/neutralize charged groups on drug molecules may also be employed to lower the lipophilicity of the compound to increase corneal penetration. These formulations include but are not limited to ions such as sorbic acid, boric acid and maleic acid, among other charged ion pairing agents.

Viscosity enhancers or lubricants may be employed as necessary or appropriate. In one aspect, the viscosity enhancer includes a water soluble polymer, such as polyols, including polyvinyl alcohol, a polyethylene glycol, or combinations of water soluble polymers. In one aspect, polyethylene glycol 300 or 400 is employed. The contents of water soluble polymer may be between about 0.25% and about 4.0% (w/v). Thus an ophthalmic solution can include, by way of example, 1% of polyvinyl alcohol, 1% of polyethylene glycol 300 or 400, or both. Other polyols may be employed, including glycerol, glycerin, polysorbate 80, propylene glycol, ethylene glycol, povidone, and polyvinylpyrrolidone. Other lubricants, sometimes also called tear substitutes, may also be employed, including cellulose derivatives such hydroxypropyl methyl cellulose, carboxymethyl cellulose sodium, hydroxypropyl cellulose, hydroxyethyl cellulose, and methyl cellulose; dextrans such as dextran 70; water soluble proteins such as gelatin; carbomers such as carbomer 934P, carbomer 941, carbomer 940 and carbomer 974P; and gums such as HP-guar, xanthan gum or combinations thereof. Other viscosity enhancers that can be employed include polysaccharide compounds, such as sulfated or non-sulfated glycosaminoglycan compounds. In one aspect, the polysaccharide compound is a non-sulfated glycosaminoglycan such as hyaluronic acid or a pharmaceutically acceptable salt thereof, such as sodium hyaluronate. Any commercially available molecular weight range of hyaluronic acid or salts thereof may be employed. From about 0.05% to about 0.4% (w/v) of hyaluronic acid or a salt thereof may be employed in an ophthalmic solution. In another aspect, the polysaccharide compound is a non-sulfated glycosaminoglycan such as dextran. In yet another aspect, the polysaccharide is a sulfated glycosaminoglycan such as chondroitin sulfate.

Semi-solid formulations may be employed for ophthalmic delivery to increase corneal residence times of drug molecules. Ointments containing polyethylene glycols, lanolin alcohols, ozokerite, ceresin, microcrystalline wax, surfactants, preservatives, sorbitan monolaurate, white petrolatum and light liquid petrolatum (mineral oil) or other petrolatum like bases may be used. Aqueous or non-aqueous suspensions may also be used. For hydrophilic compounds, suspensions using pharmaceutically acceptable oils or petrolatum may be used. Suspensions may contain microspheres or microparticulates, nanoparticulates, mucoadhesive particles, viscosity increasing agents, surfactants and other agents. Mucoadhesive compounds include synthetic polymers, such as polyacrylic acid and polycarbophil; biopolymers such as hyaluronic acid or sodium carboxy methylcellulose (CMC); polyanionic polymers such as polyacrylic acid (PAA); polyacrylic acids such as Carbopol® 934P, polycarbophil, and CMC or PAA with Pluronic® polyoxalkylene ethers; or polycationic polymers such as chitosan. Emulsions (oil in water or water in oil), including microemulsions, may also be employed that are composed of pharmaceutically acceptable oils together with one or more of viscosity increasing agents, preservatives, cosolvents, surfactants and other agents. Pharmaceutically acceptable oils include mineral oils and organic oils, including oils comprising medium chain or long chain saturated or unsaturated fatty acids or esters thereof. Pharmaceutically acceptable oils thus include any of a range of medium chain triglycerides, as well as oils such as almond oil, castor oil, cottonseed oil, glycerin (glycerol), peanut oil, mineral oil, polyethylene glycol, poppyseed oil, propylene glycol, safflower oil, sesame oil, soybean oil, olive oil and vegetable oil. A surfactant such as a polyoxyethylene alkyl ether, polyoxyl castor oil, tyloxapol, alkyl aryl ether sulfonate, lecithin, sorbitan esters, glyceryl monostearate, cetyl alcohol, octoxynol-9, nonoxynol-9, polyoxyethylene stearates, polyoxyethylene sorbitan fatty acid esters such as polysorbate 20, 60 and 80 or others may also be employed. Aqueous gels, often comprised of polymers such as polyvinyl alcohol (PVA), polyacrylamide, poloxamer, hydroxypropyl methylcellulose (HPMC), carbomer, polymethylvinylether maleic anhydride, and hydroxypropyl ethylcellulose may also be used. Hydrogels containing swellable, water insoluble polymers may be utilized containing polymers such as poly (acrylic acid), poly(acrylic acids), poly(acrylamide), and ethylene maleic anhydride, and chemically or thermally-treated gelatins. Ocular inserts, liposomes, discomes, niosomes, dedrimers, nanosuspensions, nanoparticles and microparticles may also be used to provide a controlled release of the drug. Liposomes and other controlled release agents may be positively charged to increase residence times through ionic interactions with the negatively charged corneal surface. Nanoparticles may be composed of biodegradable polymers such as polyactides (PLAs), polycyano acrylates, poly (D,L-lactides), and natural polymers such as chitosan, gelatin, sodium alginate, albumin and others.

Combination ophthalmic solutions may be employed, including specifically solutions including more than one active pharmaceutical ingredient. In one aspect, a non-steroidal anti-inflammatory drug (NSAID) is employed in combination with a compound of this invention. NSAIDs suitable for use in combination ophthalmic solutions include agents, their esters and pharmaceutically acceptable salts thereof that inhibit the cyclooxygenase (COX)-1 and/or -2 enzyme, including but not limited to propionic acid compounds such as naproxen, flurbiprofen, oxaprozin, ibuprofen, ketoprofen, fenoprofen; ketorolac tromethamine; acetic acid derivatives such as sulindac, indomethacin, and etodolac; phenylacetic acids such as diclofenac, bromfenac, and suprofen; arylacetic prodrugs such as nepafenac, and amfenac; salicyclic acids, such as aspirin, salsalate, diflunisal, choline magnesium trisalicylate; para-aminophenol derivatives such as acetaminophen; naphthylalkanones such as nabumetone; enolic acid derivatives such as piroxicam and meloxicam; femanates such as mefenamic acid, meclofenamate and flufenamic acid; pyrroleacetic acids such as tolmetin; and pyrazolones such as phenylbutazone; and COX-2 selective inhibitors such as celecoxib, valdecoxib, parecoxib, etoricoxib, and luaricoxib. The ophthalmic solutions may additionally comprise other active ingredients, including, but not limited to, vasoconstrictors, anti-allergenic agents, anti-infectives, steroids, anesthetics, anti-inflammatories, analgesics, dry eye treatment agents (e.g. secretagogues, mucomimetics, polymers, lipids, antioxidants), and the like, or be administered in conjunction (simultaneously or sequentially) with pharmaceutical compositions comprising other active ingredients, including, but not limited to, vasoconstrictors, anti-allergenic agents, anti-infectives, steroids, anesthetics, anti-inflammatories, analgesics, dry eye treatment agents (e.g. secretagogues, mucomimetics, polymers, lipids, antioxidants), and the like.

5.1 Pharmaceutically Effective Amount

In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired effect. This may readily be determined by one of ordinary skill in the art through means such as pharmacokinetic studies, plasma half-life studies, dose escalation studies, and the like. Thus a pharmaceutically effective amount includes an amount of a compound or pharmaceutical composition of this invention that is sufficient to induce the desired effect.

In general, the compounds of this invention are highly active, with dose responses as low as 0.01 µg/kg, generally with optimal or peak dose responses between about 0.01 µg/kg and 25 µg/kg, depending on the specific compound and the route of administration. For example, the compound can be administered at 0.01, 0.05, 0.1, 0.5, 1, 5, 10, 50, 100, or 500 µg/kg body weight, depending on specific compound selected, the desired response, the route of administration, the formulation and other factors known to those of skill in the art. Conventional dose response studies and other pharmacological means may be employed to determine the optimal dose for a desired effect with a given compound, given formulation and given route of administration.

5.2 Clinical Indications and Applications

In a broad aspect, compounds of this invention may be utilized, therapeutically or prophylactically, for any melanocortin receptor-mediated disorder, condition, disease or syndrome. Certain of the compounds of this invention are agonists, antagonists, mixed agonist-antagonists, inverse agonist or antagonists of inverse agonists with respect to one or more melanocortin receptors, and thus utility depends on the specific melanocortin receptor-mediated disorder, condition, disease or syndrome for which therapeutic or prophylactic treatment is desired.

In one aspect, compounds of this invention may be utilized for treatment of a mammalian patient with circulatory shock, including administration to the patient with circulatory shock of a therapeutically effective amount of a pharmaceutical composition including a compound of this invention or a pharmaceutically acceptable salt thereof. Administering may include intravenous, intraarterial, subcutaneous, intramuscular, intraperitoneal, intrathoracic, intrathecal, intraosseous, intracranial, intracerebroventricular, or intracerebral administration. Circulatory shock may include hypovolemic shock, cardiogenic shock, vasodilatory shock, septic shock, hemorrhagic shock, traumatic shock, or neurogenic shock. Hemorrhagic shock may include hypovolemic shock secondary to trauma, aortic dissection, ruptured aneurysm, and stroke.

In another aspect, compounds of this invention may be utilized for limiting hemorrhagic shock in a mammal, preferably a person, with bleeding secondary to trauma, including administering a therapeutically effective amount of a pharmaceutical composition including a comound of this invention or a pharmaceutically acceptable salt thereof. This may be done by establishing an intravenous line in a person with bleeding secondary to trauma, wherein administering includes intravenous administration. In one aspect the person is to be transported to a trauma care facility and the intravenous line is established prior to transport of the person to the trauma care facility. In a related aspect, intravenous administration of the pharmaceutical composition is initiated prior to transport of the person to the trauma care facility. In another aspect, intravenous administration of the pharmaceutical composition is done during transport of the person to the trauma care facility. In another aspect, the pharmaceutical composition is administered concurrent with or prior to the onset of metabolic acidosis. The composition may be in an aqueous solution. Intravenous administration may comprise intravenous administration of a bolus of the pharmaceutical composition. In another aspect, administering for this method may include intravenous, intraarterial, subcutaneous, intramuscular, intraperitoneal, intrathoracic, intrathecal, intraosseous, intracranial, intracerebroventricular, or intracerebral administration.

In another aspect, compounds of this invention may be utilized for limiting injury in a person with spinal cord injury, including intrathecal administration of a therapeutically effective amount of a pharmaceutical composition including a compound of this invention or a pharmaceutically acceptable salt thereof. In this aspect, intrathecal administration includes administration proximal the site of spinal cord injury.

In another aspect, compounds of this invention may be utilized for reducing excess extracellular fluid in a subject undergoing hemodialysis, such as by administering a pharmaceutical composition including an agonist compound of this invention to the subject in a therapeutically effective amount to maintain blood pressure during hemodialysis, and reducing excess extracellular fluid in the subject during hemodialysis. The agonist compound of this invention may be a melanocortin receptor agonist with binding at human MC1-R, as determined by Ki values, at least ten times as great as the binding at human MC4-R. The agonist compound may further be a melanocortin receptor agonist wherein the binding at human MC1-R, as determined by Ki values, is more than ten times as great as the binding at human MC4-R.

In another aspect, compounds of this invention may be utilized for preventing hypotension in a subject during hemodialysis, including administering a pharmaceutical composition including an agonist compound of this invention to the subject in a therapeutically effective amount to maintain blood pressure during hemodialysis, whereby excess extracellular fluid in the subject may be removed during hemodialysis without inducing hypotension. The agonist compound of this invention may be a melanocortin receptor agonist with binding at human MC1-R, as determined by Ki values, at least ten times as great as the binding at human MC4-R. The agonist compound may further be a melanocortin receptor agonist wherein the binding at human MC1-R, as determined by Ki values, is more than ten times as great as the binding at human MC4-R.

In another aspect, compounds of this invention may be utilized for limiting hypertension between hemodialysis treatments in a subject undergoing hemodialysis by reducing excess extracellular fluid in the subject, by administering a pharmaceutical composition including a compound of this invention or a pharmaceutically acceptable salt thereof to the subject in a therapeutically effective amount to inhibit hypotension secondary to extracellular fluid reduction during hemodialysis, and reducing excess extracellular fluid in the subject during hemodialysis, whereby the removal of excess extracellular fluid in the subject limits hypertension between hemodialysis treatments.

In another aspect, compounds of this invention may be utilized for treatment of a mammalian patient with inflammatory disease, including administration to the patient with an inflammatory disease of a therapeutically effective amount of a pharmaceutical composition including a compound of this invention or a pharmaceutically acceptable salt thereof. The inflammatory disease may be osteoarthritis, rheumatoid arthritis, septic arthritis, gout and pseudogout, juvenile idiopathic arthritis, Still's disease, ankylosing spondylitis, as psoriatic arthritis, reactive arthritis, inflammatory bowel disease, Crohn's disease, or ulcerative colitis. Alternatively, the inflammatory disease may be secondary to a form of inflammatory bowel disease, including Crohn's disease, ulcerative colitis, collagenous colitis, lymphocytic colitis, ischemic colitis, diversion colitis, Behget's syndrome, infective colitis and indeterminate colitis, an autoimmune disease, including systemic lupus erythematosus, Sjogren's syndrome, scleroderma, rheumatoid arthritis and polymyositis, an endocrine system disease including diabetes mellitus type 1, Hashimoto's thyroiditis, and Addison's disease, a dermatologic disease including pemphigus vulgaris, a hematologic disease including autoimmune hemolytic anemia, a neural disease including multiple sclerosis, a chronic obstructive pulmonary disease, including chronic bronchitis, emphysema, pneumoconiosis, and pulmonary neoplasms, an upper or lower airway disease or disorder, including allergic asthma, non-allergic asthma, allergic rhinitis, vasomotor rhinitis, allergic conjunctivitis, and non-allergic conjunctivitis, an airway disease related to external toxins or substances, including pneumoconiosis, coalworkers pneumoconiosis, asbestosis, silicosis, bauxite fibrosis, berylliosis, or siderosis, byssinosis andhypersensitivity pneumonitis (farmer's lung or bird fanciers lung), or a transplant-related condition or syndrome. Administering may include intravenous, intraarterial, subcutaneous, intramuscular, intraperitoneal, intrathoracic, intrathecal, intraosseous, intracranial, intracerebroventricular, or intracerebral administration. In one aspect, administration comprises intravenous administration of a bolus of the pharmaceutical composition in an aqueous solution.

In another aspect, the inflammatory condition results from or is related to chronic obstructive pulmonary disease (COPD), also known as chronic obstructive airway diseases, including but not limited to diseases characterized by the pathological limitation of airflow in the airway that is not fully reversible, such as for example chronic bronchitis, emphysema, pneumoconiosis, pulmonary neoplasms and other lung disorders. Other inflammatory conditions include upper or lower airway diseases and disorders, such as allergic asthma, non-allergic asthma, allergic rhinitis, vasomotor rhinitis, allergic conjunctivitis, non-allergic conjunctivitis, and the like, as well as airway diseases related to external toxins or substances, such as various forms of pneumoconiosis (coalworker's pneumoconiosis, asbestosis, silicosis, bauxite fibrosis, berylliosis, or siderosis), byssinosis or hypersensitivity pneumonitis (farmer's lung or bird fancier's lung).

In yet another aspect, the inflammatory condition results from or is related to some form of transplant-related condition or syndrome, such as graft-versus-host disease, hyperacute rejection, acute rejection, or chronic rejection. Graft-versus-host disease is a common complication of allogeneic bone marrow transplantation, but can occur with other transplantations, and particularly those with T cells present in the graft, either as contaminants or intentionally introduced. Hyperacute, acute or chronic rejection can occur with bodily organs such as kidneys, liver, pancreas, spleen, uterus, heart or lungs, as well as transplantation of bone, cornea, face, hand, penis or skin. In one embodiment, a pharmaceutical composition including a compound of this invention is given prophylactically to limit or prevent a transplant-related condition or syndrome, such as immediately before, during or after transplantation of a bodily fluid, organ or part. In another embodiment, the bodily fluid, organ or part being transplanted is perfused with a solution of a pharmaceutical composition including a compound of this invention. In yet another embodiment, a compound of this invention is administered in conjunction with, combination with or series with one or more other agents for transplant rejection, such as calcineurin inhibitors including cyclosporin or tacrolimus, mTOR inhibitors including sirolimus or everolimus, anti-proliferatives including azathioprine or mycophenolic acid, corticosteroids including prednisolone or hydrocortisone, antibodies such as monoclonal anti-IL-2Rα receptor antibodies, basiliximab or daclizumab, or polyclonal anti-T-cell antibodies such as anti-thymocyte globulin or anti-lymphocyte globulin.

In another aspect, compounds of this invention may be utilized for treatment of a mammalian patient with increased cytokine expression, including administration to the patient with increased cytokine expression of a therapeutically effective amount of a pharmaceutical composition including a compound of this invention or a pharmaceutically acceptable salt thereof. The increased cytokine expression may be secondary to circulatory shock, ischemia, or reperfusion injury. Administering may comprise intravenous, intraarterial, subcutaneous, intramuscular, intraperitoneal, intrathoracic, intrathecal, intraosseous, intracranial, intracerebroventricular, or intracerebral administration. Administering may additionally comprise intravenous administration of a bolus of the pharmaceutical composition in an aqueous solution.

In another aspect, the compounds of this invention may be utilized for prophylactic treatment of a mammalian patient at risk of increased cytokine expression, including administration to the patient at risk of increased cytokine expression of a therapeutically effective amount of a pharmaceutical composition including a compound of this invention or a pharmaceutically acceptable salt thereof.

In another aspect, compounds of this invention may be utilized for protecting mammalian tissue or organs from the deleterious effects of ischemia, including the step of administering a pharmaceutical composition including a compound of this invention or a pharmaceutically acceptable salt thereof to a mammalian patient in a therapeutically amount effective sufficient to reduce the deleterious effects of ischemia, wherein the patient's mean arterial pressure increases less than about 10%.

In another aspect, compounds of this invention may be utilized for preventing or reducing ischemia-reperfusion injury to a mammalian tissue or organ, including the step of administering a pharmaceutical composition including a compound of this invention or a pharmaceutically acceptable salt thereof to a mammalian patient at risk for ischemia-reperfusion injury in a therapeutically effective amount sufficient to prevent or reduce ischemia-reperfusion injury.

In another aspect, compounds of this invention may be utilized for preventing or treating ocular inflammatory disease. Ocular inflammatory disease is a disease of the eye including dry eye disease, which affects approximately 10-20% of the population. This disease progressively affects larger percentages of the population as it ages, with the majority of these patients being women. In addition, almost everyone experiences ocular irritation, or the symptoms and/or signs of dry eye as a condition, from time to time under certain circumstances, such as prolonged visual tasking (e.g., working on a computer), being in a dry environment, using medications that result in ocular drying and so on. In individuals suffering from dry eye, the protective layer of tears that normally protects the ocular surface is compromised, a result of insufficient or unhealthy production of one or more tear components. This can lead to exposure of the surface of the eye, ultimately promoting desiccation and damage of surface cells. Signs and symptoms of dry eye include but are not limited to keratitis, conjunctival and corneal staining, redness, blurry vision, decreased tear film break-up time, decreased tear production, tear volume, and tear flow, increased conjunctival redness, excess debris in the tear film, ocular dryness, ocular grittiness, ocular burning, foreign body sensation in the eye, excess tearing, photophobia, ocular stinging, refractive impairment, ocular sensitivity, and ocular irritation. Patients may experience one or more of these symptoms. The excess tearing response may seem counter-intuitive, but it is a natural reflex response to the irritation and foreign body sensation caused by the dry eye. Some patients may also experience ocular itching due to a combination of ocular allergy and dry eye symptoms.

There are many possible variables that can influence a patient's signs or symptoms of dry eye including levels of circulating hormones, various autoimmune diseases (e.g. Sjogren's syndrome and systemic lupus erythematosus), ocular surgeries including PRK or LASIK, many medications, environmental conditions, visual tasking such as computer use, ocular fatigue, contact lens wear, and mechanical influences such as corneal sensitivity, partial lid closure, surface irregularities (e.g. pterygium), and lid irregularities (e.g. ptosis, entropion/ectropion, pinguecula). Environments with low humidity, such as those that cause dehydration, can exacerbate or cause dry eye symptoms, such as sitting in a car with the defroster on or living in a dry climate zone. In addition, visual tasking can exacerbate symptoms. Tasks that can greatly influence symptoms include watching TV or using a computer for long periods of time where the blink rate is decreased.

Uveitis is an ocular disease involving inflammation of the middle layer or uvea of the eye, and may also be understood to include any inflammatory process involving the interior of the eye. Uveitis includes anterior, intermediate, posterior and panuveitic forms, with the majority of uveitis cases anterior in location, involving inflammation of the iris and anterior chamber. This condition can occur as a single episode and subside with proper treatment or may take on a recurrent or chronic nature. Symptoms include red eye, injected conjunctiva, pain and decreased vision. Signs include dilated ciliary vessels, presence of cells and flare in the anterior chamber, and keratic precipitates on the posterior surface of the cornea. Intermediate uveitis includes inflammation and the presence of inflammatory cells in the vitreous cavity, and posterior uveitis include the inflammation of the retina and choroid. Uveitis may be secondary to any of a number of diseases and disorders, including acute posterior multifocal placoid pigment epitheliopathy, ankylosing spondylitis, Behget's disease, birdshot retinochoroidopathy, brucellosis, herpes simplex, herpes zoster, inflammatory bowel disease, juvenile rheumatoid arthritis, Kawasaki disease, leptospirosis, Lyme disease, multiple sclerosis, psoriatic arthritis, Reiter's syndrome, sarcoidosis, syphilis, systemic lupus erythematosus, toxocariasis, toxoplasmosis, tuberculosis, Vogt-Koyanagi-Harada syndrome, Whipple disease or polyarteritis nodosa.

Ocular inflammatory disease also includes inflammation and other conditions and syndromes associated with corneal transplant, also known as keratoplasty, in which a damaged cornea of a patient is replaced by the cornea from the eye of a donor, typically a human cadaver. Inflammation or other signs and symptoms of graft rejection occur in between about 5% to 30% of patients. Symptoms of inflammation or other graft rejection in corneal transplants include persistent discomfort, sensitivity to light, redness, or a change in vision.

In one aspect, ocular inflammatory disease, including but not limited to dry eye disease, uveitis, or inflammation or other conditions and syndromes associated with corneal transplant, may be treated with an ophthalmic dosage form including a compound of this invention. The ophthalmic dosage form may include one or more active ingredients in addition to a compound of this invention, such as for example artificial tear components, topical corticosteroids, non-steroidal anti-inflammatory drugs, or calcineurin inhibitors such as cyclosporine-A (Restasis®—Allergan). In a related embodiment, one or additional compounds may be given separately from a compound of this invention, such as separate administration of an ophthalmic dosage form including an artificial tear component, a topical corticosteroid, a non-steroidal anti-inflammatory drugs, a calcineurin inhibitor such a cyclosporine-A, or a combination of any of the foregoing.

In another aspect, compounds of this invention may be employed for the treatment of sexual dysfunction, including both male erectile dysfunction and female sexual dysfunction. In one particular embodiment, compounds of this invention invention are used in male patients to increase erectile function, including but not limiting to increasing erectile function so as to permit vaginal intercourse. In another particular embodiment, compounds of this invention are used to treat female sexual dysfunction, including but not limited to an increase in arousal success rate, desire success rate, levels of arousal and desire. For female sexual dysfunction, endpoints may, but need not, be determined by any of a number of validated instruments, including but not limited to the Female Sexual Distress Scale, Female Sexual Encounter Profile, Female Sexual Function Index, and Global Assessment Questionnaire. Patients treated for female sexual dysfunction may be premenopausal women or postmenopausal women.

6. Assays and Animal Models

Selected compounds are tested in assays to determine binding and functional status, and are tested in animal models of feeding behavior as discussed below. The following assays and animal models are employed, with modifications, if any, as discussed in the examples.

6.1 Competitive Inhibition Assays Using [$I^{125}$]-NDP-α-MSH

A competitive inhibition binding assay is performed using membrane homogenates prepared from HEK-293 cells that express human recombinant hMC1-R, hMC3-R, hMC4-R, or hMC5-R. Assays are performed in 96 well GF/B Millipore multiscreen filtration plates (MAFB NOB10) pre-coated with 0.5% bovine serum albumin (Fraction V). Membrane homogenates are incubated with 0.2 nM (for hMC4-R) 0.4 nM (for MC3-R and MC5-R) or 0.1 nM (for mouse B16 MC1-R or hMC1-R) [$I^{125}$]-NDP-α-MSH (Perkin Elmer) and increasing concentrations of test compounds in buffer containing 25 mM HEPES buffer (pH 7.5) with 100 mM NaCl, 2 mM $CaCl_2$, 2 mM $MgCl_2$, 0.3 mM 1,10-phenanthroline, and 0.2% bovine serum albumin. After incubation for 60 minutes at 37° C., the assay mixture is filtered and the membranes washed three times with ice-cold buffer. Filters are dried and counted in a gamma counter for bound radioactivity. Non-specific binding is measured by inhibition of binding of [$I^{125}$]-NDP-α-MSH in the presence of 1 µM NDP-α-MSH. Maximal specific binding (100%) is defined as the difference in radioactivity (cpm) bound to cell membranes in the absence and presence of 1 µM NDP-α-MSH. Radioactivity (cpm) obtained in the presence of test compounds is normalized with respect to 100% specific binding to determine the percent inhibition of [$I^{125}$]-NDP-α-MSH binding. Each assay is conducted in triplicate and the actual mean values are described, with results less than 0% reported as 0%. Ki values for test compounds are determined using Graph-Pad Prism® curve-fitting software.

6.2 Competitive Binding Assay Using Eu-NDP-α-MSH

Alternatively, a competitive inhibition binding assay was performed employing Eu-NDP-α-MSH (PerkinElmer Life Sciences catalog No. AD0225) with determination by time-resolved fluorometry (TRF) of the lanthanide chelate. In comparison studies with [$I^{125}$]-NDP-α-MSH, the same values, within experimental error ranges, were obtained for percent inhibition and Ki. Typically competition experiments to determine Ki values were conducted by incubating membrane homogenates prepared from HEK-293 cells that express recombinant hMC1-R, hMC3-R, hMC4-R or hMC5-R with 9 different concentrations of test compounds of interest and 2 nM of Eu-NDP-α-MSH in a solution containing 25 mM HEPES buffer with 100 mM NaCl, 2 mM $CaCl_2$, 2 mM $MgCl_2$ and 0.3 mM 1,10-phenanthroline. After incubation for 90 minutes at 37° C., the reaction was stopped by filtration over AcroWell 96-well filter plates (Pall Life Sciences). The filter plates were washed 4 times with 200 µL of ice-cold phosphate-buffered saline. DELFIA Enhancement solution (PerkinElmer Life Sciences) was added to each well. The plates were incubated on a shaker for 15 minutes and read at 340 nm excitation and 615 nm emission wavelengths. Each assay was conducted in duplicate and mean values were utilized. Ki values were determined by curve-fitting with Graph-Pad Prism® software using a one-site fixed-slope competition binding model.

6.3 Competitive Binding Assays Using [$I^{125}$]AgRP (83-132)

Competitive binding studies using [$I^{125}$]-AgRP (83-132) are carried out using membrane homogenates isolated from cells that express hMC4-R. The assays are performed in 96-well GF/B Millipore multiscreen filtration plates (MAFB NOB10) pre-coated with 0.5% bovine serum albumin (Fraction V). The assay mixture contained 25 mM HEPES buffer (pH 7.5) with 100 mM NaCl, 2 mM $CaCl_2$, 2 mM $MgCl_2$, 0.3 mM 1,10-phenanthroline, 0.5% bovine serum albumin, membrane homogenates, radioligand [$I^{125}$]-AgRP (83-132) (Perkin Elmer) and increasing concentrations of compounds in a total volume of 200 μL. Binding is measured at radioligand concentrations of 0.2 nM. After incubating for 1 hour at 37° C., the reaction mixture is filtered and washed with assay buffer containing 500 mM NaCl. The dried discs are punched out from the plate and counted on a gamma counter. The total binding of the radioligand did not exceed 10% of the counts added to the reaction mixture. Ki values for test compounds are determined using Graph-Pad Prism® curve-fitting software.

6.4 Assay for Agonist Activity

Accumulation of intracellular cAMP is examined as a measure of the ability of the test compounds to elicit a functional response in HEK-293 cells that express MC4-R, or, for MC1-R, in HBL cells. Confluent HEK-293 cells that express recombinant hMC4-R, or HBL cells that express MC1-R, are detached from culture plates by incubation in enzyme-free cell dissociation buffer. Dispersed cells are suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine (IBMX), a phosphodiesterase inhibitor. The cells are plated in 96-well plates at a density of $0.5 \times 10^5$ cells per well and pre-incubated for 30 minutes. Cells are exposed for 1 hour at 37° C. to test compounds dissolved in DMSO (final DMSO concentration of 1%) at a concentration range of 0.05-5000 nM in a total assay volume of 200 μL. NDP-α-MSH is used as the reference agonist. At the end of the incubation period, cells are disrupted by the addition of 50 μL of lysis buffer (cAMP EIA kit, Amersham) followed by vigorous pipetting. Levels of cAMP in the lysates are determined using a cAMP EIA kit (Amersham). Data analysis is performed by nonlinear regression analysis with Graph-Pad Prism® software. The maximum efficacies of the test compounds are compared to that achieved by the reference melanocortin agonist NDP-α-MSH.

6.5 Food Intake After IN and IP Dosing

Changes in food intake are evaluated for selected compounds of this invention. Male C57BL/6 mice are obtained from Jackson labs (Bar Harbor, ME). Animals are individually housed in conventional plexiglass hanging cages and maintained on a controlled 12 hour on/off light cycle. Water and pelleted (Harlan Teklad 2018 18% Protein Rodent Diet) food is provided ad libitum. The mice are dosed IP (by intraperitoneal injection) after a 24 hour fast or IN (by intranasal administration) with vehicle or selected compounds (0.1-3 mg/kg, and in some cases up to 10 mg/kg). All animals are dosed once a day (or up to four consecutive days) at the start of the "lights off" period. The changes in food intake weight for the 4 hour and 20 hour period after dosing relative to control animals administered vehicle are determined.

6.6 Induction of Penile Erection

The ability of compounds of this invention to induce penile erection (PE) in male rats are evaluated with selected compounds. Male Sprague-Dawley rats weighing 250-300 g are kept on a 12 hour on/off light cycle with food and water ad libitum. All behavioral studies are performed between 9 a.m. and 4 p.m. Groups of 6-8 rats are administered compounds of this invention at a variety of doses via an IV route. Immediately after treatment, rats are placed into individual polystyrene cages (27 cm long, 16 cm wide, and 25 cm high) for behavioral observation, typically by remote video monitoring. Rats are observed for one hour, and the number of yawns, grooming bouts and PEs are recorded in 10-minute bins.

6.7 Determination of Mass and Nuclear Magnetic Resonance Analysis

The mass values are determined using a Waters MicroMass ZQ device utilizing a positive mode. Mass determinations are compared with calculated values and expressed in the form of mass weight plus one (M+1 or M+H).

Proton NMR data is obtained using a Bruker 300 MHz spectrometer. The spectra are obtained after dissolving compounds in a deuteriated solvent such as chloroform, DMSO, or methanol as appropriate.

7. EXAMPLES

The following compounds were synthesized using one of the foregoing schemes, or alternatively using one or more variants on one of the foregoing schemes. In the following listings, the chemical naming protocol and structure diagrams employ and rely on the chemical naming features as utilized by the ChemDraw program (available from Cambridgesoft Corp.) or ISIS Draw (MDL Information Systems, Inc.). In particular, the compound names were derived from the structures using the Autonom program as utilized by ChemDraw Ultra or ISIS Draw. In the structure diagrams, hydrogens are assumed and not disclosed, except as otherwise shown. Values given for Ki were obtained using [$I^{125}$]-NDP-α-MSH as described in 6.1 above, unless otherwise indicated with an asterisk, in which case values are for Eu-NDP-α-MSH as described in 6.2 above.

Example 1

(R)-1,2,3,4-Tetrahydro-isoquinoline-3-carboxylic acid {(R)-1-(4-chlorobenzyl)-2-oxo-2-[4-oxo-1-phenyl-3-(2-[1,2,4]triazol-1-yl-ethyl)-1,3,8-triaza-spiro [4.5]dec-8-yl]-ethyl}-amide The compound of Example 1 was synthesized by the methods of Schemes 1 and 2 described above, in which 1,2,4-triazole sodium salt and microwave synthesis was used.

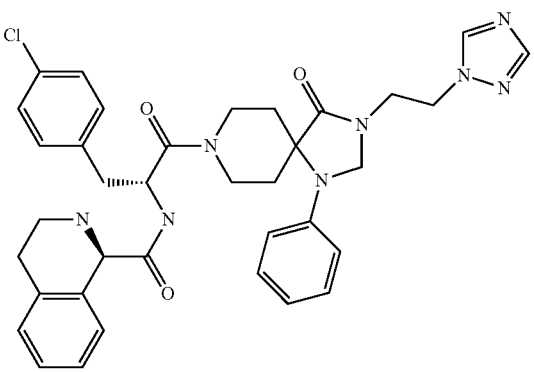

| Ki (nM) (NDP-α-MSH) | | | |
|---|---|---|---|
| MC1-R | MC3-R | MC4-R | MC5-R |
| >10,000 | 3204 | 264 | - |

Example 2

(R)-1,2,3,4-Tetrahydro-isoquinoline-3-carboxylic acid {(R)-1-(4-chlorobenzyl)-2-[3-(2-dimethylamino-ethyl)-4-oxo-1-phenyl-1,3,8-triaza-spiro[4.5]dec-8-yl]-2-oxo-ethyl}-amide The compound of Example 2 was synthesized by the methods of Schemes 1 and 2 described above, in which dimethylamine and microwave synthesis was used.

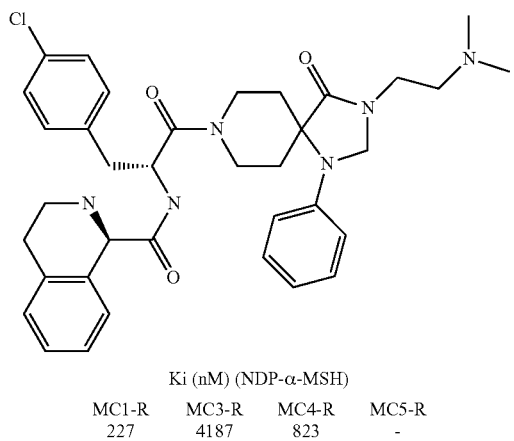

Ki (nM) (NDP-α-MSH)

| MC1-R | MC3-R | MC4-R | MC5-R |
|---|---|---|---|
| 227 | 4187 | 823 | - |

Example 3

(R)-1,2,3,4-Tetrahydro-isoquinoline-3-carboxylic acid {(R)-1-(4-chlorobenzyl)-2-[3-(2-diethylamino-ethyl)-4-oxo-1-phenyl-1,3,8-triaza-spiro[4.5]dec-8-yl]-2-oxo-ethyl}-amide The compound of Example 3 was synthesized by the methods of Schemes 1 and 2 described above, in which diethylamine and microwave synthesis was used.

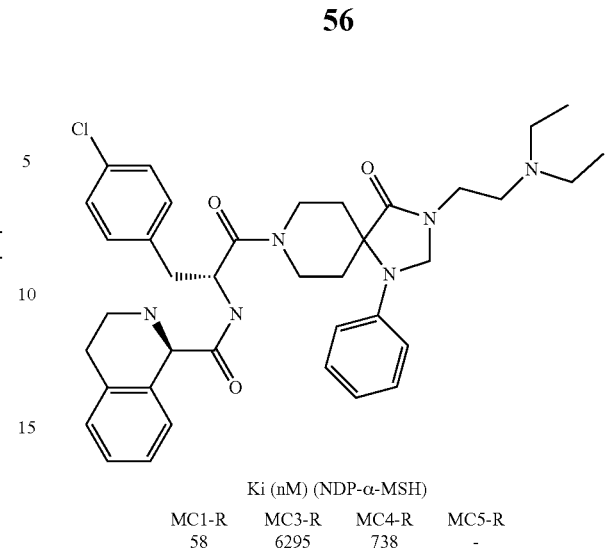

Ki (nM) (NDP-α-MSH)

| MC1-R | MC3-R | MC4-R | MC5-R |
|---|---|---|---|
| 58 | 6295 | 738 | - |

Example 4

(R)-1,2,3,4-Tetrahydro-isoquinoline-3-carboxylic acid [(R)-1-(4-chloro-benzyl)-2-(3-{[2-(1H-indol-3-yl)-ethylcarbamoyl]-methyl}-4-oxo-1-phenyl-1,3,8-triaza-spiro[4.5]dec-8-yl)-2-oxo-ethyl]-amide The compound of Example 4 was synthesized by the methods of Schemes 1 and 3 described above, in which 2-(1H-indol-3-yl)ethylamine was used.

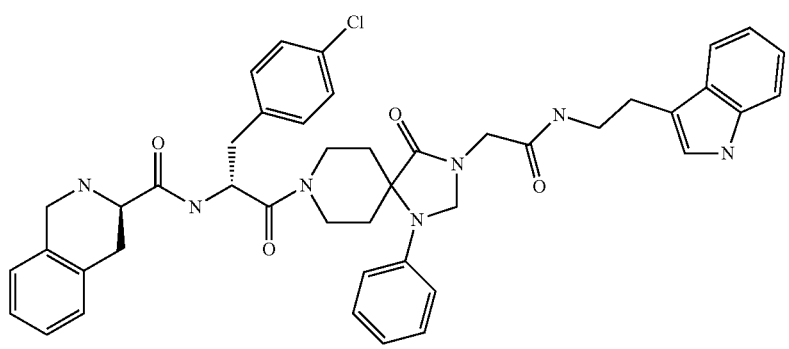

Inhibition at 1μM (NDP-α-MSH)

| MC1-R | MC3-R | MC4-R | MC5-R |
|---|---|---|---|
| 11 | 20 | 69 | 33 |

Ki (nM) (NDP-α-MSH)

| MC1-R | MC3-R | MC4-R | MC5-R |
|---|---|---|---|
| >10,000* | 7148* | 313* | 4046* |

Example 5

(R)-1,2,3,4-Tetrahydro-isoquinoline-3-carboxylic acid ((R)-1-(4-chloro-benzyl)-2-{3-[2-(2-methoxy-ethylamino)-ethyl]-4-oxo-1-phenyl-1,3,8-triaza-spiro[4.5]dec-8-yl}-2-oxo-ethyl)-amide The compound of Example 5 was synthesized by the methods of Schemes 1 and 2 described above, in which 2-methoxyethylamine was used.

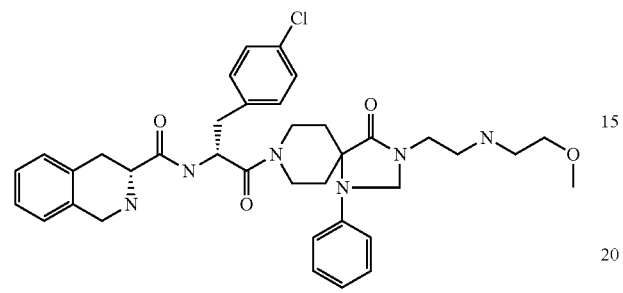

Inhibition at 1μM (NDP-α-MSH)

| MC1-R | MC3-R | MC4-R | MC5-R |
|---|---|---|---|
| 8 | 23 | 69 | 38 |

Ki (nM) (NDP-α-MSH)

| MC1-R | MC3-R | MC4-R | MC5-R |
|---|---|---|---|
| 1670 | - | 107 | - |

Example 6

(R)-1,2,3,4-Tetrahydro-isoquinoline-3-carboxylic acid [(R)-1-(4-chloro-benzyl)-2-(3-{2-[2-(3-fluoro-phenyl)-ethylamino]-ethyl}-4-oxo-1-phenyl-1,3,8-triaza-spiro[4.5]dec-8-yl)-2-oxo-ethyl]-amide The compound of Example 6 was synthesized by the methods of Schemes 1 and 2 described above, in which 2-(3-fluorophenyl)ethylamine was used.

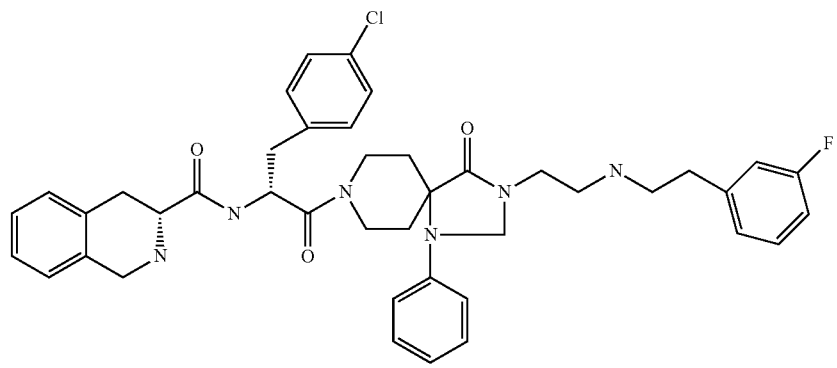

Inhibition at 1μM (NDP-α-MSH)

| MC1-R | MC3-R | MC4-R | MC5-R |
|---|---|---|---|
| 15 | 33 | 78 | 52 |

Ki (nM) (NDP-α-MSH)

| MC1-R | MC3-R | MC4-R | MC5-R |
|---|---|---|---|
| - | - | 176 | - |

Example 7

(R)-1,2,3,4-Tetrahydro-isoquinoline-3-carboxylic acid ((R)-1-(4-chloro-benzyl)-2-oxo-2-{4-oxo-1-phenyl-3-[2-(2-thien-2-yl-ethylamino)-ethyl]-1,3,8-triaza-spiro[4.5]dec-8-yl}-ethyl)-amide The compound of Example 7 was synthesized by the methods of Schemes 1 and 2 described above, in which 2-(thien-2-yl) ethylamine was used.

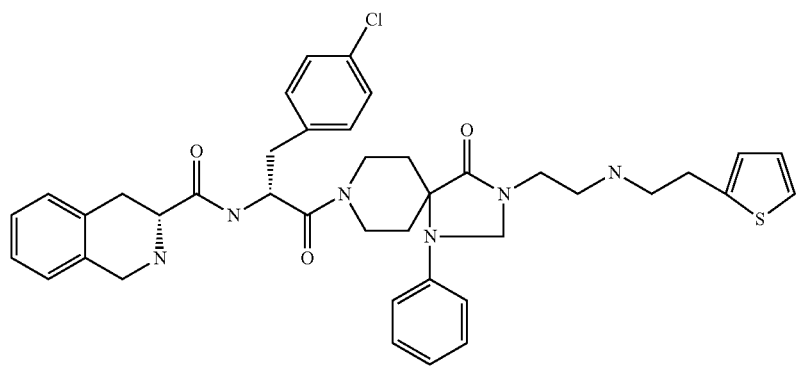

| Inhibition at 1μM (NDP-α-MSH) | | | |
|---|---|---|---|
| MC1-R | MC3-R | MC4-R | MC5-R |
| 34 | 48 | 81 | 64 |

| Ki (nM) (NDP-α-MSH) | | | |
|---|---|---|---|
| MC1-R | MC3-R | MC4-R | MC5-R |
| - | - | 140 | - |

Example 8

(R)-1,2,3,4-Tetrahydro-isoquinoline-3-carboxylic acid [(R)-2-[3-(tert-butylcarbamoyl-methyl)-4-oxo-1-phenyl-1,3,8-triaza-spiro[4.5]dec-8-yl]-1-(4-chloro-benzyl)-2-oxo-ethyl]-amide The compound of Example 8 was synthesized by the methods of Schemes 1 and 3 described above, in which t-butylamine was used.

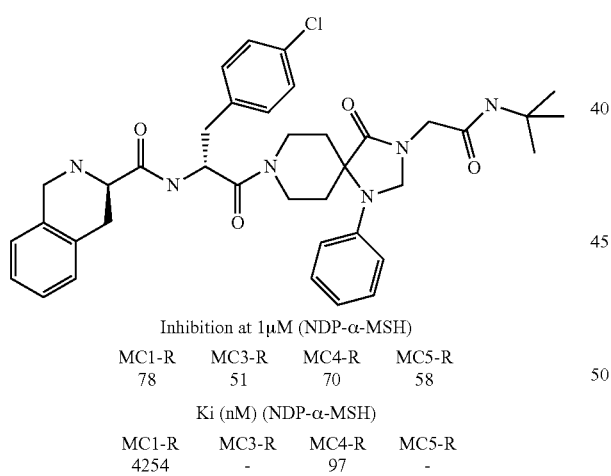

| Inhibition at 1μM (NDP-α-MSH) | | | |
|---|---|---|---|
| MC1-R | MC3-R | MC4-R | MC5-R |
| 78 | 51 | 70 | 58 |

| Ki (nM) (NDP-α-MSH) | | | |
|---|---|---|---|
| MC1-R | MC3-R | MC4-R | MC5-R |
| 4254 | - | 97 | - |

Example 9

(R)-1,2,3,4-Tetrahydro-isoquinoline-3-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 9 was synthesized by the methods of Schemes 1 and 3 described above, in which cyclohexylamine was used.

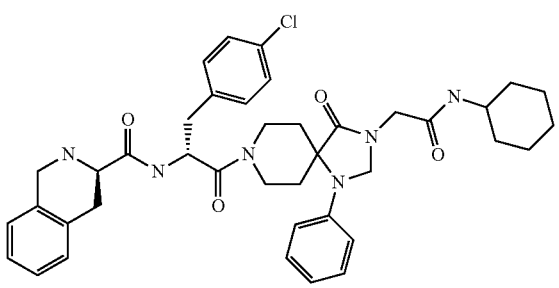

| Inhibition at 1μM (NDP-α-MSH) | | | |
|---|---|---|---|
| MC1-R | MC3-R | MC4-R | MC5-R |
| 46 | 39 | 72 | 25 |

| Ki (nM) (NDP-α-MSH) | | | |
|---|---|---|---|
| MC1-R | MC3-R | MC4-R | MC5-R |
| 4444 | - | 122 | - |

Example 10

(R)-N-((R)-3-(4-Chlorophenyl)-1-oxo-1-(4-oxo-1-phenyl-1,3,8-triazaspiro[4.5]decan-8-yl)propan-2-yl)-1,2,3,4-tetrahydroisoquinoline-3-carboxamide The compound of Example 10 was synthesized by the methods of Scheme 1 described above, omitting the alkylation with methyl bromoacetate and deprotecting the final compound with trifluoroacetic acid. The compound was tested as described above, with results as shown.

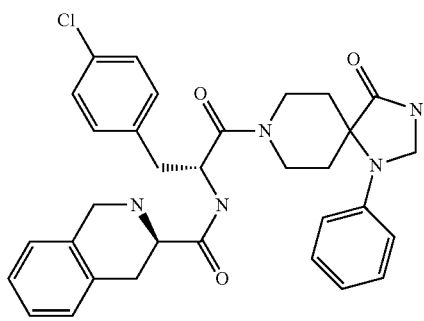

Inhibition at 1μM (NDP-α-MSH)

| MC1-R | MC3-R | MC4-R | MC5-R |
|---|---|---|---|
| 7 | 21 | 52 | 35 |

Ki (nM) (NDP-α-MSH)

| MC1-R | MC3-R | MC4-R | MC5-R |
|---|---|---|---|
| >10,000 | - | 539 | - |

Example 11

(R)-N-((R)-3-(4-Chlorophenyl)-1-(3-(2-(4-methylpiperazin-1-yl)-2-oxoethyl)-4-oxo-1-phenyl-1,3,8-triazaspiro[4.5]decan-8-yl)-1-oxopropan-2-yl)-1,2,3,4-tetrahydroisoquinoline-3-carboxamide The compound of Example 11 was synthesized by the methods of Scheme 3 described above, in which 1-methylpiperazine was used. The compound was tested as described above, with results as shown.

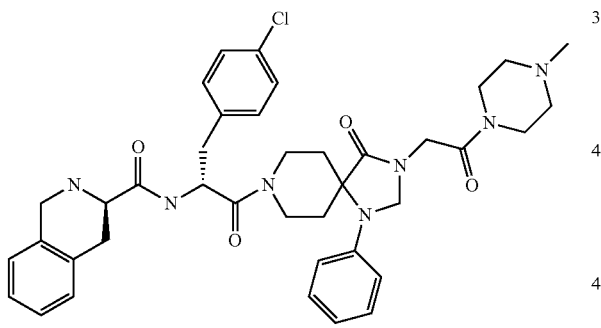

Inhibition at 1 μM (NDP-α-MSH)

| MC1-R | MC3-R | MC4-R | MC5-R |
|---|---|---|---|
| 17 | 21 | 69 | 41 |

Ki (nM) (NDP-α-MSH)

| MC1-R | MC3-R | MC4-R | MC5-R |
|---|---|---|---|
| 2279 | - | 212 | - |

Example 12

Methyl 2-(8-((R)-3-(4-chlorophenyl)-2-((R)-1,2,3,4-tetrahydroisoquinoline-3-carboxamido)propanoyl)-4-oxo-1-phenyl-1,3,8-triazaspiro[4.5]decan-3-yl)acetate The compound of Example 12 was synthesized by the method of Scheme 1 described above, in which compound 1-5 was deprotected with trifluoroacetic acid. The compound was tested as described above, with results as shown.

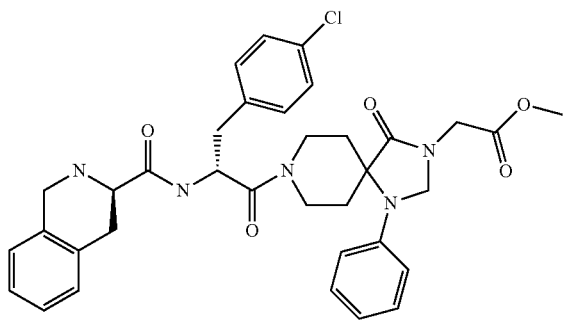

Inhibition at 1 μM (NDP-α-MSH)

| MC1-R | MC3-R | MC4-R | MC5-R |
|---|---|---|---|
| 0 | 3 | 73 | 24 |

Example 13

(R)-N-((R)-3-(4-Chlorophenyl)-1-(3-methyl-4-oxo-1-phenyl-1,3,8-triazaspiro[4.5]decan-8-yl)-1-oxopropan-2-yl)-1,2,3,4-tetrahydroisoquinoline-3-carboxamide The compound of Example 13 was synthesized by the method of Scheme 1 described above, in which iodomethane was used instead of methyl bromoacetate, and as a final step the Boc protecting group was removed with trifluoroacetic acid. The compound was tested as described above, with results as shown.

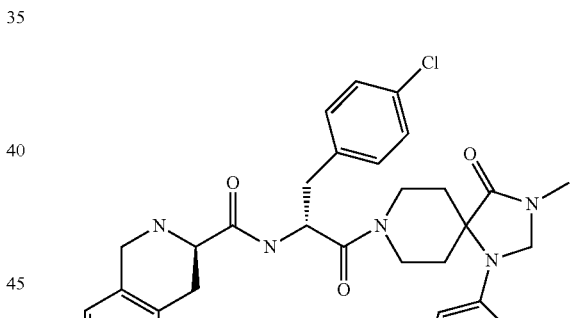

Ki (nM) (NDP-α-MSH)

| MC1-R | MC3-R | MC4-R | MC5-R |
|---|---|---|---|
| 8181 | 6066 | 82 | 2402 |

Example 14

(R)-N-((R)-3-(4-Chlorophenyl)-1-(3-(2-(isopropylamino)-2-oxoethyl)-4-oxo-1-phenyl-1,3,8-triazaspiro[4.5]decan-8-yl)-1-oxopropan-2-yl)-1,2,3,4-tetrahydroisoquinoline-3-carboxamide The compound of Example 14 was synthesized by the methods of Scheme 3 described above, in which isopropylamine was used. The compound was tested as described above, with results as shown.

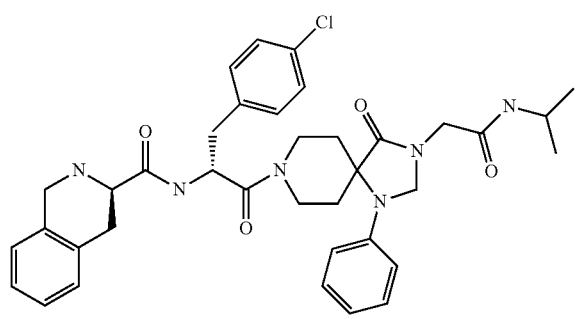

Ki (nM) (NDP-α-MSH)

| MC1-R | MC3-R | MC4-R | MC5-R |
|-------|-------|-------|-------|
| 8400  | 8033  | 138   | 4153  |

Example 15

(R)-N-((R)-1-(3-(2-(Butylamino)-2-oxoethyl)-4-oxo-1-phenyl-1,3,8-triazaspiro[4.5]decan-8-yl)-3-(4-chlorophenyl)-1-oxopropan-2-yl)-1,2,3,4-tetrahydroisoquinoline-3-carboxamide The compound of Example 15 was synthesized by the methods of Scheme 3 described above, in which n-butylamine was used. The compound was tested as described above, with results as shown.

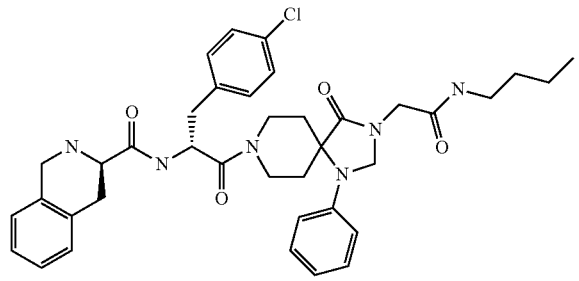

Ki (nM) (NDP-α-MSH)

| MC1-R | MC3-R | MC4-R | MC5-R |
|-------|-------|-------|-------|
| 6037  | 6011  | 141   | 3661  |

Example 16

(R)-N-((R)-1-(3-(2-(Benzylamino)-2-oxoethyl)-4-oxo-1-phenyl-1,3,8-triazaspiro[4.5]decan-8-yl)-3-(4-chlorophenyl)-1-oxopropan-2-yl)-1,2,3,4-tetrahydroisoquinoline-3-carboxamide The compound of Example 16 was synthesized by the methods of Scheme 3 described above, in which benzylamine was used. The compound was tested as described above, with results as shown.

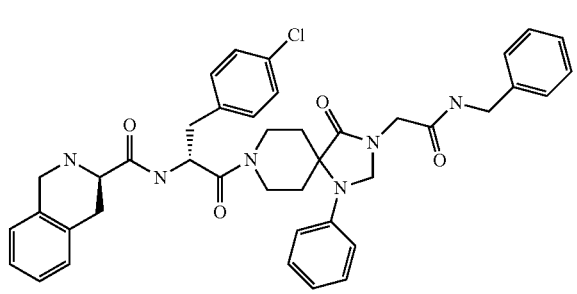

Ki (nM) (NDP-α-MSH)

| MC1-R | MC3-R | MC4-R | MC5-R |
|-------|-------|-------|-------|
| 3009  | 3142  | 51    | 1772  |

Example 17

(R)-N-(R)-3-(4-Chlorophenyl)-1-oxo-1-(4-oxo-3-(2-oxo-2-(phenylamino)ethyl)-1-phenyl-1,3,8-triazaspiro[4.5]decan-8-yl)propan-2-yl)-1,2,3,4-tetrahydroisoquinoline-3-carboxamide The compound of Example 17 was synthesized by the method of Scheme 3 described above, in which aniline was used. The compound was tested as described above, with results as shown.

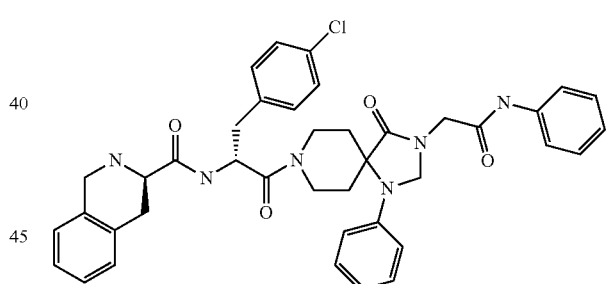

Ki (nM) (NDP-α-MSH)

| MC1-R | MC3-R | MC4-R | MC5-R |
|-------|-------|-------|-------|
| 3305  | 4287  | 112   | 2940  |

Example 18

(R)-N-((R)-1-(3-(2-(Benzylamino)-2-oxoethyl)-1-(3-chlorophenyl)-4-oxo-1,3,8-triazaspiro[4.5]decan-8-yl)-3-(4-chlorophenyl)-1-oxopropan-2-yl)-1,2,3,4-tetrahydroisoquinoline-3-carboxamide The compound of Example 18 was synthesized by the method of Scheme 5 described above, in which 3-chloroaniline was used.

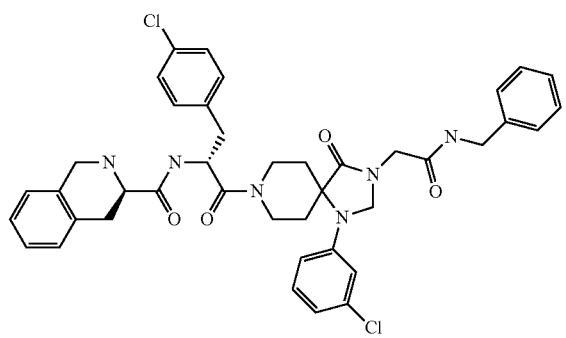

Ki (nM) (NDP-α-MSH)

| MC1-R | MC3-R | MC4-R | MC5-R |
|---|---|---|---|
| 2285* | 6823* | 151* | 2587* |

Example 19

(R)-N-((R)-1-(3-(2-(Benzylamino)-2-oxoethyl)-1-(4-chlorophenyl)-4-oxo-1,3,8-triazaspiro[4.5]decan-8-yl)-3-(4-chlorophenyl)-1-oxopropan-2-yl)-1,2,3,4-tetrahydroisoquinoline-3-carboxamide The compound of Example 19 was synthesized by the method of Scheme 5 described above, in which 4-chloroaniline was used.

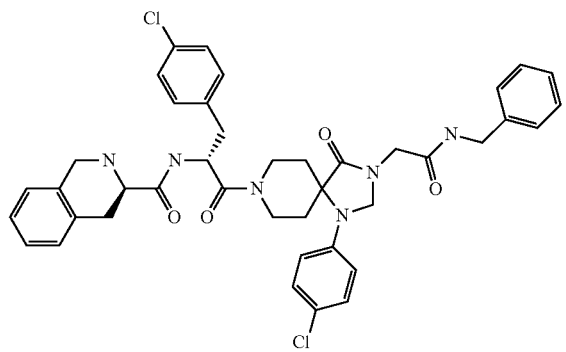

Ki (nM) (NDP-α-MSH)

| MC1-R | MC3-R | MC4-R | MC5-R |
|---|---|---|---|
| 2395* | 9760* | 103* | 2205* |

Example 20

(R)-1,2,3,4-Tetrahydro-isoquinoline-3-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The following compound was synthesized by the method of Scheme 3 in which cyclohexylamine was used. Following purification, the compound was tested as described above with the results shown.

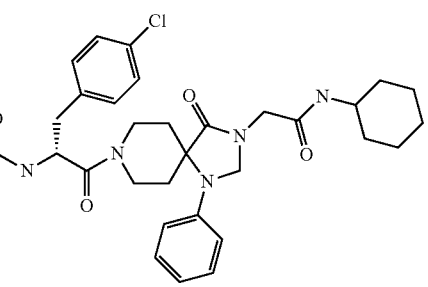

Inhibition at 1 μM (NDP-α-MSH)

| MC1-R | MC3-R | MC4-R | MC5-R |
|---|---|---|---|
| 46% | 39% | 72% | 25% |

Ki (nM) (NDP-α-MSH)

| MC1-R | MC3-R | MC4-R | MC5-R |
|---|---|---|---|
| 4444 | N/A | 122 | N/A |

Example 21

(S)-Piperidine-2-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 21 was synthesized by the methods of Scheme 4 described above, in which Boc-(S)-piperidine-2-carboxylic acid was used. Following purification, the compound was tested as described above with the results shown.

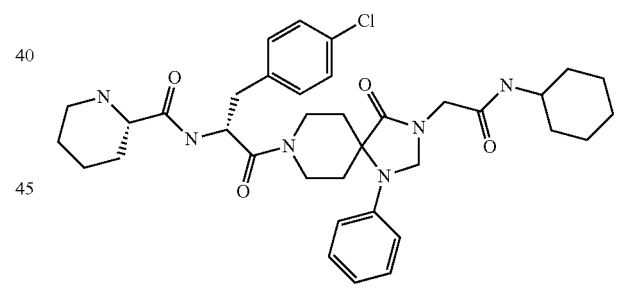

Ki (nM) (NDP-α-MSH)

| MC1-R | MC3-R | MC4-R | MC5-R |
|---|---|---|---|
| 2090* | 8451* | 539* | 1129* |

Example 22

2-{8-[(R)-2-(2-Amino-acetylamino)-3-(4-chloro-phenyl)-propionyl]-4-oxo-1-phenyl-1,3,8-triaza-spiro[4.5]dec-3-yl}-N-cyclohexyl-acetamide The compound of Example 22 was synthesized by the methods of Scheme 4 described above, in which Boc-glycine was used. Following purification, the compound was tested as described above with the results shown.

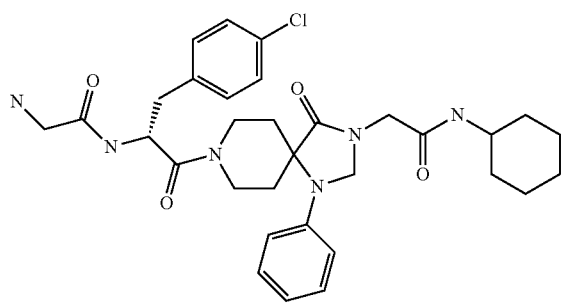

Ki (nM) (NDP-α-MSH)

| MC1-R | MC3-R | MC4-R | MC5-R |
|---|---|---|---|
| 3631* | >10000* | 742* | 1899* |

Example 23

(S)-1,2,3,4-Tetrahydro-isoquinoline-3-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 23 was synthesized by the methods of Scheme 4 described above, in which Boc-(S)-1,2,3,4-tetrahydro-isoquinoline-3-carboxylic acid was used. Following purification, the compound was tested as described above with the results shown.

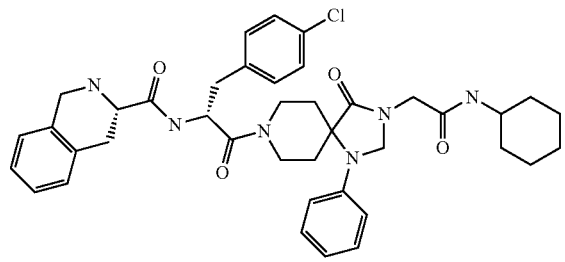

Ki (nM) (NDP-α-MSH)

| MC1-R | MC3-R | MC4-R | MC5-R |
|---|---|---|---|
| 2582* | 9162* | 319* | 1159* |

Example 24

(S)-Pyrrolidine-2-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 24 was synthesized by the methods of Scheme 4 described above, in which Boc-(S)-pyrrolidine-2-carboxylic acid was used. Following purification, the compound was tested as described above with the results shown.

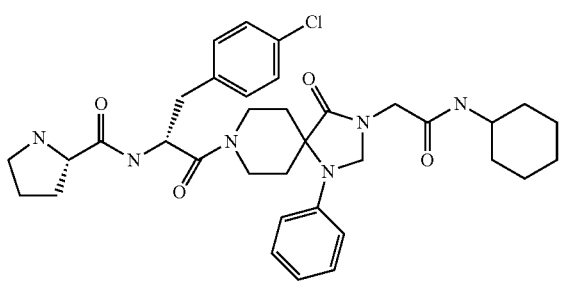

Ki (nM) (NDP-α-MSH)

| MC1-R | MC3-R | MC4-R | MC5-R |
|---|---|---|---|
| 3015* | >10000* | 695* | 1244* |

Example 25

(R)-Pyrrolidine-2-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 25 was synthesized by the methods of Scheme 4 described above, in which Boc-(R)-pyrrolidine-2-carboxylic acid was used. Following purification, the compound was tested as described above with the results shown.

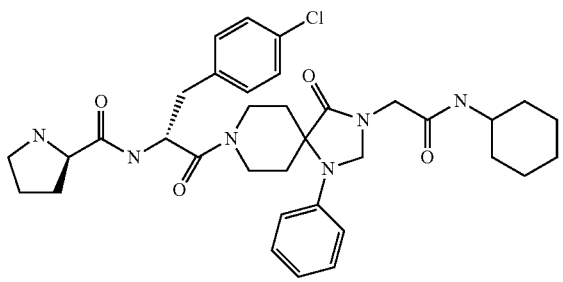

Ki (nM) (NDP-α-MSH)

| MC1-R | MC3-R | MC4-R | MC5-R |
|---|---|---|---|
| 2958* | >10000* | 1138* | 1688* |

Example 26

(S)-Piperidine-3-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 26 was synthesized by the methods of Scheme 4 described above, in which Boc-(S)-piperidine-3-carboxylic acid was used. Following purification, the compound was tested as described above with the results shown.

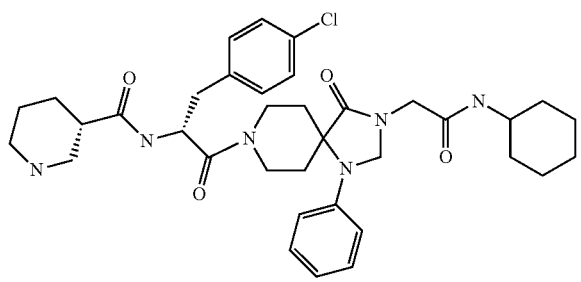

Ki (nM) (NDP-α-MSH)

| MC1-R | MC3-R | MC4-R | MC5-R |
|---|---|---|---|
| 924* | 8379* | 502* | 927* |

Example 27

(R)-Piperidine-3-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 27 was synthesized by the methods of Scheme 4 described above, in which Boc-(R)-piperidine-3-carboxylic acid was used. Following purification, the compound was tested as described above with the results shown.

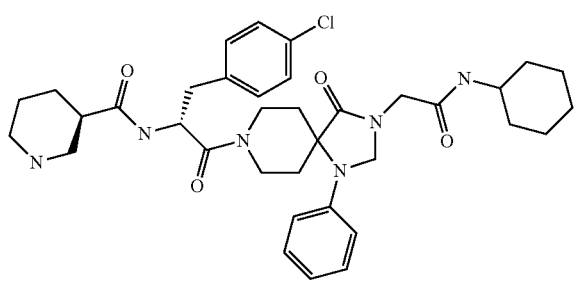

Ki (nM) (NDP-α-MSH)

| MC1-R | MC3-R | MC4-R | MC5-R |
|---|---|---|---|
| 2379* | >10000* | 902* | 1111* |

Example 28

2-{8-[(R)-2-Acetylamino-3-(4-chloro-phenyl)-propionyl]-4-oxo-1-phenyl-1,3,8-triaza-spiro[4.5]dec-3-yl}-N-cyclohexyl-acetamide The compound of Example 28 was synthesized by the methods of Scheme 4 described above, in which acetic acid was used. Following purification, the compound was tested as described above with the results shown.

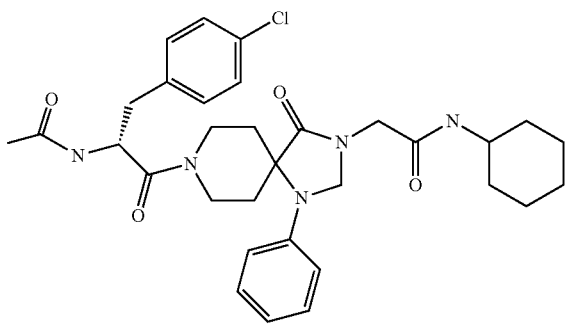

Ki (nM) (NDP-α-MSH)

| MC1-R | MC3-R | MC4-R | MC5-R |
|---|---|---|---|
| >10000* | >10000* | 4654* | 4641* |

Example 29

(R)-1,2,3,4-Tetrahydro-isoquinoline-3-carboxylic acid [(S)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 29 was synthesized by the methods of Scheme 4 described above, in which Boc-(R)-1,2,3,4-tetrahydro-isoquinoline-3-carboxylic acid was used. Following purification, the compound was tested as described above with the results shown.

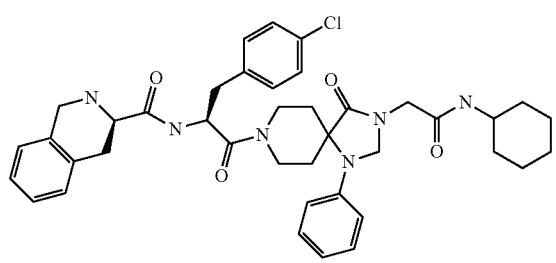

Ki (nM) (NDP-α-MSH)

| MC1-R | MC3-R | MC4-R | MC5-R |
|---|---|---|---|
| 7467* | >10000* | 6693* | 914* |

Example 30

(R)-1,2,3,4-Tetrahydro-isoquinoline-3-carboxylic acid [(R)-1-benzyl-2-(3-cyclohexylcarbamoylmethyl-4-oxo-1-phenyl-1,3,8-triaza-spiro[4.5]dec-8-yl)-2-oxo-ethyl]-amide The compound of Example 30 was synthesized by the methods of Scheme 4 described above, in which Boc-(R)-1,2,3,4-tetrahydro-isoquinoline-3-carboxylic acid was used. Following purification, the compound was tested as described above with the results shown.

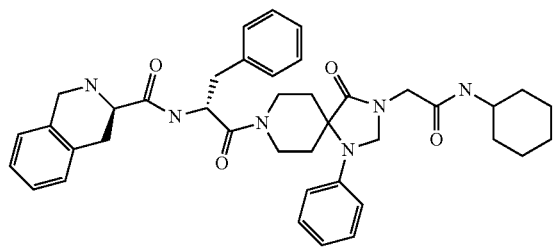

Ki (nM) (NDP-α-MSH)

| MC1-R | MC3-R | MC4-R | MC5-R |
|---|---|---|---|
| 7415* | >10000* | 1426* | 3650* |

Example 31

(R)-1,2,3,4-Tetrahydro-isoquinoline-3-carboxylic acid [(R)-1-(3-cyclohexylcarbamoylmethyl-4-oxo-1-phenyl-1,3,8-triaza-spiro[4.5]decane-8-carbonyl)-3-methyl-butyl]-amide The compound of Example 31 was synthesized by the methods of Scheme 4 described above, in which Boc-(R)-1,2,3,4-tetrahydro-isoquinoline-3-carboxylic acid was used. Following purification, the compound was tested as described above with the results shown.

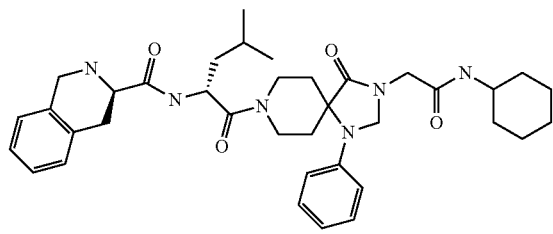

Ki (nM) (NDP-α-MSH)

| MC1-R | MC3-R | MC4-R | MC5-R |
|---|---|---|---|
| 2158* | 3919* | 5659* | 6593* |

Example 32

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-methyl-2-oxo-ethyl]-amide The compound of Example 32 was synthesized by the methods of Scheme 4 described above, in which Boc-(R)-1,2,3,4-tetrahydro-isoquinoline-3-carboxylic acid was used. Following purification, the compound was tested as described above with the results shown.

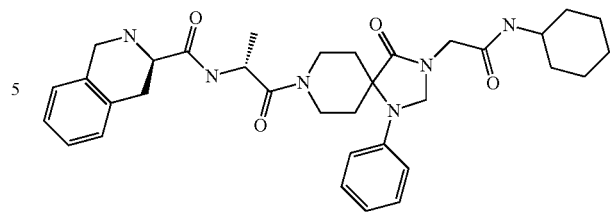

Ki (nM) (NDP-α-MSH)

| MC1-R | MC3-R | MC4-R | MC5-R |
|---|---|---|---|
| 1838* | 4164* | 6466* | 6496* |

Example 33

(R)-Piperidine-2-carboxylic acid [(R)-1-(4-chlorobenzyl)-2-(3-cyclohexylcarbamoylmethyl-4-oxo-1-phenyl-1,3,8-triaza-spiro[4.5]dec-8-yl)-2-oxo-ethyl]-amide The compound of Example 33 was synthesized by the methods of Scheme 4 described above, in which Boc-(R)-piperidine-2-carboxylic acid was used. Following purification, the compound was tested as described above with the results shown.

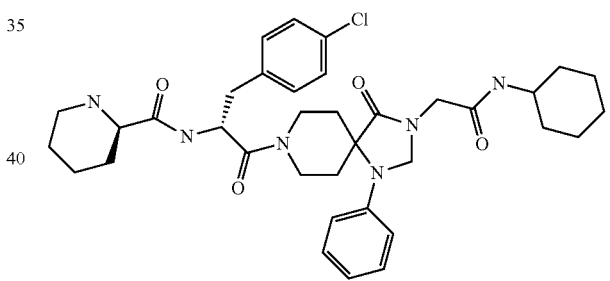

Ki (nM) (NDP-α-MSH)

| MC1-R | MC3-R | MC4-R | MC5-R |
|---|---|---|---|
| 1415* | >10000* | 784* | 1529* |

Example 34

Piperidine-4-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-xo-ethyl]-amide The compound of Example 34 was synthesized by the methods of Scheme 4 described above, in which Boc-(R)-piperidine-4-carboxylic acid was used. Following purification, the compound was tested as described above with the results shown.

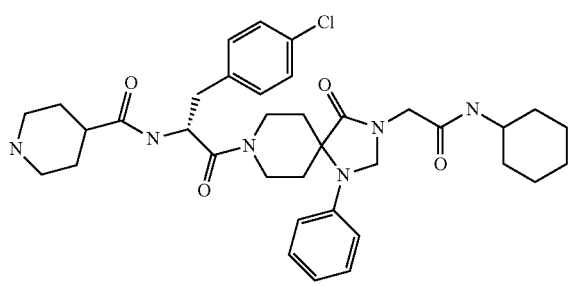

Ki (nM) (NDP-α-MSH)

| MC1-R | MC3-R | MC4-R | MC5-R |
|---|---|---|---|
| 641* | 10000* | 537* | 2332* |

Example 35

(R)-1,2,3,4-Tetrahydro-isoquinoline-3-carboxylic acid [2-(3-cyclohexylcarbamoylmethyl-4-oxo-1-phenyl-1,3,8-triaza-spiro[4.5]dec-8-yl)-2-oxo-ethyl]-amide The compound of Example 35 was synthesized by the methods of Scheme 4 described above, in which Boc-(R)-1,2,3,4-tetrahydro-isoquinoline-3-carboxylic acid was used.

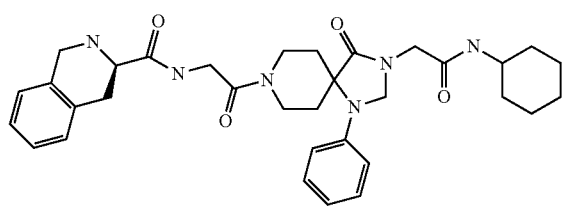

Example 36

(R)-1,2,3,4-Tetrahydro-isoquinoline-3-carboxylic acid [(R)-2-[3-(benzylcarbamoyl-methyl)-2,4-dioxo-1-phenyl-1,3,8-triaza-spiro[4.5]dec-8-yl]-1-(4-chloro-benzyl)-2-oxo-ethyl]-amide The following compound was synthesized by the methods of Scheme 7. Following purification, the compound was tested as described above with the results shown.

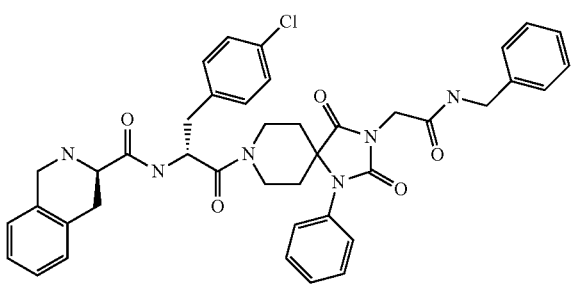

Ki (nM) (NDP-α-MSH)

| MC1-R | MC3-R | MC4-R | MC5-R |
|---|---|---|---|
| 3763* | 6020* | 132* | 6056* |

Example 37

(R)-1,2,3,4-Tetrahydro-isoquinoline-3-carboxylic acid [(R)-1-(4-chloro-benzyl)-2-(3-methylcarbamoylmethyl-4-oxo-1-phenyl-1,3,8-triaza-spiro[4.5]dec-8-yl)-2-oxo-ethyl]-amide The compound of Example 37 was synthesized by the methods of Scheme 4 described above, in which Boc-(R)-1,2,3,4-tetrahydro-isoquinoline-3-carboxylic acid was used. A 2.0 M solution of methylamine in THF was used for the first step of Scheme 4. Following purification, the compound was tested as described above with the results shown.

Ki (nM) (NDP-α-MSH)

| MC1-R | MC3-R | MC4-R | MC5-R |
|---|---|---|---|
| 258* | 6915* | 993* | 2757* |

Example 38

(R)-1,2,3,4-Tetrahydro-isoquinoline-3-carboxylic acid {(R)-1-(4-chloro-benzyl)-2-oxo-2-[4-oxo-3-(phenethylcarbamoyl-methyl)-1-phenyl-1,3,8-triaza-spiro[4.5]dec-8-yl]-ethyl}-amide The compound of Example 38 was synthesized by the methods of Scheme 4 described above, in which Boc-(R)-1,2,3,4-tetrahydro-isoquinoline-3-carboxylic acid was used. Following purification, the compound was tested as described above with the results shown.

Ki (nM) (NDP-α-MSH)

| MC1-R | MC3-R | MC4-R | MC5-R |
|---|---|---|---|
| 2181* | 5443* | 165* | 2687* |

Example 39

(R)-1,2,3,4-Tetrahydro-isoquinoline-3-carboxylic acid [(R)-1-(4-chloro-benzyl)-2-oxo-2-(4-oxo-1-phenyl-3-propylcarbamoylmethyl-1,3,8-triaza-spiro[4.5]dec-8-yl)-ethyl]-amide The compound of Example 39 was synthesized by the methods of Scheme 4 described above, in which Boc-(R)-1,2,3,4-tetrahydro-isoquinoline-3-carboxylic acid was used. Following purification, the compound was tested as described above with the results shown.

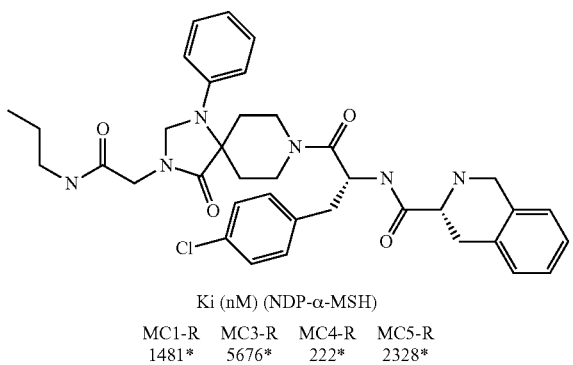

Ki (nM) (NDP-α-MSH)

| MC1-R | MC3-R | MC4-R | MC5-R |
|---|---|---|---|
| 1481* | 5676* | 222* | 2328* |

Example 40

(R)-1,2,3,4-Tetrahydro-isoquinoline-3-carboxylic acid ((R)-1-(4-chloro-benzyl)-2-{3-[(2-methyl-benzylcarbamoyl)-methyl]-4-oxo-1-phenyl-1,3,8-triaza-spiro[4.5]dec-8-yl}-2-oxo-ethyl)-amide The compound of Example 40 was synthesized by the methods of Scheme 4 described above, in which Boc-(R)-1,2,3,4-tetrahydro-isoquinoline-3-carboxylic acid was used. Following purification, the compound was tested as described above with the results shown.

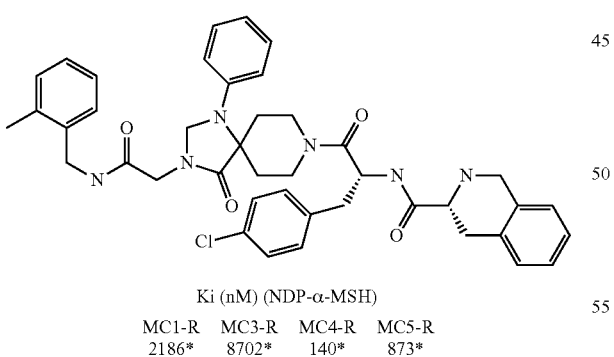

Ki (nM) (NDP-α-MSH)

| MC1-R | MC3-R | MC4-R | MC5-R |
|---|---|---|---|
| 2186* | 8702* | 140* | 873* |

Example 41

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-nicotinamide The compound of Example 41 was synthesized by the methods of Scheme 4 described above, in which pyridine-3-carboxylic acid was used. Following purification, the compound was tested as described above with the results shown.

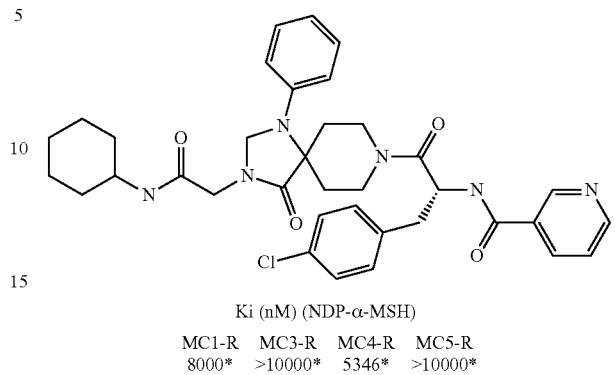

Ki (nM) (NDP-α-MSH)

| MC1-R | MC3-R | MC4-R | MC5-R |
|---|---|---|---|
| 8000* | >10000* | 5346* | >10000* |

Example 42

N-[(R)-1-(4-Chloro-benzyl)-2-(3-cyclohexylcarbamoylmethyl-4-oxo-1-phenyl-1,3,8-triaza-spiro[4.5]-dec-8-yl)-2-oxo-ethyl]-isonicotinamide The compound of Example 42 was synthesized by the methods of Scheme 4 described above, in which pyridine-4-carboxylic acid was used. Following purification, the compound was tested as described above with the results shown.

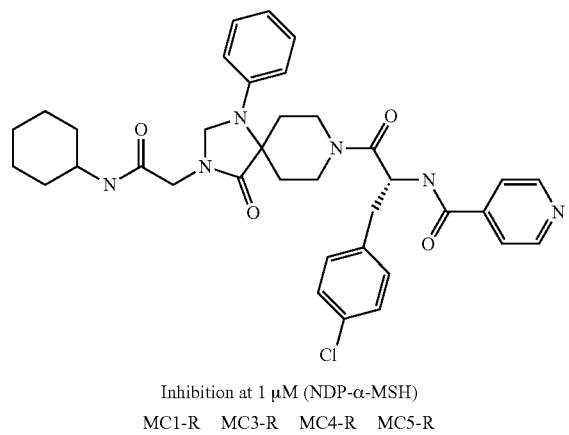

Inhibition at 1 μM (NDP-α-MSH)

| MC1-R | MC3-R | MC4-R | MC5-R |
|---|---|---|---|
| 9%* | 36%* | 53%* | 32%* |

Example 43

Cyclohexanecarboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 43 was synthesized by the methods of Scheme 4 described above, in which cyclohexylcarboxylic acid was used. Following purification, the compound was tested as described above with the results shown.

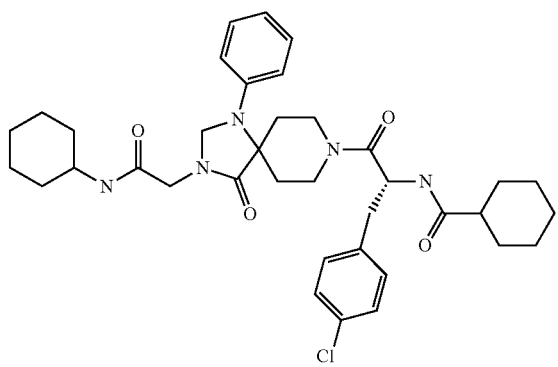

Inhibition at 1 µM (NDP-α-MSH)

| MC1-R | MC3-R | MC4-R | MC5-R |
|---|---|---|---|
| 13%* | 19%* | 34%* | 38%* |

Example 44

Pyridine-2-carboxylic acid [(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 44 was synthesized by the methods of Scheme 4 described above, in which pyridine-2-carboxylic acid was used. Following purification, the compound was tested as described above with the results shown.

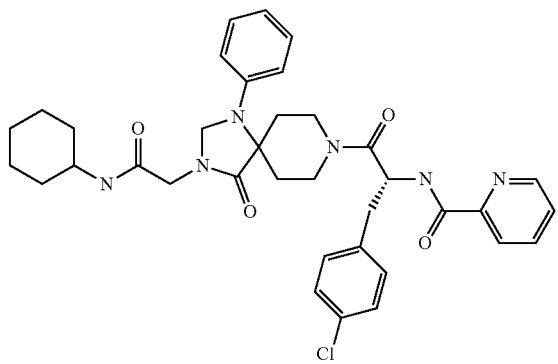

Inhibition at 1 µM (NDP-α-MSH)

| MC1-R | MC3-R | MC4-R | MC5-R |
|---|---|---|---|
| 9%* | 21%* | 36%* | 34%* |

Example 45

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-2-(2-hydroxy-ethylamino)-acetamide The compound of Example 45 was synthesized by the methods of Scheme 4 and Scheme 6 described above, in which aminoethanol was used. Following purification, the compound was tested as described above with the results shown.

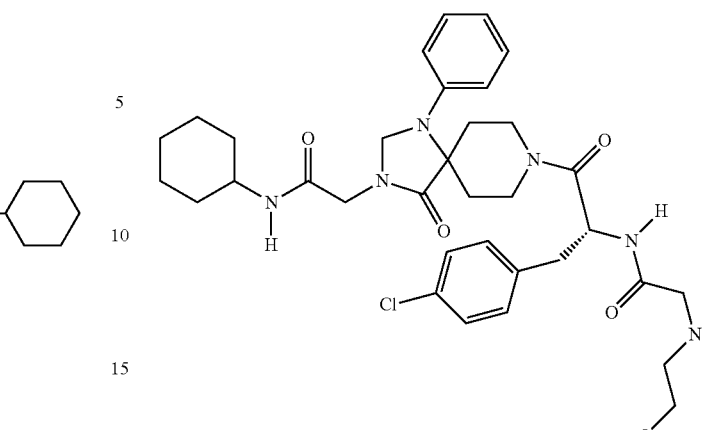

Inhibition at 1 µM (NPD-α-MSH)

| MC1-R | MC3-R | MC4-R | MC5-R |
|---|---|---|---|
| 11%* | 25%* | 55%* | 31%* |

Example 46

2-Benzylamino-N-[(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-acetamide The compound of Example 46 was synthesized by the methods of Scheme 4 and Scheme 6 described above, in which benzylamine was used. Following purification, the compound was tested as described above with the results shown.

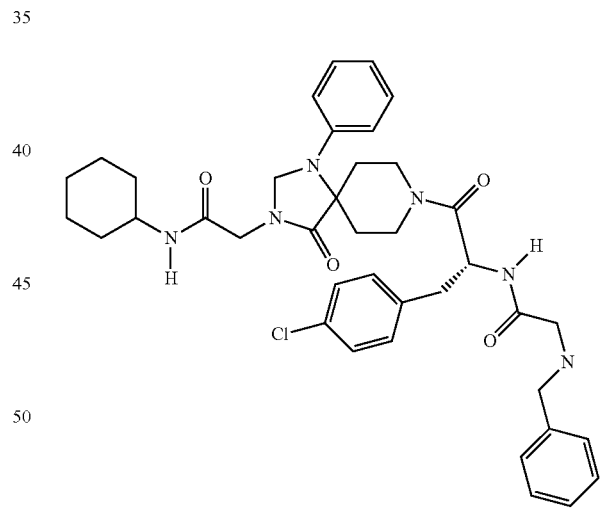

Inhibition at 1 µM (NPD-α-MSH)

| MC1-R | MC3-R | MC4-R | MC5-R |
|---|---|---|---|
| 12%* | 23%* | 45%* | 31%* |

Example 47

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-2-isopropylamino-acetamide The compound of Example 47 was synthesized by the methods of Scheme 4 and Scheme 6 described above, in which isopropylamine was used. Following purification, the compound was tested as described above with the results shown.

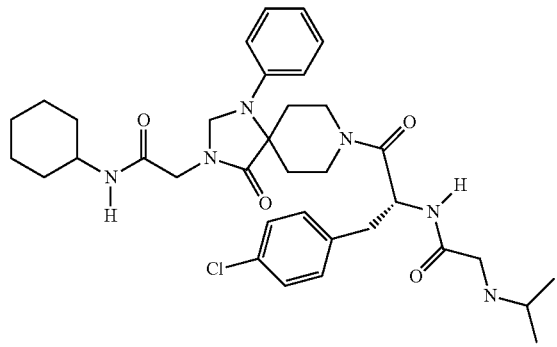

Inhibition at 1 µM (NPD-α-MSH)

| MC1-R | MC3-R | MC4-R | MC5-R |
|---|---|---|---|
| 20%* | 29%* | 65%* | 35%* |

Example 48

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-2-piperazin-1-yl-acetamide The compound of Example 48 was synthesized by the methods of Scheme 4 and Scheme 6 described above, in which piperazine was used. Following purification, the compound was tested as described above with the results shown.

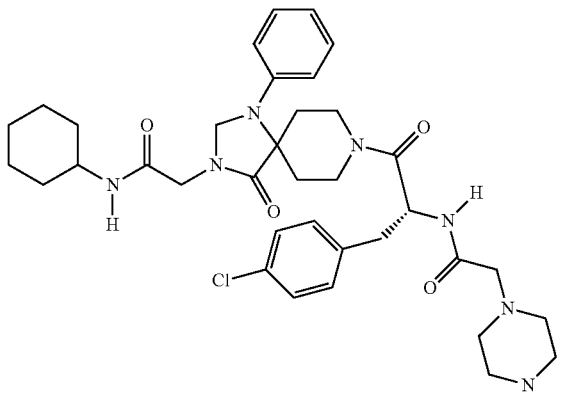

Inhibition at 1 µM (NPD-α-MSH)

| MC1-R | MC3-R | MC4-R | MC5-R |
|---|---|---|---|
| 7%* | 23%* | 27%* | 8%* |

Example 49

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-2-(4-methyl-piperazin-1-yl)-acetamide The compound of Example 49 was synthesized by the methods of Scheme 4 and Scheme 6 described above, in which methylpiperazine was used. Following purification, the compound was tested as described above with the results shown.

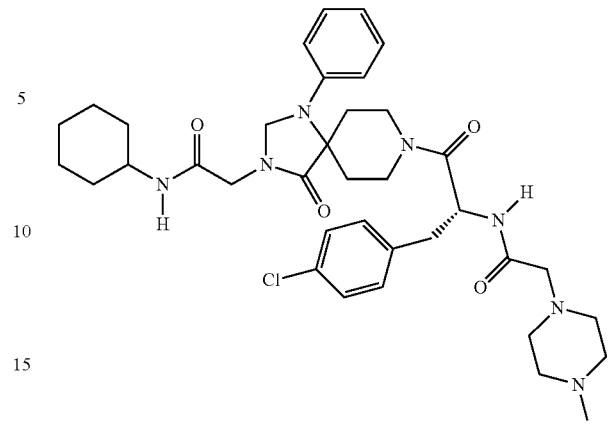

Inhibition at 1 µM (NPD-α-MSH)

| MC1-R | MC3-R | MC4-R | MC5-R |
|---|---|---|---|
| 12%* | 13%* | 25%* | 4%* |

Example 50

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-2-morpholin-4-yl-acetamide The compound of Example 50 was synthesized by the methods of Scheme 4 and Scheme 6 described above, in which morpholine was used. Following purification, the compound was tested as described above with the results shown.

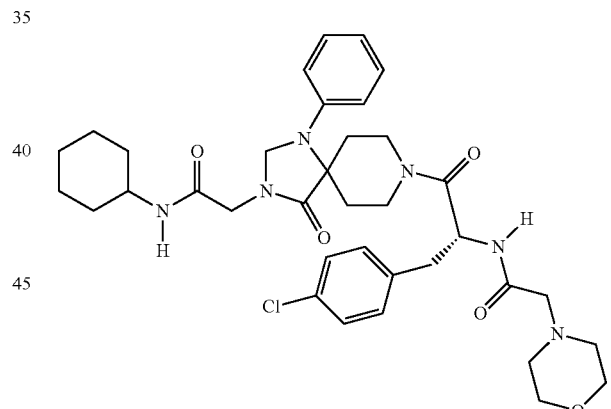

Inhibition at 1 µM (NPD-α-MSH)

| MC1-R | MC3-R | MC4-R | MC5-R |
|---|---|---|---|
| 4%* | 5%* | 20%* | 0%* |

Example 51

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-2-methylamino-acetamide The compound of Example 51 was synthesized by the methods of Scheme 4 and Scheme 6 described above, in which a 2.0 M solution of methylamine in THF was used. Following purification, the compound was tested as described above with the results shown.

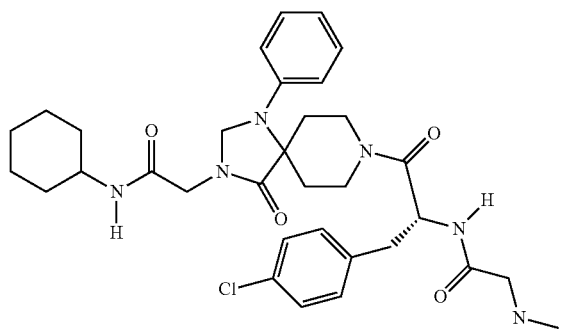

Inhibition at 1 µM (NPD-α-MSH)

| MC1-R | MC3-R | MC4-R | MC5-R |
|---|---|---|---|
| 4%* | 0%* | 46%* | 4%* |

Example 52

N-[(R)-1-(4-Chloro-benzyl)-2-(3-cyclohexylcarbam-
oylmethyl-4-oxo-1-phenyl-1,3,8-triaza-spiro[4.5]
dec-8-yl)-2-oxo-ethyl]-2-dimethylamino-acetamide The compound of Example 52 was synthesized by the methods of Scheme 4 and Scheme 6 described above, in which a 2.0 M solution of dimethylamine in THF was used. Following purification, the compound was tested as described above with the results shown.

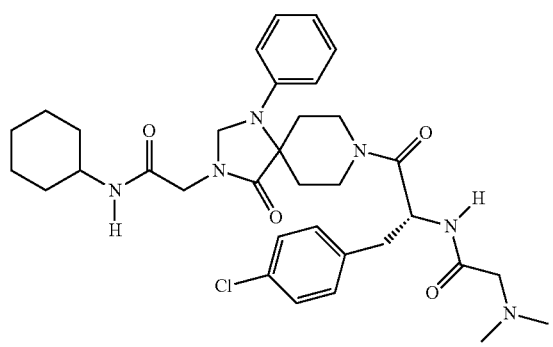

Inhibition at 1 µM (NPD-α-MSH)

| MC1-R | MC3-R | MC4-R | MC5-R |
|---|---|---|---|
| 6%* | 1%* | 47%* | 4%* |

Example 53

N-[(R)-1-(4-Chloro-benzyl)-2-(3-cyclohexylcarbam-
oylmethyl-4-oxo-1-phenyl-1,3,8-triaza-spiro[4.5]
dec-8-yl)-2-oxo-ethyl]-2-cyclohexylamino-aceta-
mide The compound of Example 53 was synthesized by the methods of Scheme 4 and Scheme 6 described above, in which cyclohexylamine was used. Following purification, the compound was tested as described above with the results shown.

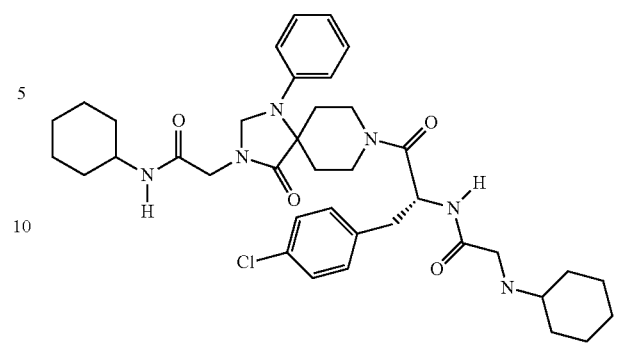

Inhibition at 1 µM (NPD-α-MSH)

| MC1-R | MC3-R | MC4-R | MC5-R |
|---|---|---|---|
| 12%* | 11%* | 55%* | 12%* |

Example 54

N-[(R)-1-(4-Chloro-benzyl)-2-(3-cyclohexylcarbam-
oylmethyl-4-oxo-1-phenyl-1,3,8-triaza-spiro[4.5]
dec-8-yl)-2-oxo-ethyl]-2-piperidin-1-yl-acetamide The compound of Example 54 was synthesized by the methods of Scheme 4 and Scheme 6 described above, in which piperidine was used. Following purification, the compound was tested as described above with the results shown.

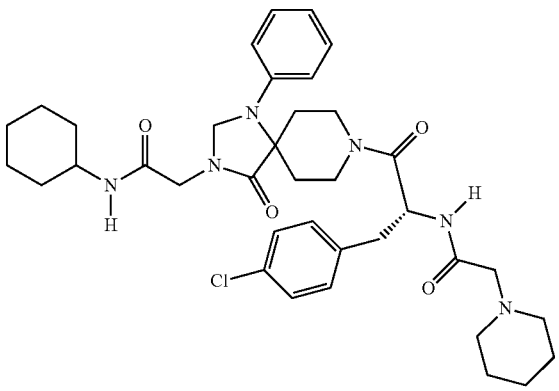

Inhibition at 1 µM (NPD-α-MSH)

| MC1-R | MC3-R | MC4-R | MC5-R |
|---|---|---|---|
| 16%* | 26%* | 49%* | 15%* |

Example 55

N-[(R)-1-(4-Chloro-benzyl)-2-(3-cyclohexylcarbam-
oylmethyl-4-oxo-1-phenyl-1,3,8-triaza-spiro[4.5]
dec-8-yl)-2-oxo-ethyl]-2-imidazol-1-yl-acetamide The compound of Example 55 was synthesized by the methods of Scheme 4 and Scheme 6 described above, in which imidazole was used. Following purification, the compound was tested as described above with the results shown.

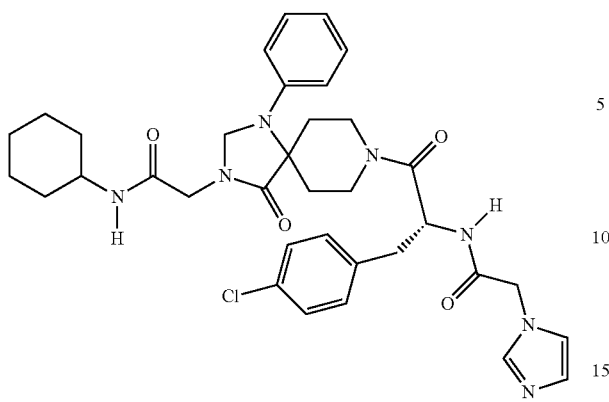

Inhibition at 1 µM (NPD-α-MSH)

| MC1-R | MC3-R | MC4-R | MC5-R |
|---|---|---|---|
| 0%* | 16%* | 35%* | 0%* |

Example 56

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-2-propylamino-acetamide The compound of Example 56 was synthesized by the methods of Scheme 4 and Scheme 6 described above, in which n-propylamine was used. Following purification, the compound was tested as described above with the results shown.

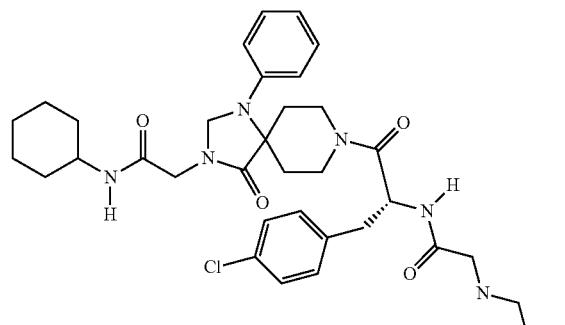

Inhibition at 1 µM (NPD-α-MSH)

| MC1-R | MC3-R | MC4-R | MC5-R |
|---|---|---|---|
| 7%* | 5%* | 53%* | 0%* |

Example 57

2-(2-Amino-ethylamino)-N-[(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-acetamide The compound of Example 57 was synthesized by the methods of Scheme 4 and Scheme 6 described above, in which N-Boc-ethylenediamine was used. Following purification, the compound was tested as described above with the results shown.

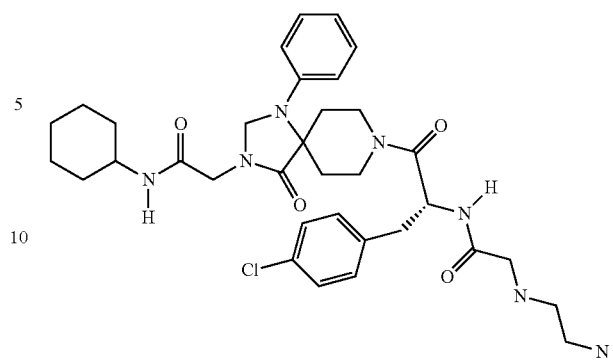

Inhibition at 1 µM (NPD-α-MSH)

| MC1-R | MC3-R | MC4-R | MC5-R |
|---|---|---|---|
| 7%* | 5%* | 53%* | 0%* |

Example 58

(R)-1,2,3,4-Tetrahydro-isoquinoline-3-carboxylic acid [(R)-1-(4-chloro-phenyl)-2-(3-cyclohexylcarbamoylmethyl-4-oxo-1-phenyl-1,3,8-triaza-spiro[4.5]dec-8-yl)-2-oxo-ethyl]-amide The compound of Example 58 was synthesized by the methods of Scheme 4 described above, in which Boc-(R)-1,2,3,4-tetrahydro-isoquinoline-3-carboxylic acid was used.

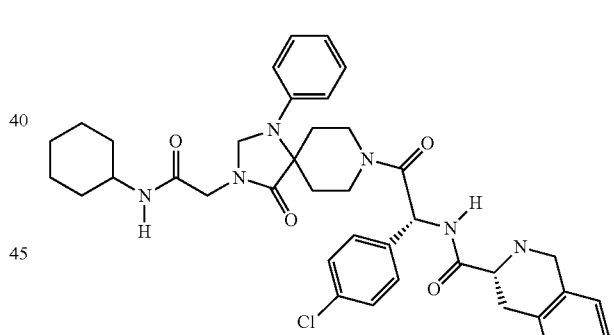

Example 59

(R)-1,2,3,4-Tetrahydro-isoquinoline-3-carboxylic acid [(S)-1-(4-chloro-phenyl)-2-(3-cyclohexylcarbamoylmethyl-4-oxo-1-phenyl-1,3,8-triaza-spiro[4.5]dec-8-yl)-2-oxo-ethyl]-amide The compound of Example 59 was synthesized by the methods of Scheme 4 described above, in which Boc-(R)-1,2,3,4-tetrahydro-isoquinoline-3-carboxylic acid was used. Following purification, the compound was tested as described above with the results shown.

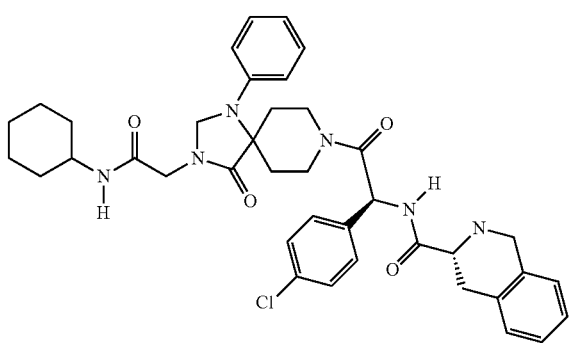

Example 60

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-2-oxo-1-phenyl-ethyl]-amide The compound of Example 60 was synthesized by the methods of Scheme 4 described above, in which Boc-(R)-1,2,3,4-tetrahydro-isoquinoline-3-carboxylic acid was used.

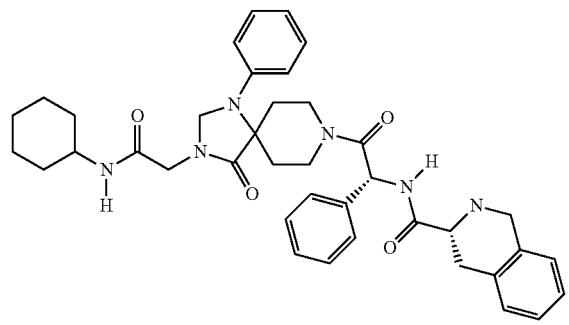

Example 61

(R)-1,2,3,4-Tetrahydro-isoquinoline-3-carboxylic acid [(S)-2-(3-cyclohexylcarbamoylmethyl-4-oxo-1-phenyl-1,3,8-triaza-spiro[4.5]dec-8-yl)-2-oxo-1-phenyl-ethyl]-amide The compound of Example 63 was synthesized by the methods of Scheme 4 described above, in which Boc-(R)-1,2,3,4-tetrahydro-isoquinoline-3-carboxylic acid was used. Following purification, the compound was tested as described above with the results shown.

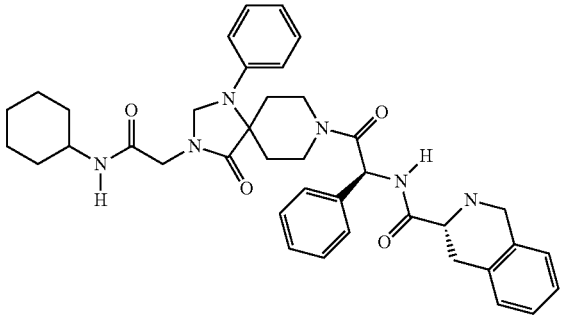

Inhibition at 1 μM (NDP-α-MSH)

| MC1-R | MC3-R | MC4-R | MC5-R |
|---|---|---|---|
| 33%* | 0%* | 18%* | 0%* |

Example 62

(R)-1,2,3,4-Tetrahydro-isoquinoline-3-carboxylic acid [(R)-1-(2-cyano-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 62 was synthesized by the methods of Scheme 4 described above, in which Boc-(R)-1,2,3,4-tetrahydro-isoquinoline-3-carboxylic acid was used. Following purification, the compound was tested as described above with the results shown.

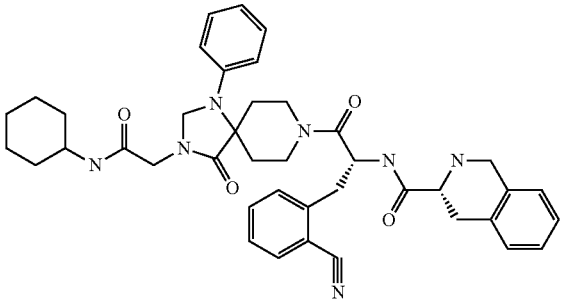

Inhibition at 1 μM (NDP-α-MSH)

| MC1-R | MC3-R | MC4-R | MC5-R |
|---|---|---|---|
| 4%* | 6%* | 0%* | 17%* |

Example 63

(R)-1,2,3,4-Tetrahydro-isoquinoline-3-carboxylic acid [(R)-1-(3-cyano-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 63 was synthesized by the methods of Scheme 4 described above, in which Boc-(R)-1,2,3,4-tetrahydro-isoquinoline-3-carboxylic acid was used. Following purification, the compound was tested as described above with the results shown.

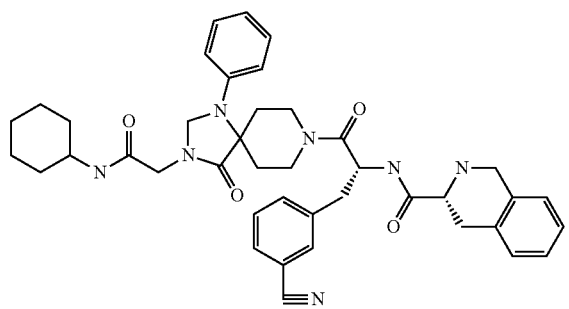

Inhibition at 1 μM (NDP-α-MSH)

| MC1-R | MC3-R | MC4-R | MC5-R |
|---|---|---|---|
| 0%* | 16%* | 34%* | 0%* |

Example 64

(R)-1,2,3,4-Tetrahydro-isoquinoline-3-carboxylic acid [(R)-1-(4-cyano-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 64 was synthesized by the methods of Scheme 4 described above, in which Boc-(R)-1,2,3,4-tetrahydro-isoquinoline-3-carboxylic acid was used. Following purification, the compound was tested as described above with the results shown.

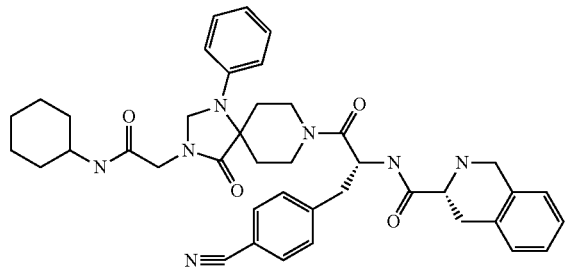

Inhibition at 1 μM (NDP-α-MSH)

| MC1-R | MC3-R | MC4-R | MC5-R |
|---|---|---|---|
| 0%* | 7%* | 36%* | 0%* |

Example 65

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(2-methyl-benzyl)-2-oxo-ethyl]-amide The compound of Example 65 was synthesized by the methods of Scheme 4 described above, in which Boc-(R)-1,2,3,4-tetrahydro-isoquinoline-3-carboxylic acid was used. Following purification, the compound was tested as described above with the results shown.

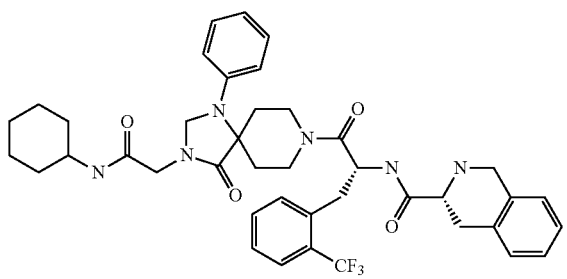

Inhibition at 1 μM (NDP-α-MSH)

| MC1-R | MC3-R | MC4-R | MC5-R |
|---|---|---|---|
| 0%* | 0%* | 39%* | 5%* |

Example 66

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(3-methyl-benzyl)-2-oxo-ethyl]-amide The compound of Example 66 was synthesized by the methods of Scheme 4 described above, in which Boc-(R)-1,2,3,4-tetrahydro-isoquinoline-3-carboxylic acid was used. Following purification, the compound was tested as described above with the results shown.

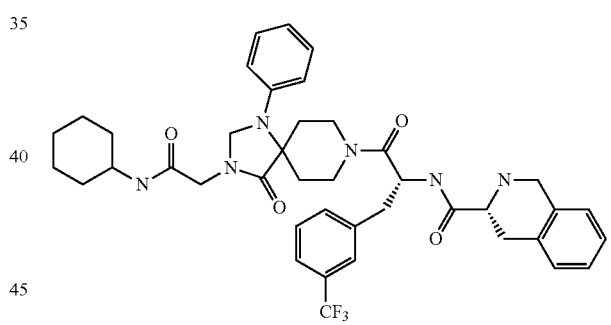

Inhibition at 1 μM (NDP-α-MSH)

| MC1-R | MC3-R | MC4-R | MC5-R |
|---|---|---|---|
| 0%* | 0%* | 35%* | 0%* |

Example 67

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(4-methyl-benzyl)-2-oxo-ethyl]-amide The compound of Example 67 was synthesized by the methods of Scheme 4 described above, in which Boc-(R)-1,2,3,4-tetrahydro-isoquinoline-3-carboxylic acid was used. Following purification, the compound was tested as described above with the results shown.

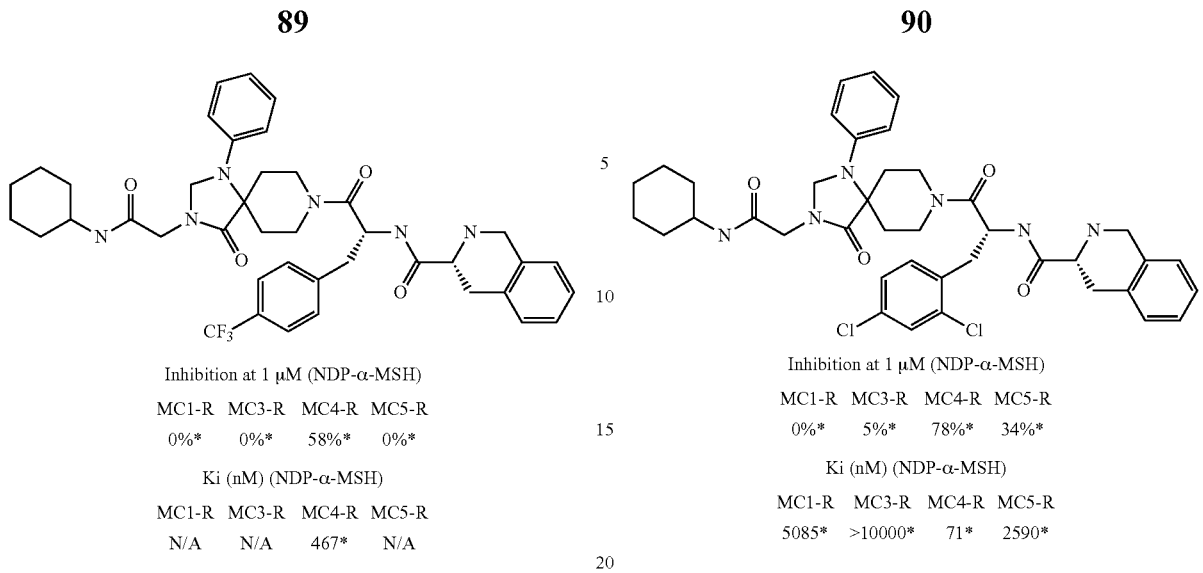

Inhibition at 1 μM (NDP-α-MSH)

| MC1-R | MC3-R | MC4-R | MC5-R |
|---|---|---|---|
| 0%* | 0%* | 58%* | 0%* |

Ki (nM) (NDP-α-MSH)

| MC1-R | MC3-R | MC4-R | MC5-R |
|---|---|---|---|
| N/A | N/A | 467* | N/A |

Example 68

(R)-1,2,3,4-Tetrahydro-isoquinoline-3-carboxylic acid [(R)-1-(2-chloro-benzyl)-2-(3-cyclohexylcarbamoylmethyl-4-oxo-1-phenyl-1,3,8-triaza-spiro[4.5]dec-8-yl)-2-oxo-ethyl]-amide The compound of Example 68 was synthesized by the methods of Scheme 4 described above, in which Boc-(R)-1,2,3,4-tetrahydro-isoquinoline-3-carboxylic acid was used. Following purification, the compound was tested as described above with the results shown.

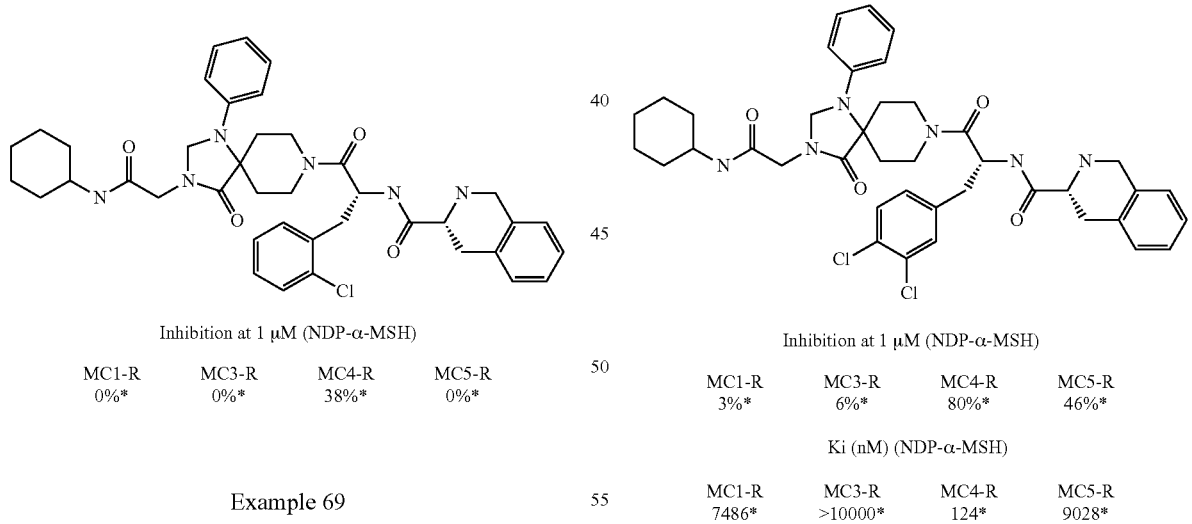

Inhibition at 1 μM (NDP-α-MSH)

| MC1-R | MC3-R | MC4-R | MC5-R |
|---|---|---|---|
| 0%* | 0%* | 38%* | 0%* |

Example 69

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(2,4-dichloro-benzyl)-2-oxo-ethyl]-amide The compound of Example 69 was synthesized by the methods of Scheme 4 described above, in which Boc-(R)-1,2,3,4-tetrahydro-isoquinoline-3-carboxylic acid was used. Following purification, the compound was tested as described above with the results shown.

Inhibition at 1 μM (NDP-α-MSH)

| MC1-R | MC3-R | MC4-R | MC5-R |
|---|---|---|---|
| 0%* | 5%* | 78%* | 34%* |

Ki (nM) (NDP-α-MSH)

| MC1-R | MC3-R | MC4-R | MC5-R |
|---|---|---|---|
| 5085* | >10000* | 71* | 2590* |

Example 70

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(3,4-dichloro-benzyl)-2-oxo-ethyl]-amide The compound of Example 70 was synthesized by the methods of Scheme 4 described above, in which Boc-(R)-1,2,3,4-tetrahydro-isoquinoline-3-carboxylic acid was used. Following purification, the compound was tested as described above with the results shown.

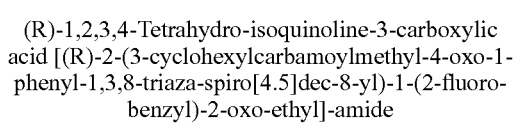

Inhibition at 1 μM (NDP-α-MSH)

| MC1-R | MC3-R | MC4-R | MC5-R |
|---|---|---|---|
| 3%* | 6%* | 80%* | 46%* |

Ki (nM) (NDP-α-MSH)

| MC1-R | MC3-R | MC4-R | MC5-R |
|---|---|---|---|
| 7486* | >10000* | 124* | 9028* |

Example 71

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(2-fluoro-benzyl)-2-oxo-ethyl]-amide The compound of Example 71 was synthesized by the methods of Scheme 4 described above, in which Boc-(R)-1, 2,3,4-tetrahydro-isoquinoline-3-carboxylic acid was used. Following purification, the compound was tested as described above with the results shown.

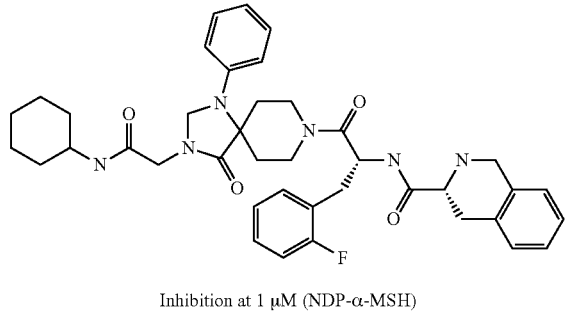

Inhibition at 1 μM (NDP-α-MSH)

| MC1-R | MC3-R | MC4-R | MC5-R |
|---|---|---|---|
| 13%* | 23%* | 26%* | 46%* |

Example 72

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(3-fluoro-benzyl)-2-oxo-ethyl]-amide The compound of Example 72 was synthesized by the methods of Scheme 4 described above, in which Boc-(R)-1,2,3,4-tetrahydro-isoquinoline-3-carboxylic acid was used. Following purification, the compound was tested as described above with the results shown.

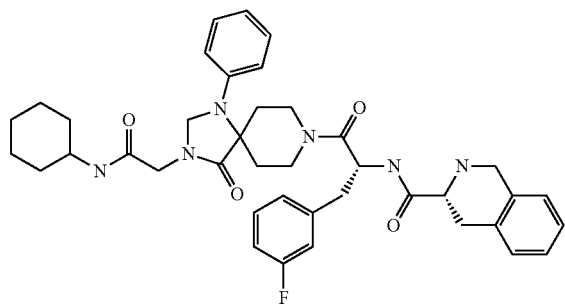

Example 73

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(4-fluoro-benzyl)-2-oxo-ethyl]-amide The compound of Example 73 was synthesized by the methods of Scheme 4 described above, in which Boc-(R)-1,2,3,4-tetrahydro-isoquinoline-3-carboxylic acid was used. Following purification, the compound was tested as described above with the results shown.

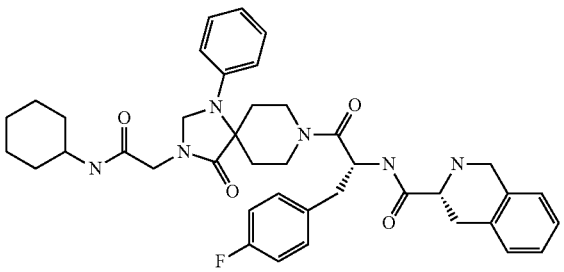

Inhibition at 1 μM (NDP-α-MSH)

| MC1-R | MC3-R | MC4-R | MC5-R |
|---|---|---|---|
| 0%* | 0%* | 50%* | 12%* |

Ki (nM) (NDP-α-MSH)

| MC1-R | MC3-R | MC4-R | MC5-R |
|---|---|---|---|
| N/A | N/A | 757* | N/A |

Example 74

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(3,5-difluoro-benzyl)-2-oxo-ethyl]-amide The compound of Example 74 was synthesized by the methods of Scheme 4 described above, in which Boc-(R)-1,2,3,4-tetrahydro-isoquinoline-3-carboxylic acid was used. Following purification, the compound was tested as described above with the results shown.

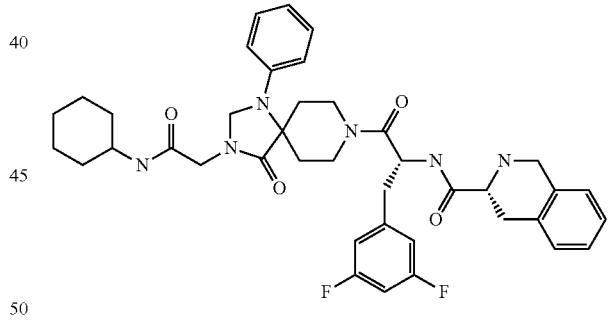

Inhibition at 1 μM (NDP-α-MSH)

| MC1-R | MC3-R | MC4-R | MC5-R |
|---|---|---|---|
| 0%* | 0%* | 26%* | 0%* |

Example 75

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-2-oxo-1-pyridin-3-ylmethyl-ethyl]-amide The compound of Example 75 was synthesized by the methods of Scheme 4 described above, in which Boc-(R)-1,2,3,4-tetrahydro-isoquinoline-3-carboxylic acid was used.

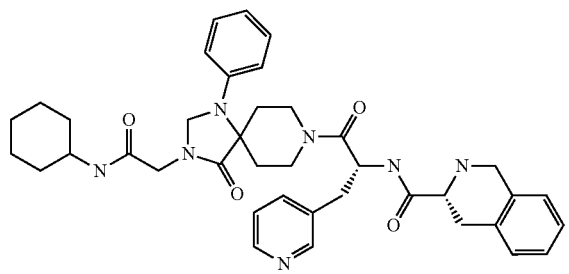

Example 76

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-2-oxo-1-pyridin-4-ylmethyl-ethyl]-amide The compound of Example 76 was synthesized by the methods of Scheme 4 described above, in which Boc-(R)-1,2,3,4-tetrahydro-isoquinoline-3-carboxylic acid was used. Following purification, the compound was tested as described above with the results shown.

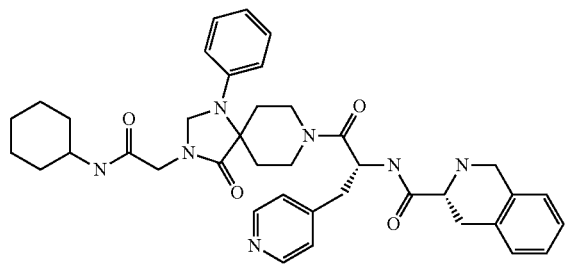

Example 77

(R)-1,2,3,4-Tetrahydro-isoquinoline-3-carboxylic acid [(R)-2-(3-cyclohexylcarbamoylmethyl-4-oxo-1-phenyl-1,3,8-triaza-spiro[4.5]dec-8-yl)-1-(3-methoxy-benzyl)-2-oxo-ethyl]-amide The compound of Example 77 was synthesized by the methods of Scheme 4 described above, in which Boc-(R)-1,2,3,4-tetrahydro-isoquinoline-3-carboxylic acid was used. Following purification, the compound was tested as described above with the results shown.

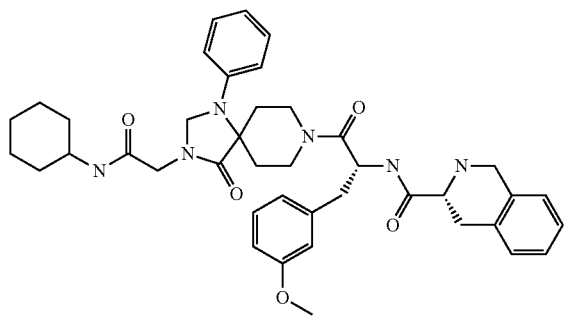

Inhibition at 1 µM (NDP-α-MSH)

| MC1-R | MC3-R | MC4-R | MC5-R |
|---|---|---|---|
| 0%* | 0%* | 30%* | 93%* |

Example 78

4-Amino-N-[(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-butyramide The compound of Example 78 was synthesized by the methods of Scheme 4 described above, in which Boc-4-aminobutyric acid was used. Following purification, the compound was tested as described above with the results shown.

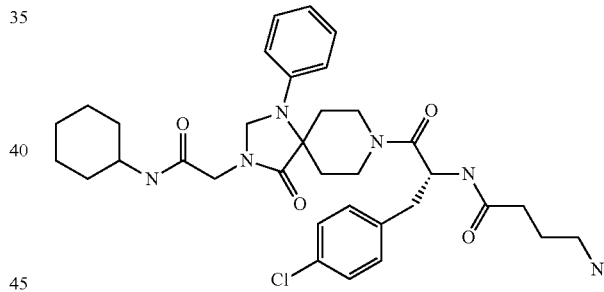

Inhibition at 1 µM (NDP-α-MSH)

| MC1-R | MC3-R | MC4-R | MC5-R |
|---|---|---|---|
| 25%* | 0%* | 57%* | 91%* |

Ki (nM) (NDP-α-MSH)

| MC1-R | MC3-R | MC4-R | MC5-R |
|---|---|---|---|
| 203* | 2209* | 165* | 771* |

Example 79

3-Amino-N-[(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-propionamide The compound of Example 79 was synthesized by the methods of Scheme 4 described above, in which Boc-3-aminoproprionic acid was used. Following purification, the compound was tested as described above with the results shown.

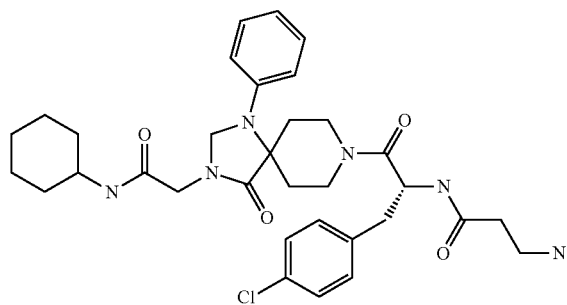

Inhibition at 1 μM (NDP-α-MSH)

| MC1-R | MC3-R | MC4-R | MC5-R |
|---|---|---|---|
| 13%* | 10%* | 55%* | 52%* |

Example 80

2-{8-[(R)-3-(4-Chloro-phenyl)-2-(4-dimethylami-nomethyl-benzenesulfonylamino)-propionyl]-4-oxo-1-phenyl-1,3,8-triaza-spiro[4.5]dec-3-yl}-N-cyclo-hexyl-acetamide The compound of Example 80 was synthesized by the methods of Scheme 4 and Scheme 6 described above, in which a 2.0 M solution of dimethylamine in THF was used.

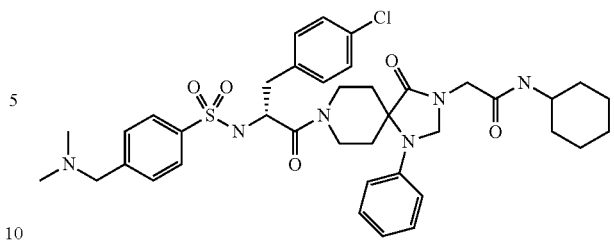

Example 81

2-{8-[(R)-3-(4-Chloro-phenyl)-2-(4-ethylaminom-ethyl-benzenesulfonylamino)-propionyl]-4-oxo-1-phenyl-1,3,8-triaza-spiro[4.5]dec-3-yl}-N-cyclo-hexyl-acetamide The compound of Example 81 was synthesized by the methods of Scheme 4 and Scheme 6 described above, in which a 2.0 M solution of ethylamine in THF was used.

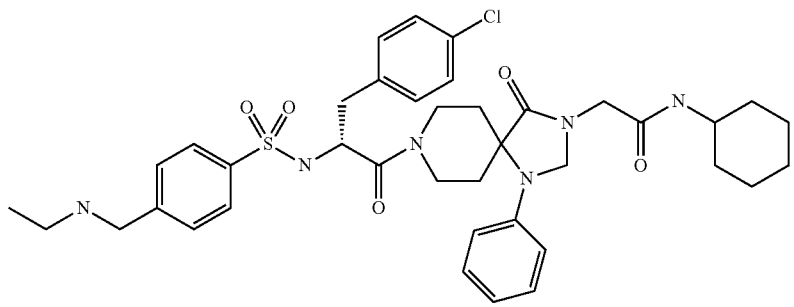

Example 82

2-(8-{(R)-3-(4-Chloro-phenyl)-2-[4-(isopropy-lamino-methyl)-benzenesulfonylamino]-propionyl}-4-oxo-1-phenyl-1,3,8-triaza-spiro[4.5]dec-3-yl)-N-cyclohexyl-acetamide The compound of Example 82 was synthesized by the methods of Scheme 4 and Scheme 6 described above, in which isopropylamine was used.

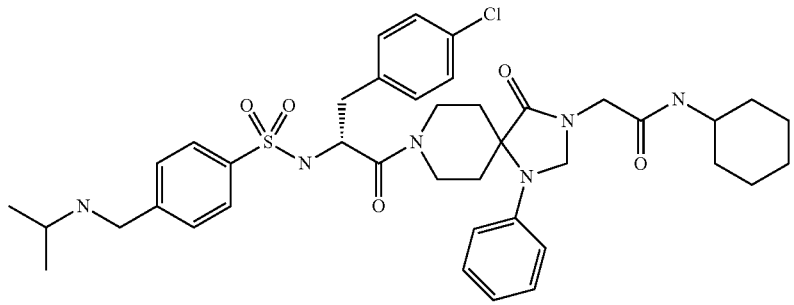

Example 83

2-{8-[(R)-2-[4-(Benzylamino-methyl)-benzenesulfo-nylamino]-3-(4-chloro-phenyl)-propionyl]-4-oxo-1-phenyl-1,3,8-triaza-spiro[4.5]dec-3-yl}-N-cyclo-hexyl-acetamide The compound of Example 83 was synthesized by the methods of Scheme 4 and Scheme 6 described above, in which benzylamine was used.

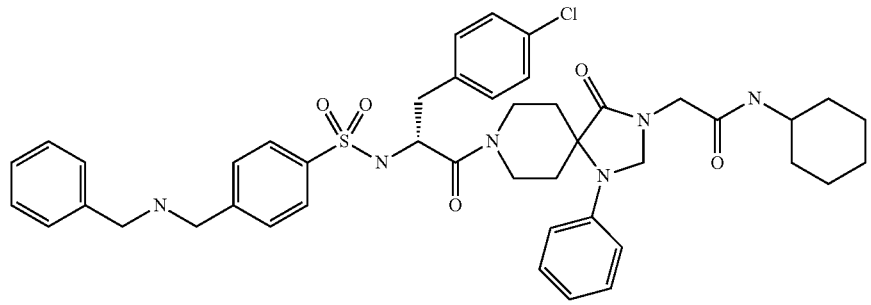

Example 84

2-{8-[(R)-3-(4-Chloro-phenyl)-2-(4-piperazin-1-ylmethyl-benzenesulfonylamino)-propionyl]-4-oxo-1-phenyl-1,3,8-triaza-spiro[4.5]dec-3-yl}-N-cyclo-hexyl-acetamide The compound of Example 84 was synthesized by the methods of Scheme 4 and Scheme 6 described above, in which piperazine was used.

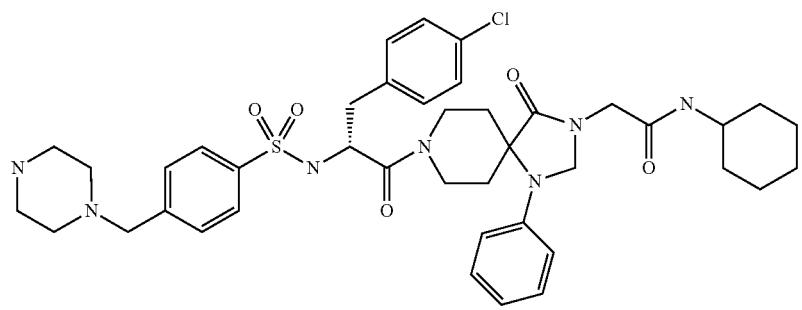

Example 85

2-(8-{(R)-3-(4-Chloro-phenyl)-2-[4-(4-methyl-piper-azin-1-ylmethyl)-benzenesulfonylamino]-propio-nyl}-4-oxo-1-phenyl-1,3,8-triaza-spiro[4.5]dec-3-yl)-N-cyclohexyl-acetamide The compound of Example 85 was synthesized by the methods of Scheme 4 and Scheme 6 described above, in which methylpiperazine was used.

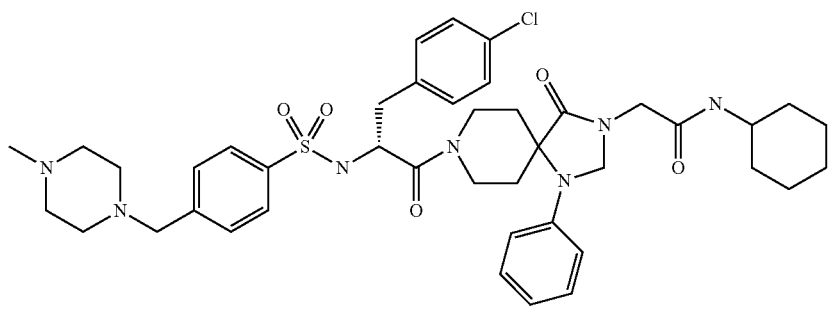

Example 86

2-[8-((R)-3-(4-Chloro-phenyl)-2-{4-[(2-hydroxy-ethylamino)-methyl]-benzenesulfonylamino}-propionyl)-4-oxo-1-phenyl-1,3,8-triaza-spiro[4.5]dec-3-yl]-N-cyclohexyl-acetamide The compound of Example 86 was synthesized by the methods of Scheme 4 and Scheme 6 described above, in which aminoethanol was used.

Example 88

2-{8-[(R)-3-(4-Chloro-phenyl)-2-(4-methylaminomethyl-benzenesulfonylamino)-propionyl]-4-oxo-1-phenyl-1,3,8-triaza-spiro[4.5]dec-3-yl}-N-cyclohexyl-acetamide The compound of Example 88 was synthesized by the methods of Scheme 4 and Scheme 6 described above, in which benzylamine was used.

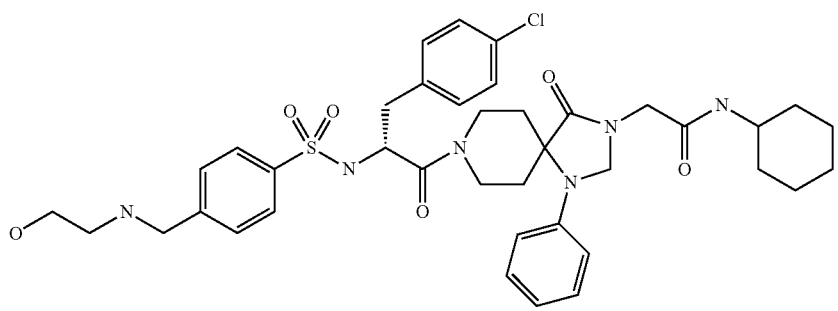

Example 87

2-[8-((R)-3-(4-Chloro-phenyl)-2-{4-[(2-methoxy-ethylamino)-methyl]-benzenesulfonylamino}-propionyl)-4-oxo-1-phenyl-1,3,8-triaza-spiro[4.5]dec-3-yl]-N-cyclohexyl-acetamide The compound of Example 87 was synthesized by the methods of Scheme 4 and Scheme 6 described above, in which methoxyethylamine was used.

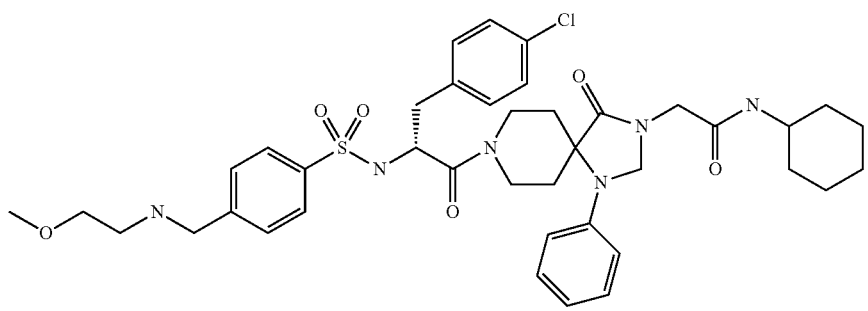

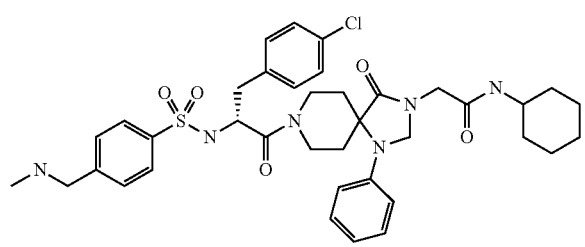

Example 89

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-4-methylaminomethyl-benzamide The compound of Example 89 was synthesized by the methods of Scheme 4 and Scheme 6 described above, in which a 2.0 M solution of methylamine in THF was used. Following purification, the compound was tested as described above with the results shown.

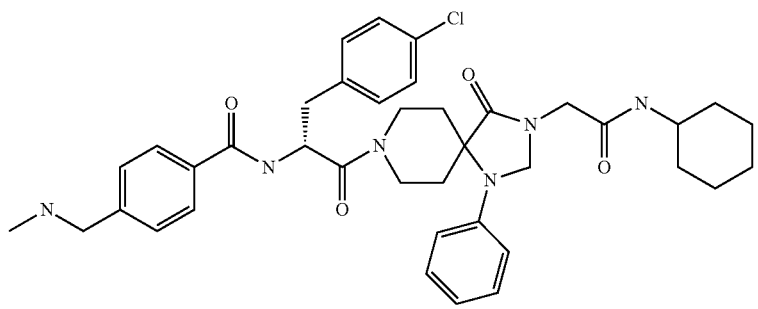

Inhibition at 1 µM (NDP-α-MSH)

| MC1-R | MC3-R | MC4-R | MC5-R |
|---|---|---|---|
| 0%* | 0%* | 33%* | N/A |

Example 90

N-[(R)-1-(4-Chloro-benzyl)-2-(3-cyclohexylcarbamoylmethyl-4-oxo-1-phenyl-1,3,8-triaza-spiro[4,5]dec-8-yl)-2-oxo-ethyl]-4-ethylaminomethyl-benzamide The compound of Example 90 was synthesized by the methods of Scheme 4 and Scheme 6 described above, in which a 2.0 M solution of ethylamine in THF was used.
Following purification, the compound was tested as described above with the results shown.

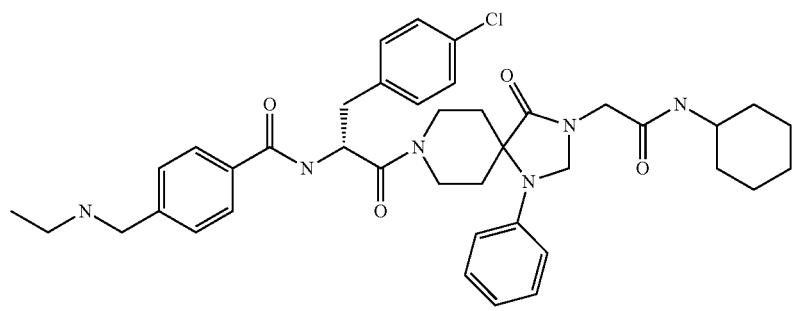

Inhibition at 1 µM (NDP-α-MSH)

| MC1-R | MC3-R | MC4-R | MC5-R |
|---|---|---|---|
| 33%* | 10%* | 38%* | N/A |

Example 91

4-(Benzylamino-methyl)-N-[(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-benzamide The compound of Example 91 was synthesized by the methods of Scheme 4 and Scheme 6 described above, in which benzylamine was used. Following purification, the compound was tested as described above with the results shown.

Example 93

N-[(R)-1-(4-Chloro-benzyl)-2-(3-cyclohexylcarbamoylmethyl-4-oxo-1-phenyl-1,3,8-triaza-spiro[4.5]-dec-8-yl)-2-oxo-ethyl]-4-[(2-hydroxy-ethylamino)-methyl]-benzamide The compound of Example 93 was synthesized by the methods of Scheme 4 and Scheme 6 described above, in which aminoethanol was used. Following purification, the compound was tested as described above with the results shown.

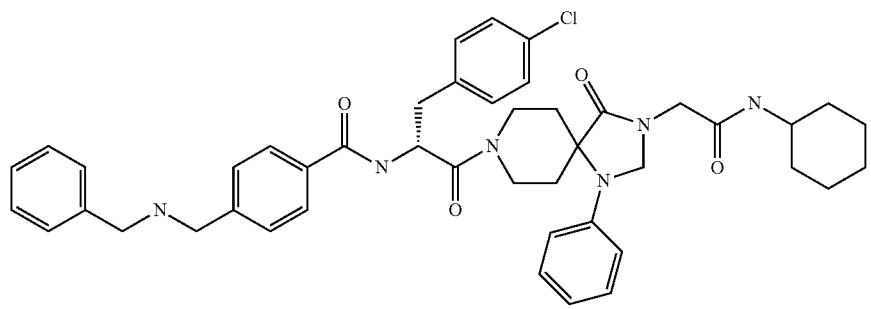

Inhibition at 1 μM (NDP-α-MSH)

| MC1-R | MC3-R | MC4-R | MC5-R |
|---|---|---|---|
| 16%* | 0%* | 47%* | N/A |

Example 92

N-[(R)-1-(4-Chloro-benzyl)-2-(3-cyclohexylcarbamoylmethyl-4-oxo-1-phenyl-1,3,8-triaza-spiro[4.5]-dec-8-yl)-2-oxo-ethyl]-4-(4-methyl-piperazin-1-ylmethyl)-benzamide The compound of Example 92 was synthesized by the methods of Scheme 4 and Scheme 6 described above, in which N-methyl-piperazine was used. Following purification, the compound was tested as described above with the results shown.

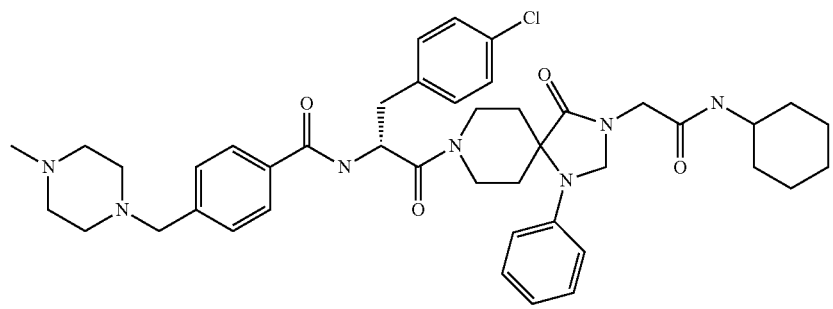

Inhibition at 1 μM (NDP-α-MSH)

| MC1-R | MC3-R | MC4-R | MC5-R |
|---|---|---|---|
| 0%* | 0%* | 27%* | N/A |

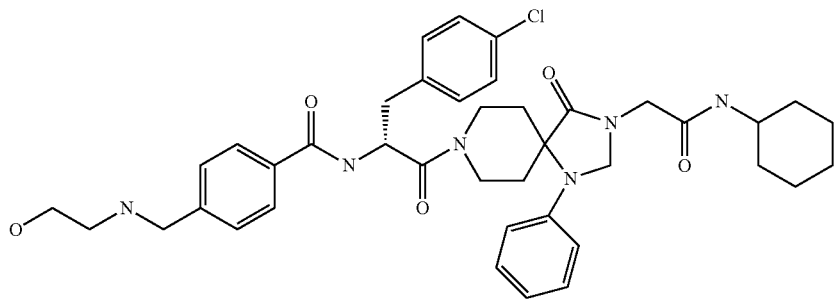

Inhibition at 1 µM (NDP-α–MSH)

| MC1-R | MC3-R | MC4-R | MC5-R |
|---|---|---|---|
| 0%* | 1%* | 41%* | N/A |

Example 94

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-4-dimethylaminomethyl-benzamide The compound of Example 94 was synthesized by the methods of Scheme 4 and Scheme 6 described above, in which a 2.0 M solution of dimethylamine in THF was used. Following purification, the compound was tested as described above with the results shown.

Example 95

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-4-(isopropylamino-methyl)-benzamide The compound of Example 95 was synthesized by the methods of Scheme 4 and Scheme 6 described above, in which isopropylamine was used. Following purification, the compound was tested as described above with the results shown.

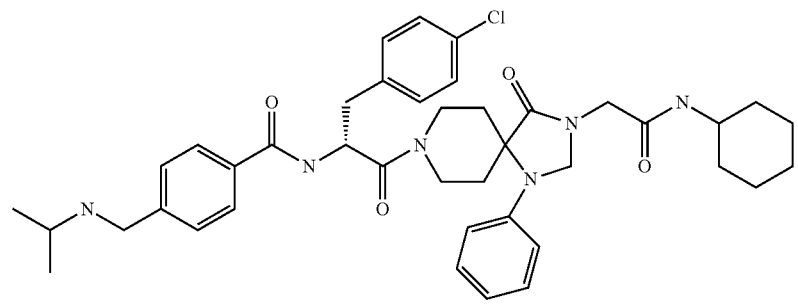

Inhibition at 1 µM (NDP-α–MSH)

| MC1-R | MC3-R | MC4-R | MC5-R |
|---|---|---|---|
| 21%* | 0%* | 50%* | N/A |

Example 96

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-4-piperazin-1-ylmethyl-benzamide The compound of Example 96 was synthesized by the methods of Scheme 4 and Scheme 6 described above, in which piperazine was used. Following purification, the compound was tested as described above with the results shown.

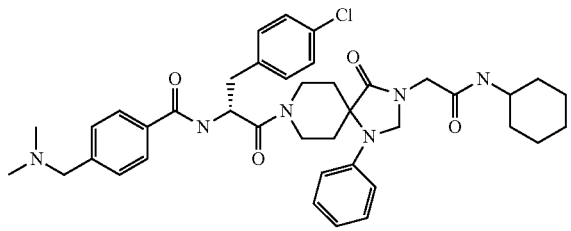

Inhibition at 1 µM (NDP-α–MSH)

| MC1-R | MC3-R | MC4-R | MC5-R |
|---|---|---|---|
| 0%* | 1%* | 48%* | N/A |

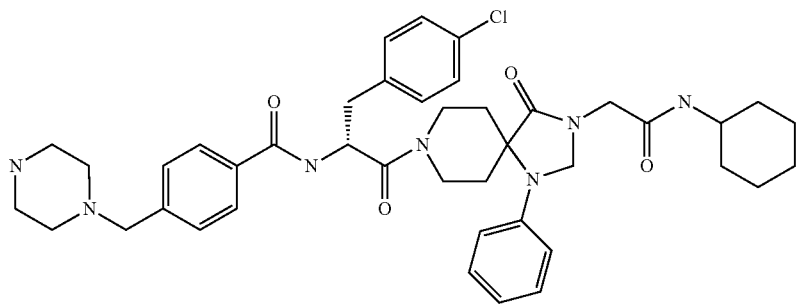

Inhibition at 1 µM (NDP-α-MSH)

| MC1-R | MC3-R | MC4-R | MC5-R |
|---|---|---|---|
| 0%* | 12%* | 36%* | N/A |

Example 97

N-[(R)-1-(4-Chloro-benzyl)-2-(3-cyclohexylcarbamoylmethyl-4-oxo-1-phenyl-1,3,8-triaza-spiro[4.5]dec-8-yl)-2-oxo-ethyl]-4-[(2-methoxy-ethylamino)-methyl]-benzamide The compound of Example 97 was synthesized by the methods of Scheme 4 and Scheme 6 described above, in which methoxyethylamine was used. Following purification, the compound was tested as described above with the results shown.

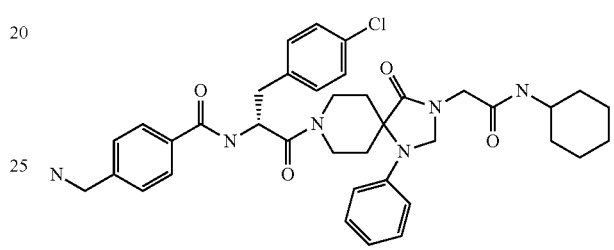

Inhibition at 1 µM (NDP-α-MSH)

| MC1-R | MC3-R | MC4-R | MC5-R |
|---|---|---|---|
| 0%* | 14%* | 47%* | N/A |

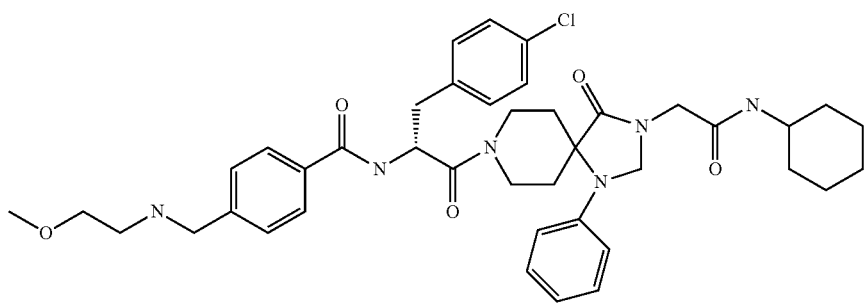

Inhibition at 1 µM (NDP-α-MSH)

| MC1-R | MC3-R | MC4-R | MC5-R |
|---|---|---|---|
| 0%* | 15%* | 52%* | N/A |

Example 98

4-Aminomethyl-N-[(R)-1-(4-chloro-benzyl)-2-(3-cyclohexylcarbamoylmethyl-4-oxo-1-phenyl-1,3,8-triaza-spiro[4.5]dec-8-yl)-2-oxo-ethyl]-benzamide The compound of Example 98 was synthesized by the methods of Scheme 4 and Scheme 6 described above, in which a 0.5 M solution of ammonia in 1,4-dioxane was used. Following purification, the compound was tested as described above with the results shown.

Example 99

2-{8-[(R)-2-(4-Aminomethyl-benzenesulfonylamino)-3-(4-chloro-phenyl)-propionyl]-4-oxo-1-phenyl-1,3,8-triaza-spiro[4.5]dec-3-yl}-N-cyclohexyl-acetamide The compound of Example 99 was synthesized by the methods of Scheme 4 and Scheme 6 described above, in which a 0.5 M solution of ammonia in 1,4-dioxane was used. Following purification, the compound was tested as described above with the results shown.

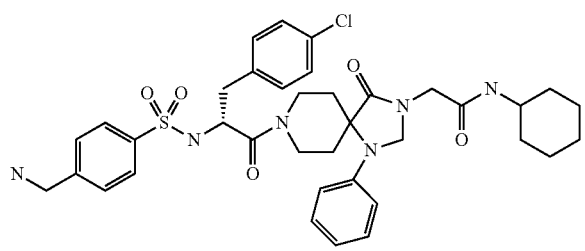

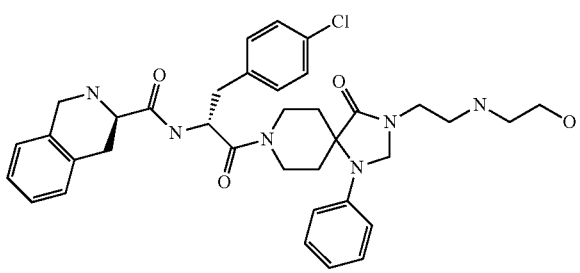

Inhibition at 1 µM (NDP-α-MSH)

| MC1-R | MC3-R | MC4-R | MC5-R |
|---|---|---|---|
| 0%* | 15%* | 12%* | N/A |

Example 100

(R)-1,2,3,4-Tetrahydro-isoquinoline-3-carboxylic acid {(R)-1-(4-chloro-benzyl)-2-[3-(2-methylamino-ethyl)-4-oxo-1-phenyl-1,3,8-triaza-spiro[4.5]dec-8-yl]-2-oxo-ethyl}-amide The compound of Example 100 was synthesized by the methods of Scheme 2 described above, in which a 2.0 M solution of methylamine in THF was used. Following purification, the compound was tested as described above with the results shown.

Inhibition at 1 µM (NDP-α-MSH)

| MC1-R | MC3-R | MC4-R | MC5-R |
|---|---|---|---|
| 0%* | 0%* | 74%* | 19%* |

Ki (nM) (NDP-α-MSH)

| MC1-R | MC3-R | MC4-R | MC5-R |
|---|---|---|---|
| N/A | N/A | 267* | N/A |

Example 102

(R)-1,2,3,4-Tetrahydro-isoquinoline-3-carboxylic acid [(R)-2-[3-(2-benzylamino-ethyl)-4-oxo-1-phenyl-1,3,8-triaza-spiro[4.5]dec-8-yl]-1-(4-chloro-benzyl)-2-oxo-ethyl]-amide The compound of Example 102 was synthesized by the methods of Scheme 2 described above, in which benzylamine was used. Following purification, the compound was tested as described above with the results shown.

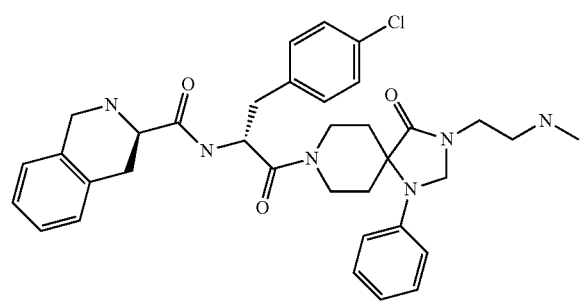

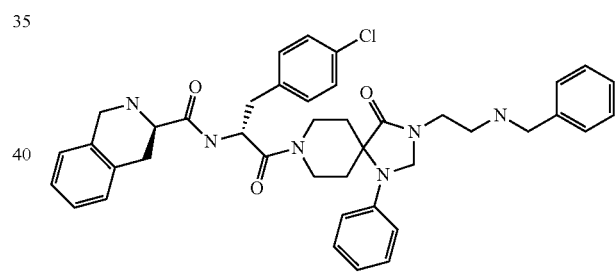

Inhibition at 1µM (NDP-α-MSH)

| MC1-R | MC3-R | MC4-R | MC5-R |
|---|---|---|---|
| 0%* | 0%* | 52%* | 6%* |

Ki (nM) (NDP-α-MSH)

| MC1-R | MC3-R | MC4-R | MC5-R |
|---|---|---|---|
| N/A | N/A | 535* | N/A |

Example 101

(R)-1,2,3,4-Tetrahydro-isoquinoline-3-carboxylic acid ((R)-1-(4-chloro-benzyl)-2-{3-[2-(2-hydroxy-ethylamino)-ethyl]-4-oxo-1-phenyl-1,3,8-triaza-spiro[4.5]dec-8-yl}-2-oxo-ethyl)-amide The compound of Example 101 was synthesized by the methods of Scheme 2 described above, in which aminoethanol was used. Following purification, the compound was tested as described above with the results shown.

Inhibition at 1 µM (NDP-α-MSH)

| MC1-R | MC3-R | MC4-R | MC5-R |
|---|---|---|---|
| 2%* | 0%* | 63%* | 15%* |

Ki (nM) (NDP-α-MSH)

| MC1-R | MC3-R | MC4-R | MC5-R |
|---|---|---|---|
| N/A | N/A | 357* | N/A |

Example 103

(R)-1,2,3,4-Tetrahydro-isoquinoline-3-carboxylic acid [(R)-2-[3-(2-amino-ethyl)-4-oxo-1-phenyl-1,3,8-triaza-spiro[4.5]dec-8-yl]-1-(4-chloro-benzyl)-2-oxo-ethyl]-amide The compound of Example 103 was synthesized by the methods of Scheme 2 described above, in which a 7 M solution of ammonia in methanol was used. Following purification, the compound was tested as described above with the results shown.

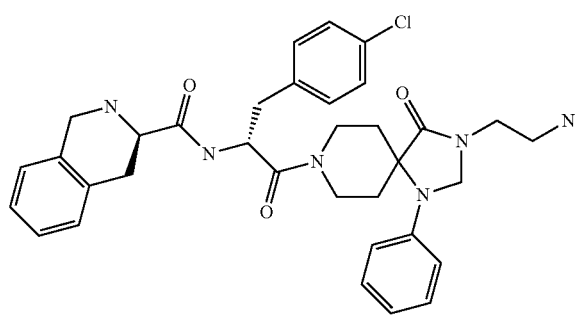

Inhibition at 1 μM (NDP-α-MSH)

| MC1-R | MC3-R | MC4-R | MC5-R |
|---|---|---|---|
| 5%* | 13%* | 72%* | 14%* |

Ki (nM) (NDP-α-MSH)

| MC1-R | MC3-R | MC4-R | MC5-R |
|---|---|---|---|
| N/A | N/A | 189* | N/A |

Example 104

(R)-1,2,3,4-Tetrahydro-isoquinoline-3-carboxylic acid {(R)-1-(4-chloro-benzyl)-2-oxo-2-[4-oxo-1-phenyl-3-(2-propylamino-ethyl)-1,3,8-triaza-spiro[4.5]dec-8-yl]-ethyl}-amide The compound of Example 104 was synthesized by the methods of Scheme 2 described above, in which n-propylamine was used. Following purification, the compound was tested as described above with the results shown.

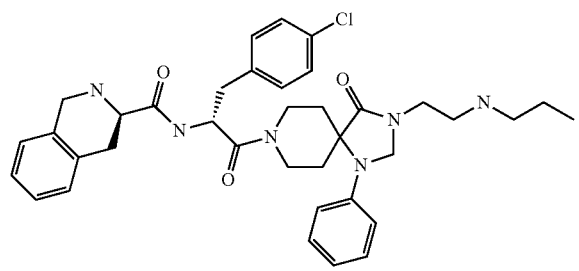

Inhibition at 1 μM (NDP-α-MSH)

| MC1-R | MC3-R | MC4-R | MC5-R |
|---|---|---|---|
| 0%* | 12%* | 77%* | 21%* |

Ki (nM) (NDP-α-MSH)

| MC1-R | MC3-R | MC4-R | MC5-R |
|---|---|---|---|
| N/A | N/A | 146* | N/A |

Example 105

(R)-1,2,3,4-Tetrahydro-isoquinoline-3-carboxylic acid {(R)-1-(4-chloro-benzyl)-2-oxo-2-[4-oxo-1-phenyl-3-(2-piperidin-1-yl-ethyl)-1,3,8-triaza-spiro[4.5]dec-8-yl]-ethyl}-amide The compound of Example 105 was synthesized by the methods of Scheme 2 described above, in which piperidine was used. Following purification, the compound was tested as described above with the results shown.

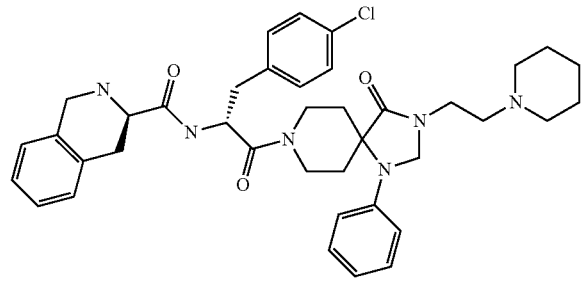

Inhibition at 1 μM (NDP-α-MSH)

| MC1-R | MC3-R | MC4-R | MC5-R |
|---|---|---|---|
| 0%* | 9%* | 62%* | 12%* |

Ki (nM) (NDP-α-MSH)

| MC1-R | MC3-R | MC4-R | MC5-R |
|---|---|---|---|
| 2090* | N/A | 430* | N/A |

Example 106

(R)-1,2,3,4-Tetrahydro-isoquinoline-3-carboxylic acid {(R)-1-(4-chloro-benzyl)-2-[3-(2-morpholin-4-yl-ethyl)-4-oxo-1-phenyl-1,3,8-triaza-spiro[4.5]dec-8-yl]-2-oxo-ethyl}-amide The compound of Example 106 was synthesized by the methods of Scheme 2 described above, in which morpholine was used. Following purification, the compound was tested as described above with the results shown.

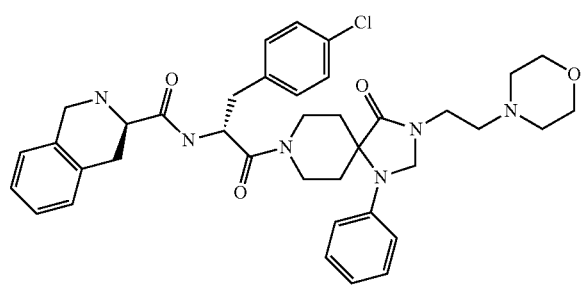

Inhibition at 1 μM (NDP-α-MSH)

| MC1-R | MC3-R | MC4-R | MC5-R |
|---|---|---|---|
| 2%* | 13%* | 63%* | 9%* |

Ki (nM) (NDP-α-MSH)

| MC1-R | MC3-R | MC4-R | MC5-R |
|---|---|---|---|
| >10000* | N/A | 342* | N/A |

Example 107

(R)-1,2,3,4-Tetrahydro-isoquinoline-3-carboxylic acid {(R)-1-(4-chloro-benzyl)-2-[3-(2-hydroxy-ethyl)-4-oxo-1-phenyl-1,3,8-triaza-spiro[4.5]dec-8-yl]-2-oxo-ethyl}-amide The compound of Example 107 was synthesized by the methods of Scheme 2 described above, except that no activation and replacement of the hydroxyl group was performed. Following purification, the compound was tested as described above with the results shown.

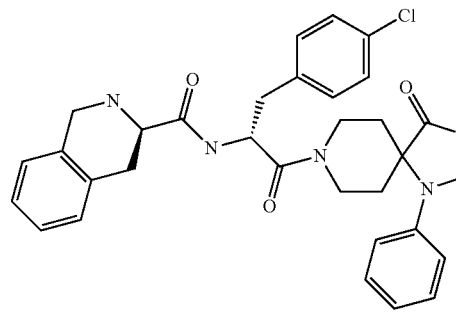

Inhibition at 1 μM (NDP-α-MSH)

| MC1-R | MC3-R | MC4-R | MC5-R |
|---|---|---|---|
| 0%* | 11%* | 67%* | 14%* |

Ki (nM) (NDP-α-MSH)

| MC1-R | MC3-R | MC4-R | MC5-R |
|---|---|---|---|
| 8943* | N/A | 261* | N/A |

Example 108

(R)-1,2,3,4-Tetrahydro-isoquinoline-3-carboxylic acid [(R)-2-[3-(2-acetylamino-ethyl)-4-oxo-1-phenyl-1,3,8-triaza-spiro[4.5]dec-8-yl]-1-(4-chloro-benzyl)-2-oxo-ethyl]-amide The compound of Example 108 was synthesized by the methods of Scheme 2 described above, in which first a 7N solution of ammonia in methanol, then acetic anhydride was used. Following purification, the compound was tested as described above with the results shown.

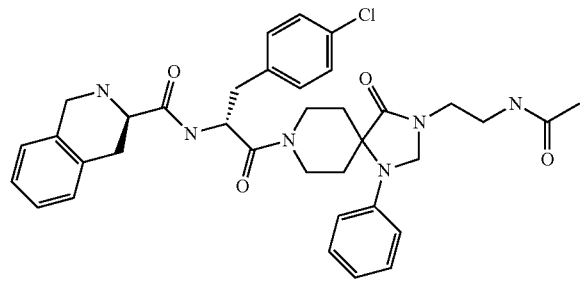

Inhibition at 1 μM (NDP-α-MSH)

| MC1-R | MC3-R | MC4-R | MC5-R |
|---|---|---|---|
| 2%* | 14%* | 76%* | N/A |

Ki (nM) (NDP-α-MSH)

| MC1-R | MC3-R | MC4-R | MC5-R |
|---|---|---|---|
| N/A | N/A | 370* | N/A |

Example 109

(1-(3-Chloro-phenyl)-8-{(R)-3-(4-chloro-phenyl)-2-[((R)-1,2,3,4-tetrahydro-isoquinoline-3-carbonyl)-amino]-propionyl}-4-oxo-1,3,8-triaza-spiro[4.5]dec-3-yl)-acetic acid methyl ester The following compound was synthesized according to the methods in Schemes 5 and 3, except that the conversion of the methyl ester to the amide was omitted. Following purification, the compound was tested as described above with the results shown.

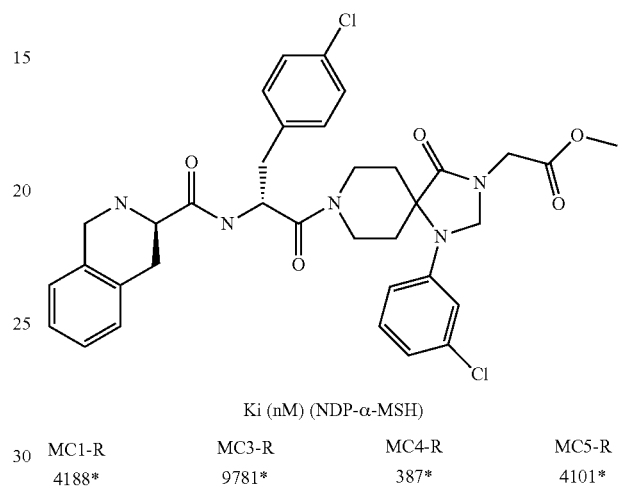

Ki (nM) (NDP-α-MSH)

| MC1-R | MC3-R | MC4-R | MC5-R |
|---|---|---|---|
| 4188* | 9781* | 387* | 4101* |

Example 110

(1-(4-Chloro-phenyl)-8-{(R)-3-(4-chloro-phenyl)-2-[((R)-1,2,3,4-tetrahydro-isoquinoline-3-carbonyl)-amino]-propionyl}-4-oxo-1,3,8-triaza-spiro[4.5]dec-3-yl)-acetic acid methyl ester The following compound was synthesized according to the methods in Schemes 5 and 3, except that the conversion of the methyl ester to the amide was omitted. Following purification, the compound was tested as described above with the results shown.

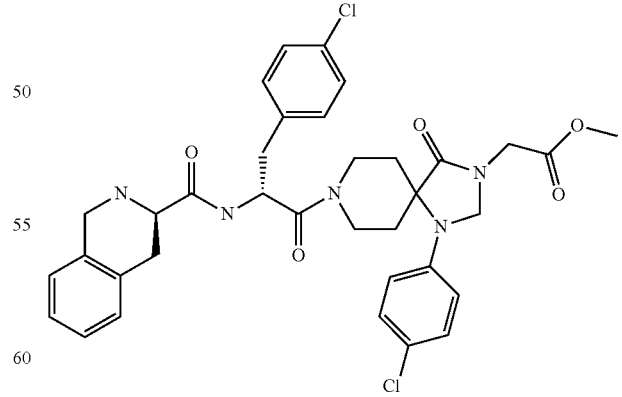

Ki (nM) (NDP-α-MSH)

| MC1-R | MC3-R | MC4-R | MC5-R |
|---|---|---|---|
| 8578* | 8106* | 540* | 5299* |

Example 111

(R)-1,2,3,4-Tetrahydro-isoquinoline-3-carboxylic acid [(R)-1-(4-chloro-benzyl)-2-(3-ethyl-4-oxo-1-phenyl-1,3,8-triaza-spiro[4.5]dec-8-yl)-2-oxo-ethyl]-amide The following compound was synthesized by the method of Scheme 1 described above, in which iodoethane was used instead of methyl bromoacetate, and as a final step the Boc protecting group was removed with trifluoroacetic acid. Following purification, the compound was tested as described above with the results shown.

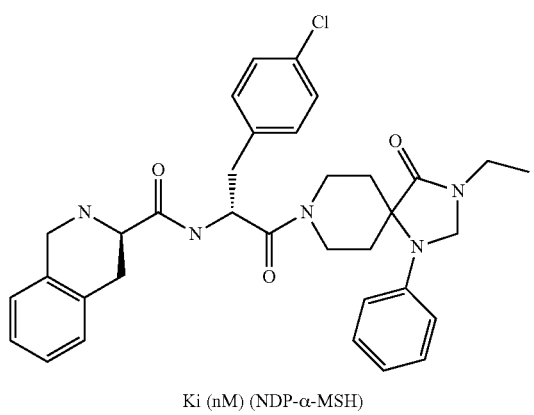

Ki (nM) (NDP-α-MSH)

| MC1-R | MC3-R | MC4-R | MC5-R |
|---|---|---|---|
| 6105* | 9762* | 221* | 6359* |

Example 112

(R)-1,2,3,4-Tetrahydro-isoquinoline-3-carboxylic acid [(R)-1-(4-chloro-benzyl)-2-(3-isopropyl-4-oxo-1-phenyl-1,3,8-triaza-spiro[4.5]dec-8-yl)-2-oxo-ethyl]-amide The following compound was synthesized by the method of Scheme 1 described above, in which 2-iodopropane was used instead of methyl bromoacetate, and the alkylation reaction was done in tetrahydrofuran at 60° C. with a catalytic amount of 15-crown-5. As a final step the Boc protecting group was removed with trifluoroacetic acid. Following purification, the compound was tested as described above with the results shown.

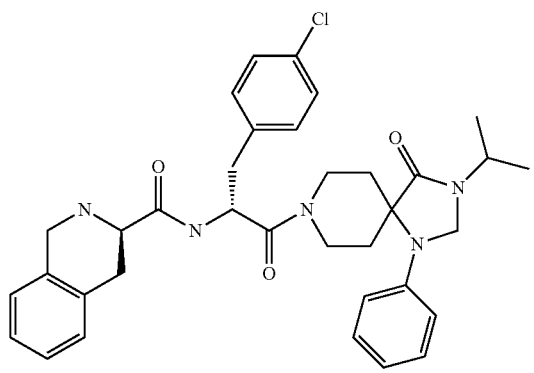

Ki (nM) (NDP-α-MSH)

| MC1-R | MC3-R | MC4-R | MC5-R |
|---|---|---|---|
| 1840* | 7523* | 65* | 1631* |

Example 113

(S)-2-Amino-N-[(R)-2-[3-(benzylcarbamoyl-methyl)-4-oxo-1-phenyl-1,3,8-triaza-spiro[4.5]dec-8-yl]-1-(4-methoxy-benzyl)-2-oxo-ethyl]-3-(3-methyl-3H-imidazol-4-yl)-propionamide The following compound was synthesized by the methods in Scheme 1 and Scheme 3 using Fmoc-D-Tyr(OMe) and Boc-His(Me). Following purification, the compound was tested as described above with the results shown.

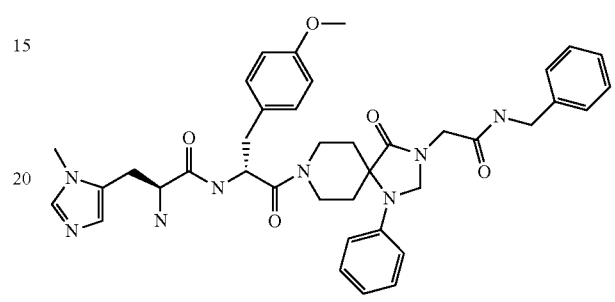

Inhibition at 1 μM (NDP-α-MSH)

| MC1-R | MC3-R | MC4-R | MC5-R |
|---|---|---|---|
| 55%* | 10%* | 59%* | 8%* |

Ki (nM) (NDP-α-MSH)

| MC1-R | MC3-R | MC4-R | MC5-R |
|---|---|---|---|
| 368* | >10000* | 447* | 2909* |

Example 114

{8-[(R)-2-[(S)-2-Amino-3-(3-methyl-3H-imidazol-4-yl)-propionylamino]-3-(4-methoxy-phenyl)-propionyl]-4-oxo-1-phenyl-1,3,8-triaza-spiro[4.5]dec-3-yl}-acetic acid methyl ester The following compound was synthesized by the methods in Scheme 1 using Fmoc-D-Tyr(OMe) and Boc-His(Me). Following purification, the compound was tested as described above with the results shown.

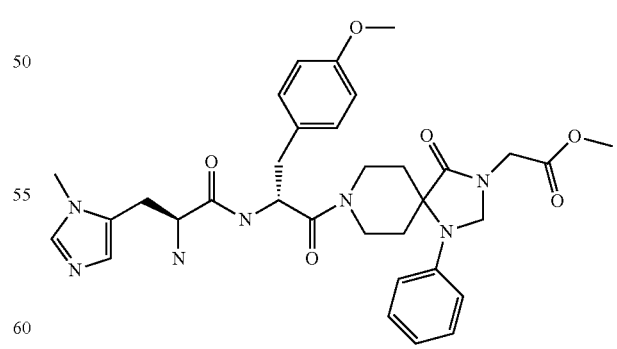

Ki (nM) (NDP-α-MSH)

| MC1-R | MC3-R | MC4-R | MC5-R |
|---|---|---|---|
| 964* | >10000* | 4082* | >10000* |

Example 115

(S)-2-Amino-N-[(R)-2-[3-(2-diethylamino-ethyl)-4-oxo-1-phenyl-1,3,8-triaza-spiro[4.5]dec-8-yl]-1-(4-methoxy-benzyl)-2-oxo-ethyl]-3-(3-methyl-3H-imidazol-4-yl)-propionamide The following compound was synthesized by the methods in Scheme 1 and Scheme 2 using Fmoc-D-Tyr(OMe) and Boc-His(Me). Following purification, the compound was tested as described above with the results shown.

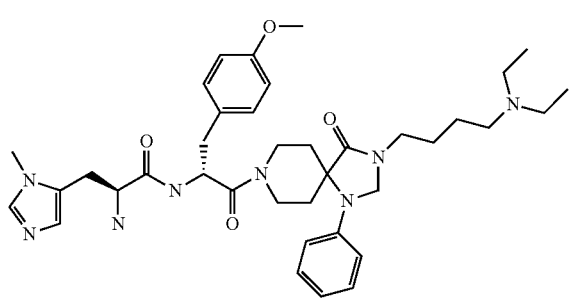

Ki (nM) (NDP-α-MSH)

| MC1-R | MC3-R | MC4-R | MC5-R |
|---|---|---|---|
| 1611 | >10000 | 7787 | >10000 |

Example 116

(S)-2-Amino-N-[(R)-2-[3-(2-diethylamino-ethyl)-2,4-dioxo-1-phenyl-1,3,8-triaza-spiro[4.5]dec-8-yl]-1-(4-methoxy-benzyl)-2-oxo-ethyl]-3-(3-methyl-3H-imidazol-4-yl)-propionamide The following compound was synthesized by the methods in Scheme 7 using Fmoc-D-Tyr(OMe) and Boc-His(Me). Chloroethyldiethylamine hydrochloride was used in place of methyl bromoacetate. Following purification, the compound was tested as described above with the results shown.

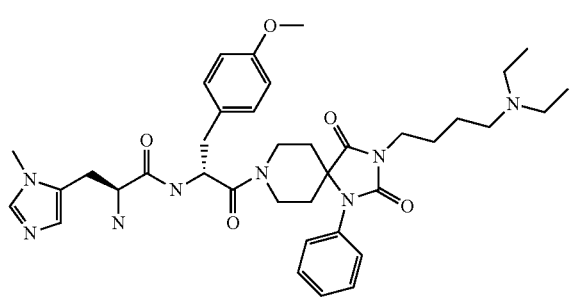

Inhibition at 1 μM (NDP-α-MSH)

| MC1-R | MC3-R | MC4-R | MC5-R |
|---|---|---|---|
| 4%* | 30%* | 4%* | 19%* |

Example 117

(S)-2-Amino-N-[(R)-1-(4-methoxy-benzyl)-2-(3-methylcarbamoylmethyl-4-oxo-1-phenyl-1,3,8-triaza-spiro[4.5]dec-8-yl)-2-oxo-ethyl]-3-(3-methyl-3H-imidazol-4-yl)-propionamide The following compound was synthesized by the methods in Scheme 1 and Scheme 3 using Fmoc-D-Tyr(OMe) and Boc-His(Me). Following purification, the compound was tested as described above with the results shown.

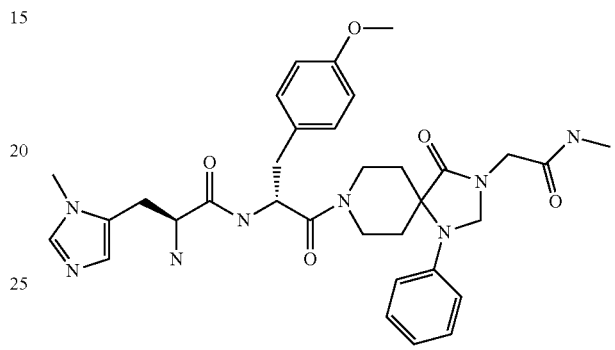

Inhibition at 1 μM (NDP-α-MSH)

| MC1-R | MC3-R | MC4-R | MC5-R |
|---|---|---|---|
| 14%* | 26%* | 11%* | 25%* |

Example 118

(S)-2-Amino-N-[(R)-2-(3-dimethylcarbamoylmethyl-4-oxo-1-phenyl-1,3,8-triaza-spiro[4.5]dec-8-yl)-1-(4-methoxy-benzyl)-2-oxo-ethyl]-3-(3-methyl-3H-imidazol-4-yl)-propionamide The following compound was synthesized by the methods in Scheme 1 and Scheme 3 using Fmoc-D-Tyr(OMe) and Boc-His(Me). Following purification, the compound was tested as described above with the results shown.

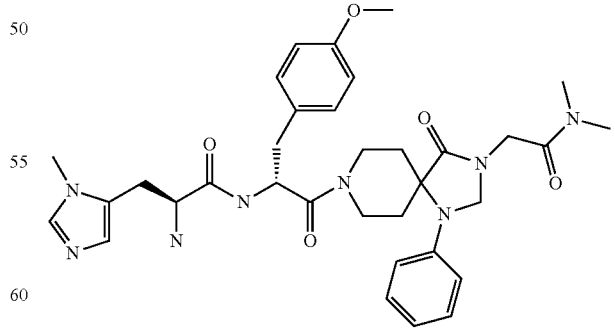

Inhibition at 1 μM (NDP-α-MSH)

| MC1-R | MC3-R | MC4-R | MC5-R |
|---|---|---|---|
| 22%* | 29%* | 12%* | 24%* |

Example 119

(S)-2-Amino-N-[(R)-2-(3-ethylcarbamoylmethyl-4-oxo-1-phenyl-1,3,8-triaza-spiro[4.5]dec-8-yl)-1-(4-methoxy-benzyl)-2-oxo-ethyl]-3-(3-methyl-3H-imidazol-4-yl)-propionamide The following compound was synthesized by the methods in Scheme 1 and Scheme 3 using Fmoc-D-Tyr(OMe) and Boc-His(Me). Following purification, the compound was tested as described above with the results shown.

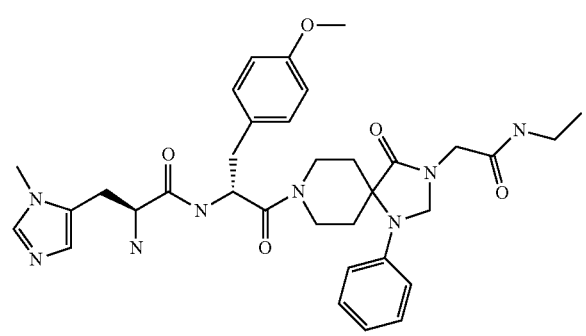

Inhibition at 1 μM (NDP-α-MSH)

| MC1-R | MC3-R | MC4-R | MC5-R |
|---|---|---|---|
| 28%* | 29%* | 17%* | 22%* |

Example 120

8-[(R)-2-Amino-3-(4-methoxy-phenyl)-propionyl]-3-(2-diethylamino-ethyl)-1-phenyl-1,3,8-triaza-spiro[4.5]decan-4-one The following compound was synthesized by the methods in Scheme 1 and Scheme 2 using Fmoc-D-Tyr(OMe). The second amino acid coupling was omitted after the Fmoc protecting group was removed. Following purification, the compound was tested as described above with the results shown.

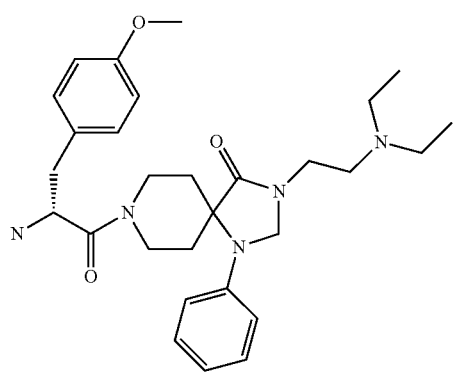

Inhibition at 1 μM (NDP-α-MSH)

| MC1-R | MC3-R | MC4-R | MC5-R |
|---|---|---|---|
| 2%* | 22%* | 2%* | 24%* |

Example 121

Piperidine-4-carboxylic acid [(R)-2-[3-(2-diethylamino-ethyl)-4-oxo-1-phenyl-1,3,8-triaza-spiro[4.5]dec-8-yl]-1-(4-methoxy-benzyl)-2-oxo-ethyl]-amide The following compound was synthesized by the methods in Scheme 1 and Scheme 2 using Fmoc-D-Tyr(OMe) and Boc-piperidine carboxylic acid. Following purification, the compound was tested as described above with the results shown.

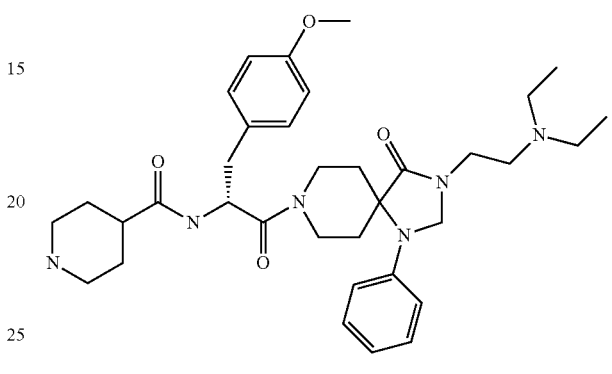

Inhibition at 1 μM (NDP-α-MSH)

| MC1-R | MC3-R | MC4-R | MC5-R |
|---|---|---|---|
| 7%* | 30%* | 14%* | 38%* |

Example 122

[(R)-2-[3-(2-Diethylamino-ethyl)-4-oxo-1-phenyl-1,3,8-triaza-spiro[4.5]dec-8-yl]-1-(4-methyoxy-benzyl)-2-oxo-ethyl]-carbamic acid tert-butyl ester The following compound was synthesized by the methods in Scheme 1 and Scheme 2 using Boc-D-Tyr(OMe). The Boc protecting group was not removed and the compound was purified by chromatography on silica gel.

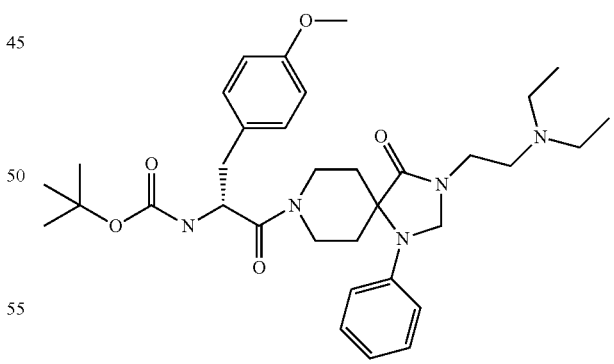

Example 123

4-Amino-N-[(R)-2-[3-(2-diethylamino-ethyl)-4-oxo-1-phenyl-1,3,8-triaza-spiro[4.5]dec-8-yl]-1-(4-methoxy-benzyl)-2-oxo-ethyl]-butyramide The following compound was synthesized by the methods in Scheme 1 and Scheme 2 using Fmoc-D-Tyr(OMe) and

Example 124

5-Amino-pentanoic acid [(R)-2-[3-(2-diethylamino-ethyl)-4-oxo-1-phenyl-1,3,8-triaza-spiro[4.5]dec-8-yl]-1-(4-methoxy-benzyl)-2-oxo-ethyl]-amide The following compound was synthesized by the methods in Scheme 1 and Scheme 2 using Fmoc-D-Tyr(OMe) and 5-Boc-aminopentanoic acid. Following purification, the compound was tested as described above with the results shown.

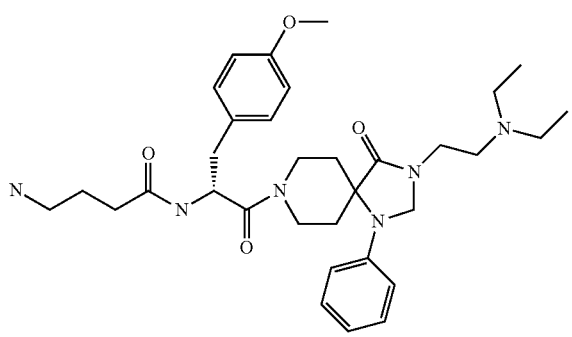

Inhibition at 1 μM (NDP-α-MSH)

| MC1-R | MC3-R | MC4-R | MC5-R |
|---|---|---|---|
| 1%* | 0%* | 16%* | 0%* |

Example 125

(R)-1,2,3,4-Tetrahydro-isoquinoline-3-carboxylic acid [(R)-2-[3-(2-diethylamino-ethyl)-4-oxo-1-phenyl-1,3,8-triaza-spiro[4.5]dec-8-yl]-1-(4-methoxy-benzyl)-2-oxo-ethyl]-amide The following compound was synthesized by the methods in Scheme 1 and Scheme 2 using Fmoc-D-Tyr(OMe) and Boc-D-Tic-OH. Following purification, the compound was tested as described above with the results shown.

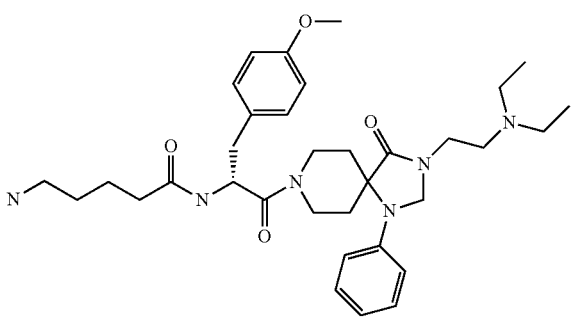

Inhibition at 1 μM (NDP-α-MSH)

| MC1-R | MC3-R | MC4-R | MC5-R |
|---|---|---|---|
| 0%* | 6%* | 0%* | 19%* |

Example 126

N-[(R)-2-[3-(2-Diethylamino-ethyl)-4-oxo-1-phenyl-1,3,8-triaza-spiro[4.5]dec-8-yl]-1-(4-methoxy-benzyl)-2-oxo-ethyl]-3-(1H-imidazol-4-yl)-propionamide The following compound was synthesized by the methods in Scheme 1 and Scheme 2 using Fmoc-D-Tyr(OMe) and 3-(1-Boc-imidazol-4-yl)propionic acid. Following purification, the compound was tested as described above with the results shown.

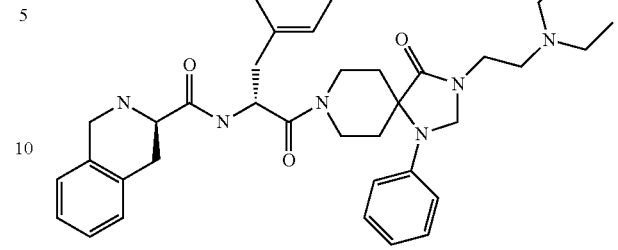

Inhibition at 1 μM (NDP-α-MSH)

| MC1-R | MC3-R | MC4-R | MC5-R |
|---|---|---|---|
| 0%* | 2%* | 47%* | 22%* |

Ki(nM) (NDP-α-MSH)

| MC1-R | MC3-R | MC4-R | MC5-R |
|---|---|---|---|
| 3835* | N/A | 1852* | N/A |

Example 127

(R)-1,2,3,4-Tetrahydro-isoquinoline-3-carboxylic acid ((R)-1-(4-chloro-benzyl)-2-{3-[(2-methoxy-benzylcarbamoyl)-methyl]-2,4-dioxo-1-phenyl-1,3,8-triaza-spiro[4.5]dec-8-yl}-2-oxo-ethyl)-amide The following compound was synthesized by the method in Scheme 7 using 2-methoxybenzylamine. Following purification, the compound was tested as described above with the results shown.

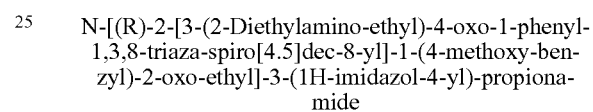
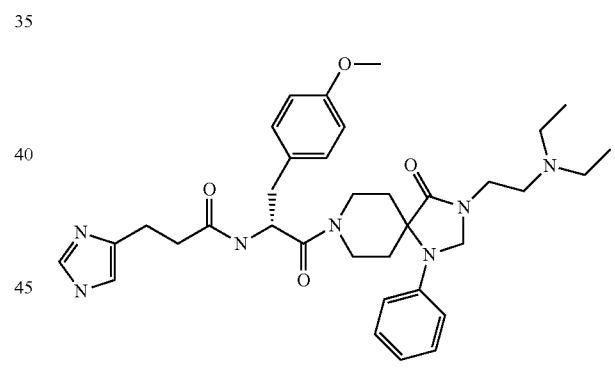

Inhibition at 1 μM (NDP-α-MSH)

| MC1-R | MC3-R | MC4-R | MC5-R |
|---|---|---|---|
| 47%* | 4%* | 13%* | 3%* |

Ki(nM) (NDP-α-MSH)

| MC1-R | MC3-R | MC4-R | MC5-R |
|---|---|---|---|
| 410* | N/A | >10000* | N/A |

123

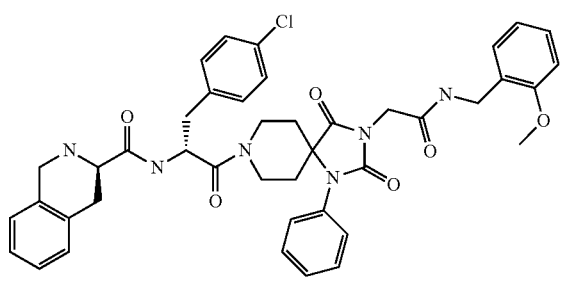

Inhibition at 1 µM (NDP-α-MSH)

| MC1-R | MC3-R | MC4-R | MC5-R |
|---|---|---|---|
| 10%* | 13%* | 70%* | N/A |

Ki(nM) (NDP-α-MSH)

| MC1-R | MC3-R | MC4-R | MC5-R |
|---|---|---|---|
| N/A | N/A | 396* | N/A |

Example 128

(R)-1,2,3,4-Tetrahydro-isoquinoline-3-carboxylic acid ((R)-1-(4-chloro-benzyl)-2-{3-[(3-methoxy-benzylcarbamoyl)-methyl]-2,4-dioxo-1-phenyl-1,3,8-triaza-spiro[4.5]dec-8-yl}-2-oxo-ethyl)-amide The following compound was synthesized by the method in Scheme 7 using 3-methoxybenzylamine. Following purification, the compound was tested as described above with the results shown.

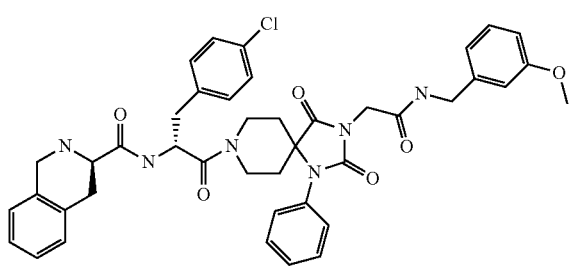

Inhibition at 1 µM (NDP-α-MSH)

| MC1-R | MC3-R | MC4-R | MC5-R |
|---|---|---|---|
| 1%* | 7%* | 79%* | N/A |

Ki(nM) (NDP-α-MSH)

| MC1-R | MC3-R | MC4-R | MC5-R |
|---|---|---|---|
| N/A | N/A | 160* | N/A |

Example 129

(R)-1,2,3,4-Tetrahydro-isoquinoline-3-carboxylic acid ((R)-1-(4-chloro-benzyl)-2-{3-[(4-methoxy-benzylcarbamoyl)-methyl]-2,4-dioxo-1-phenyl-1,3,8-triaza-spiro[4.5]dec-8-yl}-2-oxo-ethyl)-amide The following compound was synthesized by the method in Scheme 7 using 4-methoxybenzylamine. Following purification, the compound was tested as described above with the results shown.

124

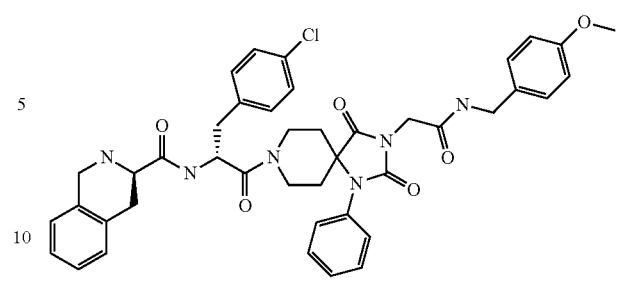

Inhibition at 1 µM (NDP-α-MSH)

| MC1-R | MC3-R | MC4-R | MC5-R |
|---|---|---|---|
| 0%* | 4%* | 76%* | N/A |

Ki(nM) (NDP-α-MSH)

| MC1-R | MC3-R | MC4-R | MC5-R |
|---|---|---|---|
| N/A | N/A | 200* | N/A |

Example 130

(R)-1,2,3,4-Tetrahydro-isoquinoline-3-carboxylic acid [(R)-1-(4-chloro-benzyl)-2-(3-diethylcarbamoylmethyl-2,4-dioxo-1-phenyl-1,3,8-triaza-spiro[4.5]dec-8-yl)-2-oxo-ethyl]-amide The following compound was synthesized by the method in Scheme 7 using diethylamine. Following purification, the compound was tested as described above with the results shown.

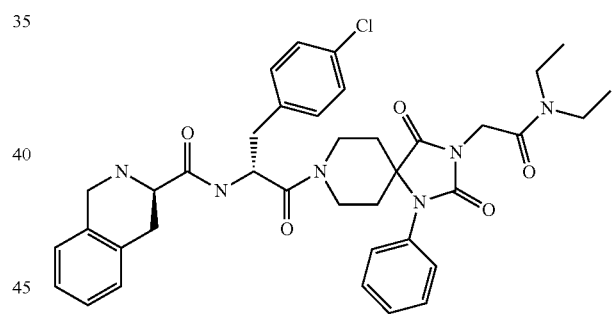

Inhibition at 1 µM (NDP-α-MSH)

| MC1-R | MC3-R | MC4-R | MC5-R |
|---|---|---|---|
| 5%* | 2%* | 25%* | N/A |

Ki(nM) (NDP-α-MSH)

| MC1-R | MC3-R | MC4-R | MC5-R |
|---|---|---|---|
| N/A | N/A | 2317* | N/A |

Example 131

(R)-1,2,3,4-Tetrahydro-isoquinoline-3-carboxylic acid {(R)-1-benzyl-2-[3-(2-diethylamino-ethyl)-4-oxo-1-phenyl-1,3,8-triaza-spiro[4.5]dec-8-yl]-2-oxo-ethyl}-amide The following compound was synthesized by the methods in Scheme 1 and Scheme 2 using Fmoc-D-Phe and diethylamine. Following purification, the compound was tested as described above with the results shown.

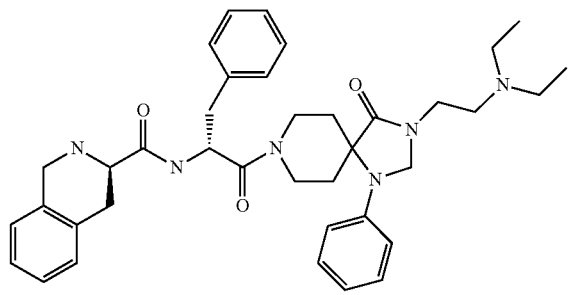

Inhibition at 1 µM (NDP-α-MSH)

| MC1-R | MC3-R | MC4-R | MC5-R |
|-------|-------|-------|-------|
| 7%*   | 22%*  | 19%*  | N/A   |

Example 132

Piperidine-4-carboxylic acid {(R)-1-benzyl-2-[3-(2-diethylamino-ethyl)-4-oxo-1-phenyl-1,3,8-triaza-spiro[4.5]dec-8-yl]-2-oxo-ethyl}-amide The following compound was synthesized by the methods in Scheme 1 and Scheme 2 using Fmoc-D-Phe and Boc-piperidine carboxylic acid. Following purification, the compound was tested as described above with the results shown.

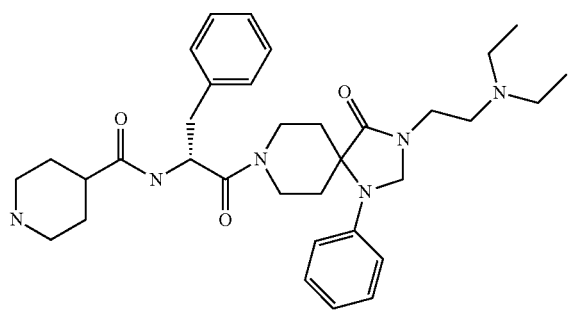

Inhibition at 1 µM (NDP-α-MSH)

| MC1-R | MC3-R | MC4-R | MC5-R |
|-------|-------|-------|-------|
| 3%*   | 17%*  | 4%*   | N/A   |

Example 133

(S)-2-Amino-N-{(R)-1-benzyl-2-[3-(2-diethylamino-ethyl)-4-oxo-1-phenyl-1,3,8-triaza-spiro[4.5]dec-8-yl]-2-oxo-ethyl}-3-(3-methyl-3H-imidazol-4-yl)-propionamide The following compound was synthesized by the methods in Scheme 1 and Scheme 2 using Fmoc-D-Phe and Boc-His(Me). Following purification, the compound was tested as described above with the results shown.

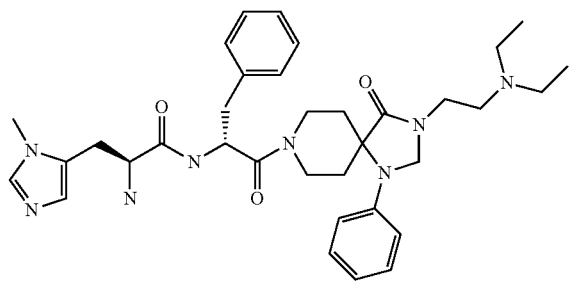

Inhibition at 1 µM (NDP-α-MSH)

| MC1-R | MC3-R | MC4-R | MC5-R |
|-------|-------|-------|-------|
| 12%*  | 0%*   | 14%*  | 0%*   |

Example 134

N-{(R)-1-Benzyl-2-[3-(2-diethylamino-ethyl)-4-oxo-1-phenyl-1,3,8-triaza-spiro[4.5]dec-8-yl]-2-oxo-ethyl}-3-(1H-imidazol-4-yl)-propionamide The following compound was synthesized by the methods in Scheme 1 and Scheme 2 using Fmoc-D-Phe and 3-(1-Boc-imidazol-4-yl)propionic acid. Following purification, the compound was tested as described above with the results shown.

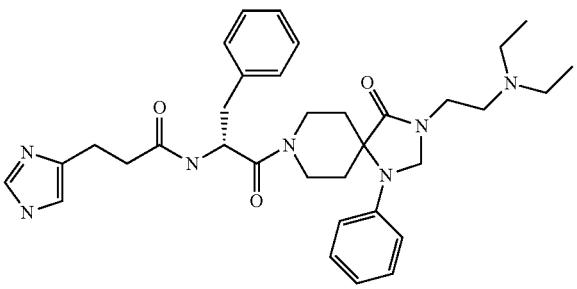

Inhibition at 1 µM (NDP-α-MSH)

| MC1-R | MC3-R | MC4-R | MC5-R |
|-------|-------|-------|-------|
| 2%*   | 8%*   | 4%*   | 0%*   |

Example 135

(S)-2-Amino-N-{(R)-1-benzyl-2-[3-(2-diethylamino-ethyl)-4-oxo-1-phenyl-1,3,8-triaza-spiro[4.5]dec-8-yl]-2-oxo-ethyl}-3-(1H-imidazol-4-yl)-propionamide The following compound was synthesized by the methods in Scheme 1 and Scheme 2 using Fmoc-D-Tyr(OMe) and Boc-His. Following purification, the compound was tested as described above with the results shown.

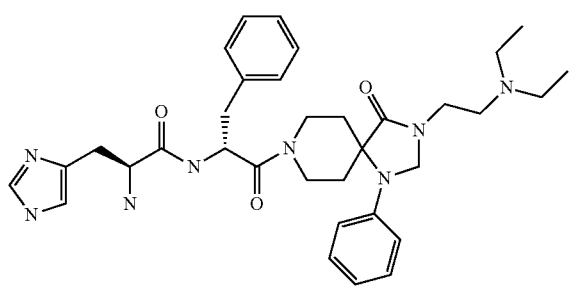

Inhibition at 1 µM (NDP-α-MSH)

| MC1-R | MC3-R | MC4-R | MC5-R |
|---|---|---|---|
| 17%* | 0%* | 0%* | N/A |

Example 136

4-Amino-N-{(R)-1-benzyl-2-[3-(2-diethylamino-ethyl)-4-oxo-1-phenyl-1,3,8-triaza-spiro[4.5]dec-8-yl]-2-oxo-ethyl}-butyramide The following compound was synthesized by the methods in Scheme 1 and Scheme 2 using Fmoc-D-Phe and 4-Boc-aminobutyric acid. Following purification, the compound was tested as described above with the results shown.

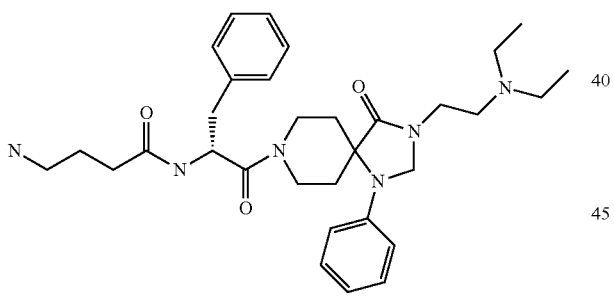

Example 137

{8-[(R)-2-(3-3H-Imidazol-4-yl-propionylamino)-3-(4-methoxy-phenyl)-propionyl]-4-oxo-1-phenyl-1,3,8-triaza-spiro[4.5]dec-3-yl}-acetic acid methyl ester The following compound was synthesized by the method in Scheme 1 using Fmoc-D-Tyr(OMe) and 3-(1-Boc-imidazol-4-yl)propionic acid, and as a final step the Boc protecting group was removed with trifluoroacetic acid. Following purification, the compound was tested as described above with the results shown.

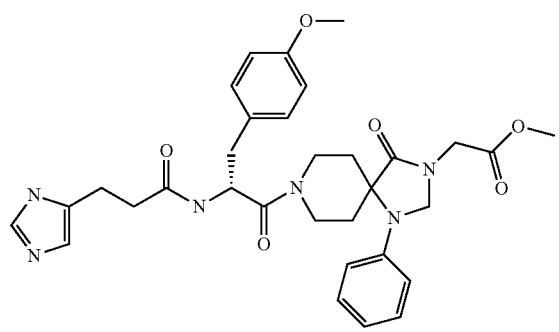

Inhibition at 1 µM (NDP-α-MSH)

| MC1-R | MC3-R | MC4-R | MC5-R |
|---|---|---|---|
| 53%* | 2%* | 23%* | N/A |

Ki(nM) (NDP-α-MSH)

| MC1-R | MC3-R | MC4-R | MC5-R |
|---|---|---|---|
| 299* | N/A | N/A | N/A |

In functional assays, the compound was a partial agonist at MC1-R, with an average $EC_{50}$ of 38 nM and an $E_{max}$ of 56%.

Example 138

{8-[(R)-2-(5-Amino-pentanoylamino)-3-(4-methoxy-phenyl)-propionyl]-4-oxo-1-phenyl-1,3,8-triaza-spiro[4.5]dec-3-yl}-acetic acid methyl ester The following compound was synthesized by the method in Scheme 1 using Fmoc-D-Tyr(OMe) and 5-Boc-aminopentanoic acid, and as a final step the Boc protecting group was removed with trifluoroacetic acid. Following purification, the compound was tested as described above with the results shown.

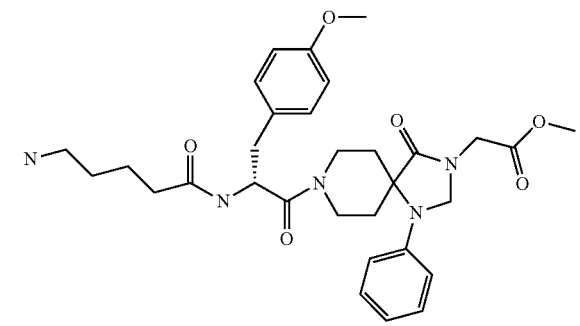

Ki(nM) (NDP-α-MSH)

| MC1-R | MC3-R | MC4-R | MC5-R |
|---|---|---|---|
| 950 | N/A | N/A | N/A |

In functional assays, the compound was a partial agonist at MC1-R, with an average $EC_{50}$ of 340 nM and an $E_{max}$ of 44%.

Example 139

(S)-2-Amino-N-[(R)-1-(4-methoxy-benzyl)-2-(3-methyl-4-oxo-1-phenyl-1,3,8-triaza-spiro[4.5]dec-8-yl)-2-oxo-ethyl]-3-(3-methyl-3H-imidazol-4-yl)-propionamide The compound of Example 139 was synthesized by the method of Scheme 1 described above, in which iodomethane was used instead of methyl bromoacetate, Fmoc-D-Tyr(OMe) and Boc-His(Me) were used in the amino acid coupling steps, and as a final step the Boc protecting group was removed with trifluoroacetic acid. Following purification, the compound was tested as described above with the results shown.

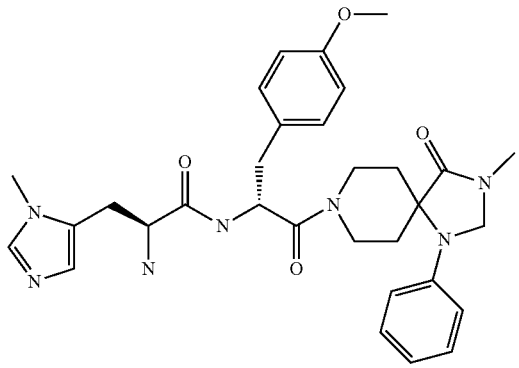

Inhibition at 1 µM (NDP-α-MSH)

| MC1-R | MC3-R | MC4-R | MC5-R |
|---|---|---|---|
| 51%* | N/A | 32%* | N/A |

Ki(nM) (NDP-α-MSH)

| MC1-R | MC3-R | MC4-R | MC5-R |
|---|---|---|---|
| 450 | N/A | N/A | N/A |

In functional assays, the compound was a partial agonist at MC1-R, with an average $EC_{50}$ of 177 nM and an $E_{max}$ of 45%.

Example 140

(S)-2-Amino-N-[(R)-2-(3-ethyl-4-oxo-1-phenyl-1,3, 8-triaza-spiro[4.5]dec-8-yl)-1-(4-methoxy-benzyl)-2-oxo-ethyl]-3-(3-methyl-3H-imidazol-4-yl)-propionamide The following compound was synthesized using the procedures described for the synthesis of Example 139 except that iodoethane was used instead of iodomethane. Following purification, the compound was tested as described above with the results shown.

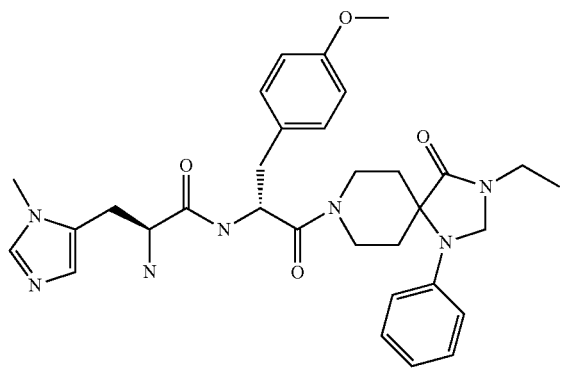

Inhibition at 1 µM (NDP-α-MSH)

| MC1-R | MC3-R | MC4-R | MC5-R |
|---|---|---|---|
| 67%* | N/A | 39%* | N/A |

Ki (nM) (NDP-α-MSH)

| MC1-R | MC3-R | MC4-R | MC5-R |
|---|---|---|---|
| 150 | N/A | N/A | N/A |

In functional assays, the compound was a partial agonist at MC1-R, with an average $EC_{50}$ of 25 nM and an $E_{max}$ of 42%.

Example 141

(S)-2-Amino-N-[(R)-2-(3-isopropyl-4-oxo-1-phenyl-1,3,8-triaza-spiro[4.5]dec-8-yl)-1-(4-methoxy-benzyl)-2-oxo-ethyl]-3-(3-methyl-3H-imidazol-4-yl)-propionamide The following compound was synthesized using the procedures described for the synthesis of Example 139 except that 2-iodopropane was used instead of iodomethane and the alkylation reaction was heated at 55° C. in the presence of a catalytic amount of 15-crown-5. Following purification, the compound was tested as described above with the results shown.

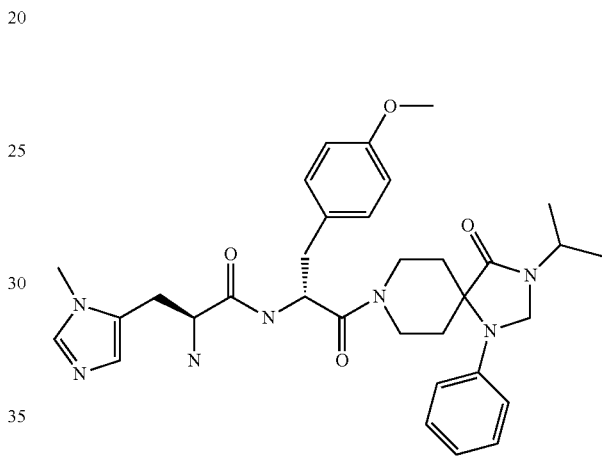

Inhibition at 1 µM (NDP-α-MSH)

| MC1-R | MC3-R | MC4-R | MC5-R |
|---|---|---|---|
| 87%* | N/A | 62%* | N/A |

Ki(nM) (NDP-α-MSH)

| MC1-R | MC3-R | MC4-R | MC5-R |
|---|---|---|---|
| 65 | N/A | N/A | N/A |

In functional assays, the compound was a partial agonist at MC1-R, with an average $EC_{50}$ of 6 nM and an $E_{max}$ of 45%.

Example 142

(S)-2-Amino-N-[(R)-2-(3-butyl-4-oxo-1-phenyl-1,3, 8-triaza-spiro[4.5]dec-8-yl)-1-(4-methoxy-benzyl)-2-oxo-ethyl]-3-(3-methyl-3H-imidazol-4-yl)-propionamide The following compound was synthesized using the procedures described for the synthesis of Example 139 except that 1-iodobutane was used instead of iodomethane. Following purification, the compound was tested as described above with the results shown.

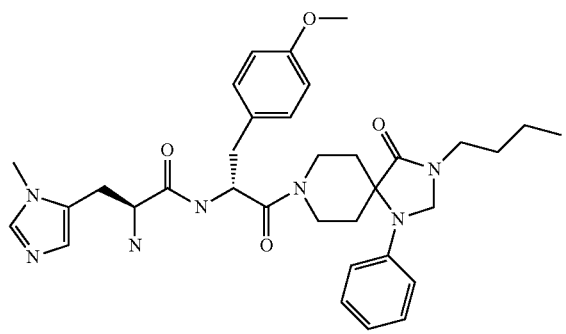

Inhibition at 1 µM (NDP-α-MSH)

| MC1-R | MC3-R | MC4-R | MC5-R |
|---|---|---|---|
| 74%* | N/A | 46%* | N/A |

Ki (nM) (NDP-α-MSH)

| MC1-R | MC3-R | MC4-R | MC5-R |
|---|---|---|---|
| 110 | N/A | N/A | N/A |

In functional assays, the compound was a partial agonist at MC1-R, with an average $EC_{50}$ of 20 nM and an $E_{max}$ of 43%.

Example 143

(S)-2-Amino-N-[(R)-1-(4-methoxy-benzyl)-2-oxo-2-(4-oxo-1-phenyl-1,3,8-triaza-spiro[4.5]dec-8-yl)-ethyl]-3-(3-methyl-3H-imidazol-4-yl)-propionamide The following compound was synthesized using the procedures described for the synthesis of Example 139 except that the alkylation step was omitted. Following purification, the compound was tested as described above with the results shown.

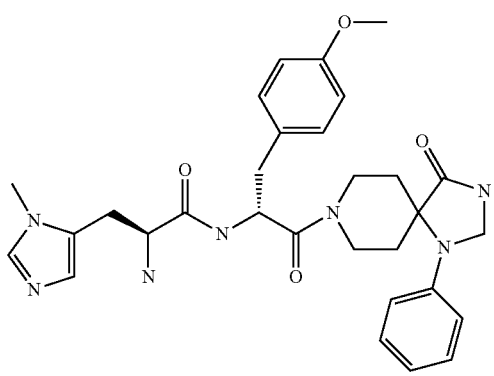

Inhibition at 1 µM (NDP-α-MSH)

| MC1-R | MC3-R | MC4-R | MC5-R |
|---|---|---|---|
| 30%* | N/A | 27%* | N/A |

Example 144

(S)-2-Amino-N-[(R)-2-(3-benzyl-4-oxo-1-phenyl-1,3,8-triaza-spiro[4.5]dec-8-yl)-1-(4-methoxy-benzyl)-2-oxo-ethyl]-3-(3-methyl-3H-imidazol-4-yl)-propionamide The following compound was synthesized using the procedures described for the synthesis of Example 139 except that benzyl bromide was used instead of iodomethane. Following purification, the compound was tested as described above with the results shown.

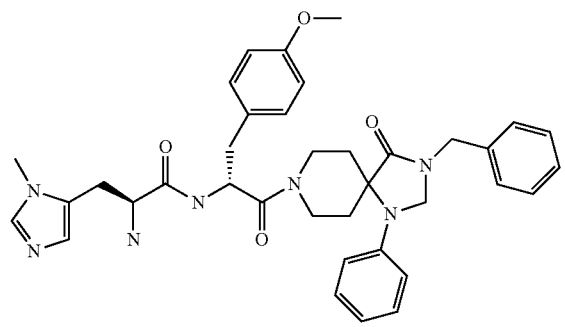

Inhibition at 1 µM (NDP-α-MSH)

| MC1-R | MC3-R | MC4-R | MC5-R |
|---|---|---|---|
| 63%* | 0% | 12%* | N/A |

Ki (nM) (NDP-α-MSH)

| MC1-R | MC3-R | MC4-R | MC5-R |
|---|---|---|---|
| 130 | N/A | N/A | N/A |

In functional assays, the compound was a partial agonist at MC1-R, with an average $EC_{50}$ of 17 nM and an $E_{max}$ of 46%.

Example 145

8-(2-Amino-acetyl)-3-pyridin-2-ylmethyl-1-pyridin-3-ylmethyl-1,3,8-triaza-spiro[4,5]decane-2,4-dione The following compound was synthesized using the method in Scheme 8. Following purification, the compound was tested as described above with the results shown.

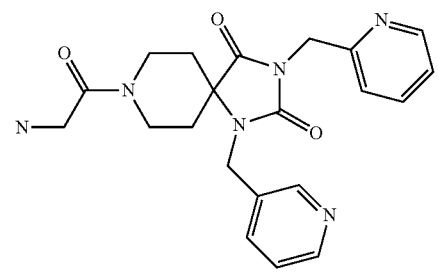

Inhibition at 1 µM (NDP-α-MSH)

| MC1-R | MC3-R | MC4-R | MC5-R |
|---|---|---|---|
| 19% | 35% | 20% | 9% |

Example 146

3-Pyridin-2-ylmethyl-1-pyridin-3-ylmethyl-1,3,8-triaza-spiro[4.5]decane-2,4-dione The following compound was synthesized using the method in Scheme 8 except that the final amino acid coupling step was omitted. Following purification, the compound was tested as described above with the results shown.

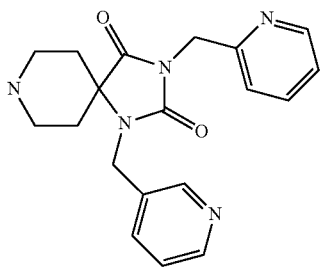

Inhibition at 1 µM (NDP-α-MSH)

| MC1-R | MC3-R | MC4-R | MC5-R |
|---|---|---|---|
| 12% | 0% | 7% | 5% |

Example 147

(S)-2-Amino-N-[(R)-2-[3-(2-amino-ethyl)-4-oxo-1-phenyl-1,3,8-triaza-spiro[4.5]dec-8-yl]-1-(4-methoxy-benzyl)-2-oxo-ethyl]-3-(3-methyl-3H-imidazol-4-yl)-propionamide The compound of Example 147 was synthesized by the methods of Scheme 1 and Scheme 2 described above, in which a 7 M solution of ammonia in methanol was used. Fmoc-D-Tyr(OMe) and Boc-His(Me) were used in the amino acid coupling steps.

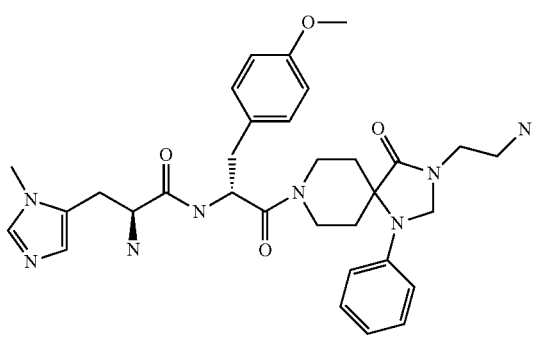

Example 148

(S)-2-Amino-N-[(R)-2-[3-(2-hydroxy-ethyl)-4-oxo-1-phenyl-1,3,8-triaza-spiro[4.5]dec-8-yl]-1-(4-methoxy-benzyl)-2-oxo-ethyl]-3-(3-methyl-3H-imidazol-4-yl)-propionamide The compound of Example 148 was made by the methods of Scheme 1 and Scheme 2 described above except that the conversion of the alcohol to the amine was omitted. Fmoc-D-Tyr(OMe) and Boc-His(Me) were used in the amino acid coupling steps. Following purification, the compound was tested as described above with the results shown.

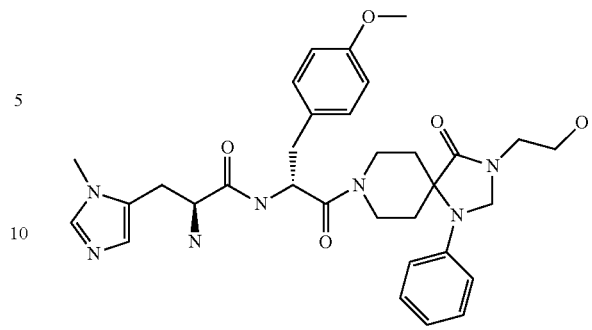

Inhibition at 1 µM (NDP-α-MSH)

| MC1-R | MC3-R | MC4-R | MC5-R |
|---|---|---|---|
| 17% | 0% | 0% | 0% |

Example 149

N-[(R)-2-[3-(2-Hydroxy-ethyl)-4-oxo-1-phenyl-1,3,8-triaza-spiro[4.5]dec-8-yl]-1-(4-methoxy-benzyl)-2-oxo-ethyl]-3-(3H-imidazol-4-yl)-propionamide The compound of Example 149 was synthesized by the methods of Scheme 1 and Scheme 2 described above except that the conversion of the alcohol to the amine was omitted. Fmoc-D-Tyr(OMe) and 3-(1-Boc-imidazol-4-yl)propionic acid were used in the amino acid coupling steps. Following purification, the compound was tested as described above with the results shown.

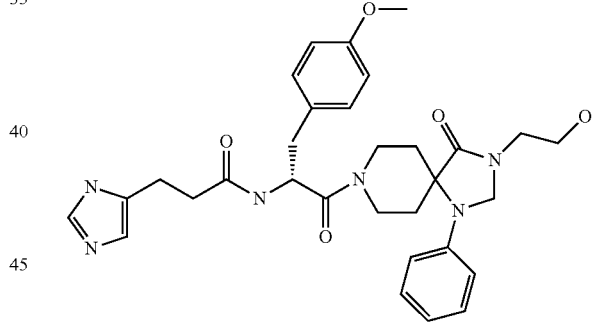

Inhibition at 1 µM (NDP-α-MSH)

| MC1-R | MC3-R | MC4-R | MC5-R |
|---|---|---|---|
| 53%* | 0%* | 0%* | 0%* |

Ki (nM) (NDP-α-MSH)

| MC1-R | MC3-R | MC4-R | MC5-R |
|---|---|---|---|
| 130 | N/A | N/A | N/A |

In functional assays, the compound was a partial agonist at MC1-R, with an average $EC_{50}$ of 25 nM and an $E_{max}$ of 60%.

Example 150

3-(3H-Imidazol-4-yl)-N-[(R)-2-(3-isopropyl-4-oxo-1-phenyl-1,3,8-triaza-spiro[4.5]dec-8-yl)-1(4-methoxy-benzyl)-2-oxo-ethyl]-propionamide The following compound was synthesized using the methods used to synthesize Example 141. 3-(1-Boc-imidazol-4- yl)propionic acid was used in the final acid coupling step. Following purification, the compound was tested as described above with the results shown.

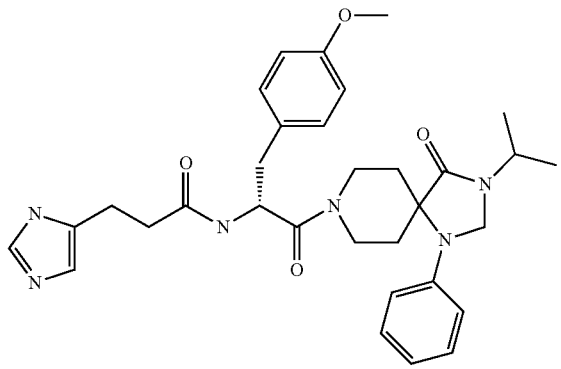

Inhibition at 1 µM (NDP-α-MSH)

| MC1-R | MC3-R | MC4-R | MC5-R |
|---|---|---|---|
| 90%* | 0%* | 10%* | 0%* |

Ki (nM) (NDP-α-MSH)

| MC1-R | MC3-R | MC4-R | MC5-R |
|---|---|---|---|
| 20 | N/A | N/A | N/A |

In functional assays, the compound was a partial agonist at MC1-R, with an average EC$_{50}$ of 3 nM and an E$_{max}$ of 71%.

Example 151

(S)-2-Amino-N-[(R)-2-(3-cyclopentyl-4-oxo-1-phenyl-1,3,8-triaza-spiro[4.5]dec-8-yl)-1-(4-methoxy-benzyl)-2-oxo-ethyl]-3-(3-methyl-3H-imidazol-4-yl)-propionamide The following compound was synthesized using the methods used to synthesize Example 141. Cyclopentyl iodide was used in the alkylation step. Following purification, the compound was tested as described above with the results shown.

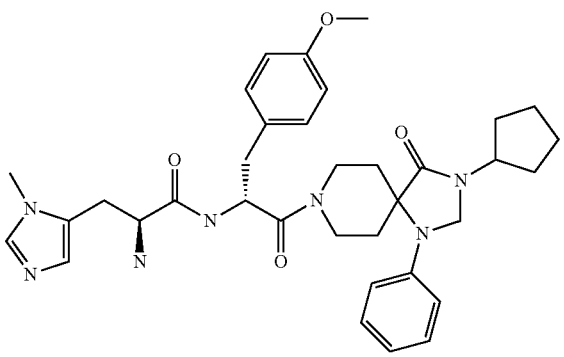

Inhibition at 1 µM (NDP-α-MSH)

| MC1-R | MC3-R | MC4-R | MC5-R |
|---|---|---|---|
| 74%* | 0% | 36%* | N/A |

Ki (nM) (NDP-α-MSH)

| MC1-R | MC3-R | MC4-R | MC5-R |
|---|---|---|---|
| 25 | N/A | N/A | N/A |

In functional assays, the compound was a partial agonist at MC1-R, with an average EC$_{50}$ of 7 nM and an E$_{max}$ of 37%.

Example 152

N-[(R)-2-(3-Cyclopentyl-4-oxo-1-phenyl-1,3,8-triaza-spiro[4.5]dec-8-yl)-1-(4-methoxy-benzyl)-2-oxo-ethyl]-3-(3H-imidazol-4-yl)-propionamide The following compound was synthesized using the methods used to synthesize Example 151. 3-(1-Boc-imidazol-4-yl)propionic acid was used in the final acid coupling step. Following purification, the compound was tested as described above with the results shown.

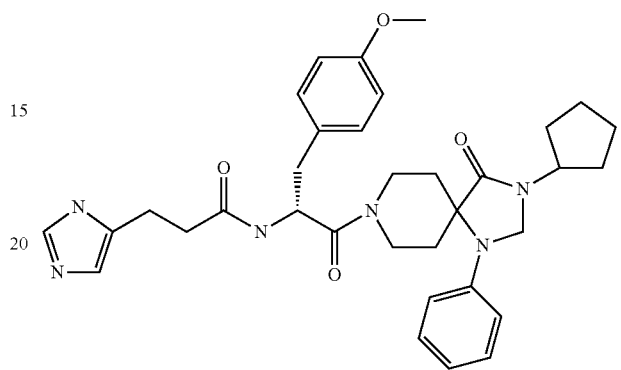

Inhibition at 1 µM (NDP-α-MSH)

| MC1-R | MC3-R | MC4-R | MC5-R |
|---|---|---|---|
| 93%* | 1% | 45%* | N/A |

Ki (nM) (NDP-α-MSH)

| MC1-R | MC3-R | MC4-R | MC5-R |
|---|---|---|---|
| 9 | N/A | >10000 | N/A |

In functional assays, the compound was a partial agonist at MC1-R, with an average EC$_{50}$ of 2 nM and an E$_{max}$ of 50%.

Example 153

N-[(R)-2-(3-Benzyl-4-oxo-1-phenyl-1,3,8-triaza-spiro[4.5]dec-8-yl)-1-(4-methoxy-benzyl)-2-oxo-ethyl]-3-(1H-imidazol-4-yl)-propionamide The following compound was synthesized using the methods used to synthesize Example 144. 3-(1-Boc-imidazol-4-yl)propionic acid was used in the final acid coupling step. Following purification, the compound was tested as described above with the results shown.

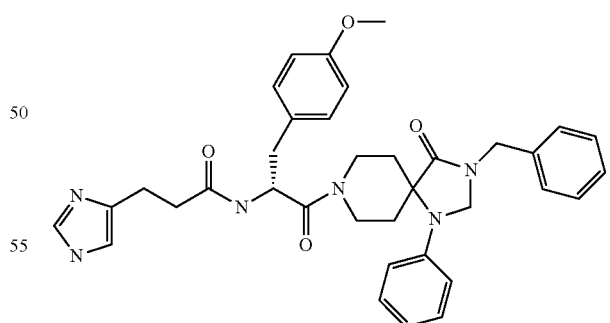

Inhibition at 1 µM (NDP-α-MSH)

| MC1-R | MC3-R | MC4-R | MC5-R |
|---|---|---|---|
| 70%* | 1% | 20%* | N/A |

Ki (nM) (NDP-α-MSH)

| MC1-R | MC3-R | MC4-R | MC5-R |
|---|---|---|---|
| 35 | N/A | N/A | N/A |

In functional assays, the compound was a partial agonist at MC1-R, with an average EC$_{50}$ of 12 nM and an E$_{max}$ of 54%.

Example 154

N-[(R)-2-[3-(2-Chloro-benzyl)-4-oxo-1-phenyl-1,3,
8-triaza-spiro[4.5]dec-8-yl]-1-(4-methoxy-benzyl)-2-
oxo-ethyl]-3-(1H-imidazol-4-yl)-propionamide The following compound was synthesized using the methods used to make Example 153. 2-chlorobenzyl bromide was used in the alkylation step. Following purification, the compound was tested as described above with the results shown.

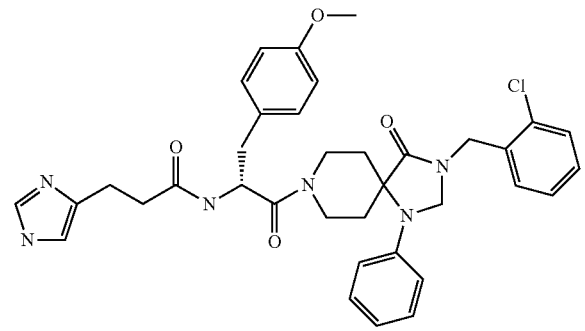

Inhibition at 1 μM (NDP-α-MSH)

| MC1-R | MC3-R | MC4-R | MC5-R |
|---|---|---|---|
| 68%* | 6% | 27%* | N/A |

Ki (nM) (NDP-α-MSH)

| MC1-R | MC3-R | MC4-R | MC5-R |
|---|---|---|---|
| 35 | N/A | N/A | N/A |

In functional assays, the compound was a partial agonist at MC1-R, with an average $EC_{50}$ of 26 nM and an $E_{max}$ of 50%.

Example 155

N-[(R)-2-[3-(3-Chloro-benzyl)-4-oxo-1-phenyl-1,3,
8-triaza-spiro[4.5]dec-8-yl]-1-(4-methoxy-benzyl)-2-
oxo-ethyl]-3-(1H-imidazol-4-yl)-propionamide The following compound was synthesized using the methods used to make Example 153. 3-chlorobenzyl bromide was used in the alkylation step. Following purification, the compound was tested as described above with the results shown.

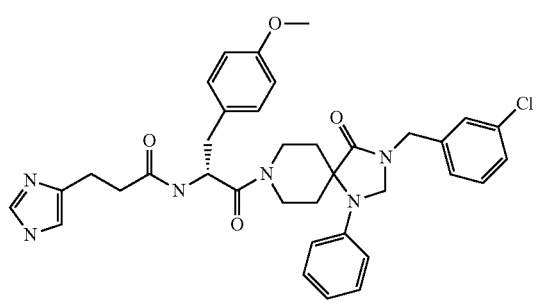

Inhibition at 1 μM (NDP-α-MSH)

| MC1-R | MC3-R | MC4-R | MC5-R |
|---|---|---|---|
| 59%* | 2% | 0%* | N/A |

Ki (nM) (NDP-α-MSH)

| MC1-R | MC3-R | MC4-R | MC5-R |
|---|---|---|---|
| 55 | N/A | N/A | N/A |

In functional assays, the compound was a partial agonist at MC1-R, with an average $EC_{50}$ of 14 nM and an $E_{max}$ of 42%.

Example 156

N-[(R)-2-[3-(4-Chloro-benzyl)-4-oxo-1-phenyl-1,3,
8-triaza-spiro[4.5]dec-8-yl]-1-(4-methoxy-benzyl)-2-
oxo-ethyl]-3-(1H-imidazol-4-yl)-propionamide The following compound was synthesized using the methods used to make Example 153. 4-chlorobenzyl bromide was used in the alkylation step. Following purification, the compound was tested as described above with the results shown.

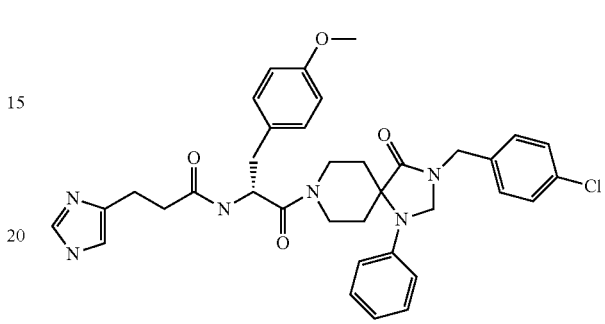

Inhibition at 1 μM (NDP-α-MSH)

| MC1-R | MC3-R | MC4-R | MC5-R |
|---|---|---|---|
| 57%* | 0% | 3%* | N/A |

Ki (nM) (NDP-α-MSH)

| MC1-R | MC3-R | MC4-R | MC5-R |
|---|---|---|---|
| 55 | N/A | N/A | N/A |

In functional assays, the compound was a partial agonist at MC1-R, with an average $EC_{50}$ of 23 nM and an $E_{max}$ of 45%.

Example 157

3-(1H-Imidazol-4-yl)-N-[(R)-1-(4-methoxy-benzyl)-
2-oxo-2-(4-oxo-1-phenyl-3-pyridin-2-ylmethyl-1,3,
8-triaza-spiro[4.5]dec-8-yl)-ethyl]-propionamide The following compound was synthesized using the methods used to make Example 153. 2-bromomethylpyridine hydrobromide was used in the alkylation step. Following purification, the compound was tested as described above with the results shown.

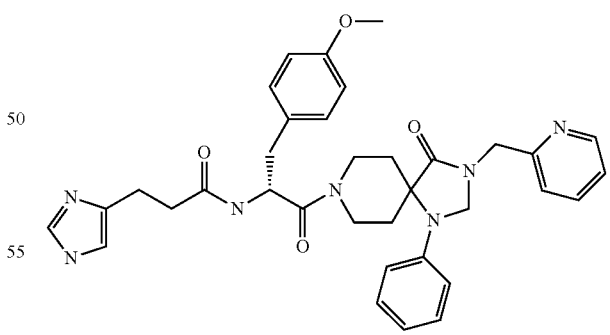

Inhibition at 1 μM (NDP-α-MSH)

| MC1-R | MC3-R | MC4-R | MC5-R |
|---|---|---|---|
| 65%* | 0% | 15%* | N/A |

Ki (nM) (NDP-α-MSH)

| MC1-R | MC3-R | MC4-R | MC5-R |
|---|---|---|---|
| 130 | N/A | N/A | N/A |

In functional assays, the compound was a partial agonist at MC1-R, with an average $EC_{50}$ of 41 nM and an $E_{max}$ of 38%.

Example 158

3-(1H-Imidazol-4-yl)-N-[(R)-1-(4-methoxy-benzyl)-2-oxo-2-(4-oxo-1-phenyl-3-pyridin-3-ylmethyl-1,3,8-triaza-spiro[4.5]dec-8-yl)-ethyl]-propionamide The following compound was synthesized using the methods used to make Example 153. 3-bromopyridine hydrobromide was used in the alkylation step. Following purification, the compound was tested as described above with the results shown.

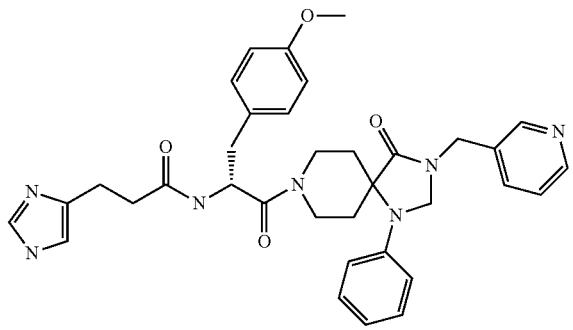

Inhibition at 1 μM (NDP-α-MSH)

| MC1-R | MC3-R | MC4-R | MC5-R |
|---|---|---|---|
| 76%* | 0% | 33%* | N/A |

Ki (nM) (NDP-α-MSH)

| MC1-R | MC3-R | MC4-R | MC5-R |
|---|---|---|---|
| 75 | N/A | N/A | N/A |

In functional assays, the compound was a partial agonist at MC1-R, with an average $EC_{50}$ of 20 nM and an $E_{max}$ of 45%.

Example 159

N-[(R)-2-(3-Cyclobutyl-4-oxo-1-phenyl-1,3,8-triaza-spiro[4.5]dec-8-yl)-1-(4-methoxy-benzyl)-2-oxo-ethyl]-3-(3H-imidazol-4-yl)-propionamide The following compound was synthesized using the methods used to make Example 152. Bromocyclobutane was used in the alkylation step. Following purification, the compound was tested as described above with the results shown.

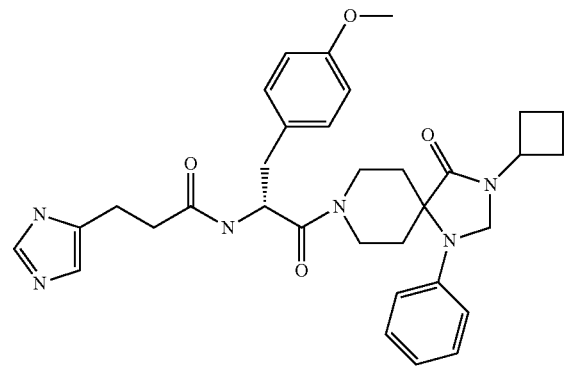

Inhibition at 1 μM (NDP-α-MSH)

| MC1-R | MC3-R | MC4-R | MC5-R |
|---|---|---|---|
| 90%* | 1% | 13%* | N/A |

Ki (nM) (NDP-α-MSH)

| MC1-R | MC3-R | MC4-R | MC5-R |
|---|---|---|---|
| 20 | N/A | N/A | N/A |

In functional assays, the compound was a partial agonist at MC1-R, with an average $EC_{50}$ of 6 nM and an $E_{max}$ of 49%.

Example 160

1H-Indole-3-carboxylic acid [(R)-2-(3-isopropyl-4-oxo-1-phenyl-1,3,8-triaza-spiro[4.5]dec-8-yl)-1-(4-methoxy-benzyl)-2-oxo-ethyl]-amide The following compound was synthesized using the methods used to make Example 139 except that 2-iodopropane was used instead of iodomethane and the alkylation reaction was heated at 55° C. in the presence of a catalytic amount of 15-crown-5. Indole-3-carboxylic acid was used in the final acylation step. Following purification, the compound was tested as described above with the results shown.

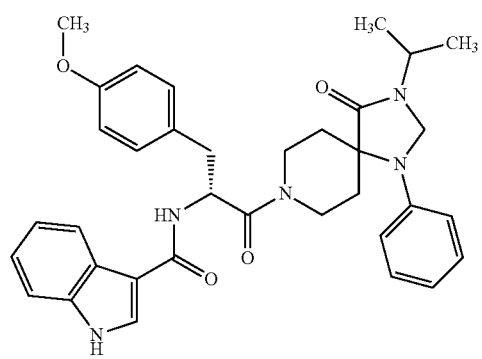

Inhibition at 1 μM (NPD-α-MSH)

| MC1-R | MC3-R | MC4-R | MC5-R |
|---|---|---|---|
| 15% | 0% | N/A | N/A |

Ki( nM) (NDP-α-MSH)

| MC1-R | MC3-R | MC4-R | MC5-R |
|---|---|---|---|
| 1550 | N/A | 95 | N/A |

Example 161

N-[(R)-2-(3-Isopropyl-4-oxo-1-phenyl-1,3,8-triaza-spiro[4.5]dec-8-yl)-1-(4-methoxy-benzyl)-2-oxo-ethyl]-2-(S)-1,2,3,4-tetrahydro-isoquinolin-3-yl-acetamide The following compound was synthesized using the methods used to make Example 139 except that 2-iodopropane was used instead of iodomethane and the alkylation reaction was heated at 55° C. in the presence of a catalytic amount of 15-crown-5. N-Boc-2-(S)-1,2,3,4-tetrahydroisoquinolineacetic acid was used in the final acylation step, and as a final step the Boc protecting group was removed with trifluoroacetic acid. Following purification, the compound was tested as described above with the results shown.

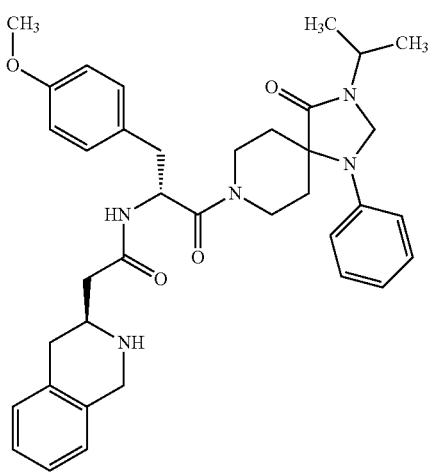

Inhibition at 1 µM (NPD-α-MSH)

| MC1-R | MC3-R | MC4-R | MC5-R |
|---|---|---|---|
| 61% | 0% | N/A | N/A |

Ki( nM) (NDP-α-MSH)

| MC1-R | MC3-R | MC4-R | MC5-R |
|---|---|---|---|
| 210 | N/A | 78 | N/A |

Example 162

1H-Indole-2-carboxylic acid [(R)-2-(3-isopropyl-4-oxo-1-phenyl-1,3,8-triaza-spiro[4.5]dec-8-yl)-1-(4-methoxy-benzyl)-2-oxo-ethyl]-amide The following compound was synthesized using the methods used to make Example 139 except that 2-iodopropane was used instead of iodomethane and the alkylation reaction was heated at 55° C. in the presence of a catalytic amount of 15-crown-5. Indole-2-carboxylic acid was used in the final acylation step. Following purification, the compound was tested as described above with the results shown.

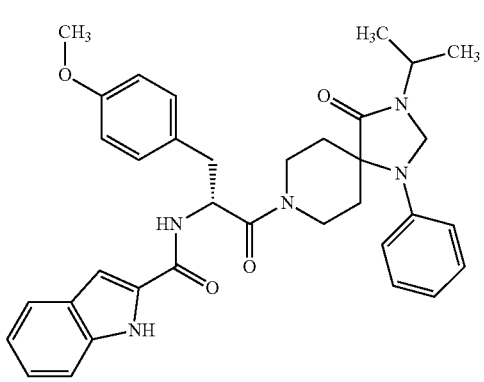

Inhibition at 1 µM (NPD-α-MSH)

| MC1-R | MC3-R | MC4-R | MC5-R |
|---|---|---|---|
| 23% | 6% | N/A | N/A |

Ki( nM) (NDP-α-MSH)

| MC1-R | MC3-R | MC4-R | MC5-R |
|---|---|---|---|
| >10000 | N/A | 30 | N/A |

Example 163

Quinoline-3-carboxylic acid [(R)-2-(3-isopropyl-4-oxo-1-phenyl-1,3,8-triaza-spiro[4.5]dec-8-yl)-1-(4-methoxy-benzyl)-2-oxo-ethyl]-amide The following compound was synthesized using the methods used to make Example 139 except that 2-iodopropane was used instead of iodomethane and the alkylation reaction was heated at 55° C. in the presence of a catalytic amount of 15-crown-5. 3-Quinolinecarboxylic acid was used in the final acylation step. Following purification, the compound was tested as described above with the results shown.

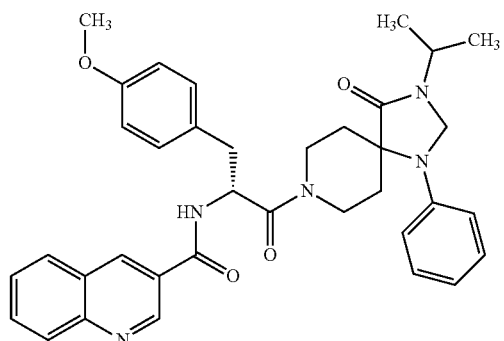

Inhibition at 1 µM (NPD-α-MSH)

| MC1-R | MC3-R | MC4-R | MC5-R |
|---|---|---|---|
| 45% | 0% | N/A | N/A |

Ki( nM) (NDP-α-MSH)

| MC1-R | MC3-R | MC4-R | MC5-R |
|---|---|---|---|
| 450 |  | 33 |  |

Example 164

N-[(R)-2-(3-Isopropyl-4-oxo-1-phenyl-1,3,8-triaza-spiro[4.5]dec-8-yl)-1-(4-methoxy-benzyl)-2-oxo-ethyl]-2-(R)-1,2,3,4-tetrahydro-isoquinolin-3-yl-acetamide The following compound was synthesized using the methods used to make Example 139 except that 2-iodopropane was used instead of iodomethane and the alkylation reaction was heated at 55° C. in the presence of a catalytic amount of 15-crown-5. N-Boc-2-®-1,2,3,4-tetrahydroisoquinolineacetic acid was used in the final acylation step, and as a final step the Boc protecting group was removed with trifluoroacetic acid. Following purification, the compound was tested as described above with the results shown.

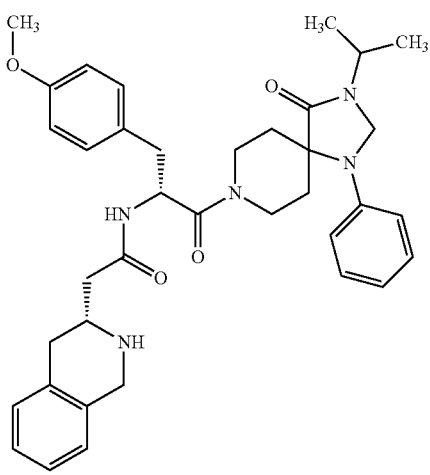

Inhibition at 1 µM (NDP-α-MSH)

| MC1-R | MC3-R | MC4-R | MC5-R |
|---|---|---|---|
| 91% | 0% | N/A | N/A |

Ki (nM) (NDP-α-MSH)

| MC1-R | MC3-R | MC4-R | MC5-R |
|---|---|---|---|
| 15 | N/A | 130 | N/A |

In functional assays, the compound was a partial agonist at MC1-R, with an average $EC_{50}$ of 0.7 nM and an $E_{max}$ of 75%.

Example 165

8-[4-(4-Chloro-phenyl)-1-(tetrahydro-pyran-4-yl)-pyrrolidine-3-carbonyl]-3-isopropyl-1-phenyl-1,3,8-triaza-spiro[4.5]decan-4-one The following compound was synthesized using the methods of Scheme 9. Bromocyclobutane was used in the alkylation step. Following purification, the compound was tested as described above with the results shown.

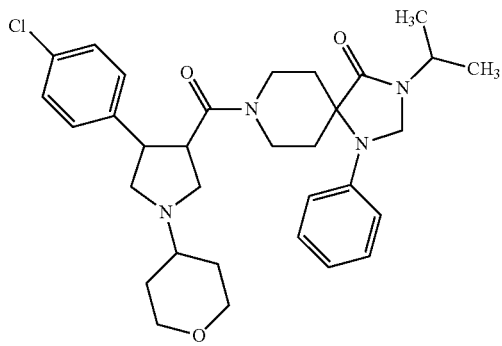

Inhibition at 1 µM (NPD-α-MSH)

| MC1-R | MC3-R | MC4-R | MC5-R |
|---|---|---|---|
| 20% | 9% | N/A | N/A |

Ki( nM) (NDP-α-MSH)

| MC1-R | MC3-R | MC4-R | MC5-R |
|---|---|---|---|
| N/A | N/A | 1450 | N/A |

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A compound of formula I:

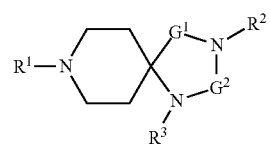

I or an enantiomer, stereoisomer or diastereoisomer thereof, or a pharmaceutically acceptable salt thereof, wherein:
$G^1$ and $G^2$ independently represent $CH_2$ or $C(O)$;
$R^1$ represents
H,
$R^x$,
$X^1$—$R^5$ or
$N(H)R^6$;
$R^5$ represents
$R^x$,
$OR^{7a}$,
$N(R^{7b})R^{7c}$ or
a structural fragment of the formula

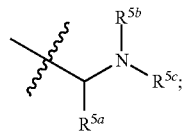

$R^{5b}$ and $R^{5c}$ independently represent H or $R^x$,
or $R^{5b}$ and $R^{5c}$, together with the N-atom to which they are attached, represent $Het^A$,
or $R^{5b}$ represents H or alkyl and $R^{5c}$ represents $X^2$—$R^8$;
$X^1$ and $X^2$ independently represent $C(O)$ or $S(O)_2$;
$R^8$ represents
$R^x$,
$OR^{7a}$,
$N(R^{7b})R^{7c}$ or
a structural fragment of the formula

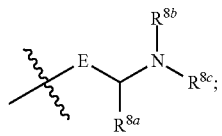

$R^{7a}$ represents $R^x$;
$R^{7b}$ and $R^{7c}$ independently represent H or $R^x$;
E represents a direct bond or phenylene;
$R^{5a}$ and $R^{8a}$ independently represent H or $R^x$;
$R^{8b}$ and $R^{8c}$ independently represent H or $R^x$,
or $R^{8b}$ and $R^{8c}$, together with the N-atom to which they are attached, represent $Het^B$;
$Het^A$ and $Het^B$ independently represent a 5- or 6-membered fully saturated, partly unsaturated or wholly aromatic heterocyclic group containing a N-atom (the atom to which either $R^{5b}$ and $R^{5c}$ or $R^{8b}$ and $R^{8c}$ are attached) and optionally containing one to three further heteroatoms selected from N, O and/or S, which heterocyclic group is optionally fused to a benzene ring and is optionally substituted by one or more substituents selected from $R^x$, halo, $OR^{9a}$, $S(O)_pR^{9b}$, CN, $N_3$, $NO_2$, =O, $B^3$—C(O)—$B^4$—$R^{9c}$, $N(R^{9d})R^{9e}$ and $N(OH)R^{9f}$;

$R^6$ represents C(O)—$X^3$—$R^x$;

$X^3$ represents O or NH;

$R^2$ represents $C_{2-4}$ alkyl optionally substituted by an OH, phenyl (which latter group is optionally substituted by one or two halo groups), pyridinyl, triazolyl, piperidinyl or morpholinyl group, $C_{5-6}$ cycloalkyl or a structural fragment of the formula

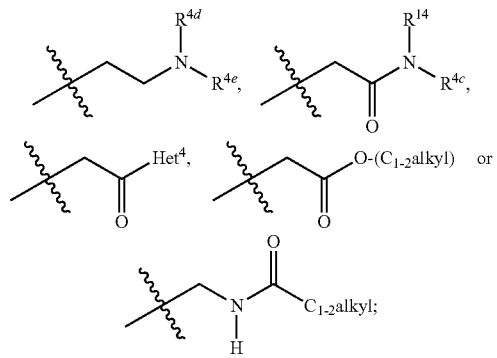

$R^3$ represents $R^x$;

$R^x$ represents, independently at each occurrence, alkyl, alkenyl, alkynyl, cycloalkyl (which latter four groups are optionally substituted by one or more substituents selected from alkyl, alkenyl, alkynyl, cycloalkyl, aryl, $Het^1$, halo, $OR^{4a}$, $S(O)_nR^{4b}$, CN, $N_3$, $NO_2$, =O, $B^1$—C(O)—$B^2$—$R^{4c}$, N(H)—C(=NH)—$NH_2$, $N(R^{4d})R^{4e}$ and $N(OH)R^{4f}$), aryl or $Het^2$;

$R^{4a}$ to $R^{4f}$ and $R^{9a}$ to $R^{9f}$ independently represent H, alkyl, alkenyl, alkynyl, cycloalkyl (which latter four groups are optionally substituted by one or more substituents selected from alkyl, alkenyl, alkynyl, cycloalkyl, aryl, $Het^3$, halo, OH, alkoxy, $NH_2$, N(H)alkyl and $N(alkyl)_2$), aryl or $Het^4$;

each aryl independently represents a $C_{6-14}$ carbocyclic aromatic group, which group may comprise one, two or three rings, at least one of which rings must be aromatic, and which aryl group is optionally substituted by one or more substituents selected from alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $Het^5$, halo, $OR^{10a}$, $S(O)_qR^{10b}$, CN, $N_3$, $NO_2$, =O, $B^5$—C(O)—$B^6$—$R^{10c}$, $N(R^{10d})R^{10e}$ and $N(OH)R^{10f}$), phenyl (which latter group is optionally substituted by one or more substituents selected from OH, halo, alkyl and alkoxy), $Het^6$, halo, $OR^{11a}$, $S(O)_rR^{11b}$, CN, $N_3$, $NO_2$, $B^7$—C(O)—$B^8$—$R^{11c}$, $N(R^{11d})R^{11e}$ and $N(OH)R^{11f}$;

$R^{10a}$ to $R^{10f}$ and $R^{11a}$ to $R^{11f}$ independently represent

H, alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), halo, OH, alkoxy, $NH_2$, N(H)alkyl and $N(alkyl)_2$), phenyl (which latter group is optionally substituted by one or more substituents selected from OH, halo, alkyl and alkoxy) or $Het^7$;

$Het^1$ to $Het^7$ independently represent 4- to 14-membered heterocyclic groups containing one or more heteroatoms selected from O, N and/or S, which heterocyclic groups may comprise one, two or three rings and may be substituted by one or more substituents selected from alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $Het^a$, halo, $OR^{12a}$, $S(O)_tR^{12b}$, CN, $N_3$, $NO_2$, =O, $B^9$—C(O)—$B^{10}$—$R^{12c}$, $N(R^{12d})R^{12e}$ and $N(OH)R^{12f}$)

phenyl (which latter group is optionally substituted by one or more substituents selected from OH, halo, alkyl and alkoxy), $Het^b$, halo, $OR^{13a}$, =O, $S(O)_uR^{13b}$, CN, $N_3$, $NO_2$, $B^{11}$—C(O)—$B^{12}$—$R^{13c}$, $N(R^{13d})R^{13e}$ and $N(OH)R^{13}$f;

$R^{12a}$ to $R^{12f}$ and $R^{13a}$ to $R^{13f}$ independently represent

H, alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), $Het^c$, halo, OH, alkoxy, $NH_2$, N(H)alkyl and $N(alkyl)_2$), phenyl (which latter group is optionally substituted by one or more substituents selected from OH, halo, alkyl and alkoxy) or $Het^d$;

$B^1$ to $B^{12}$ independently represent a direct bond, O, S or $N(R^{14})$;

n, p, q, r, t and u independently represent 0, 1 or 2;

$R^{14}$ represents H, alkyl, phenyl (which latter group is optionally substituted by one or more substituents selected from OH, halo, alkyl and alkoxy), cycloalkyl (which latter group is optionally substituted by one or more substituents selected from OH, =O, halo, alkyl and alkoxy) or $Het^e$;

$Het^a$ to $Het^e$ independently represent 5- or 6-membered heterocyclic groups containing one to four heteroatoms selected from O, N and/or S, which heterocyclic groups may be substituted by one or more substituents selected from halo, =O and alkyl; and unless otherwise specified alkyl, alkenyl, alkynyl and cycloalkyl groups, as well as the alkyl part of alkoxy groups, may be substituted by one or more halo atoms.

2. A compound as claimed in claim 1, wherein one of $G^1$ and $G^2$ represents $CH_2$ and the other of $G^1$ and $G^2$ represents C(O).

3. A compound as claimed in claim 1, wherein $R^1$ represents H, aryl or C(O)—$R^5$.

4. A compound as claimed in claim 1, wherein $R^5$ represents a structural fragment of the formula

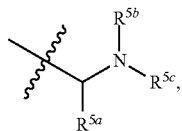

in which:
$R^{5a}$ represents
H,
alkyl, cycloalkyl (which latter two groups are optionally substituted by one or more substituents selected from alkyl, cycloalkyl, aryl, Het¹, halo, OR$^{4a}$, S(O)$_n$R$^{4b}$, B¹—C(O)—B²—R$^{4c}$, N(H)—C(=NH)—NH$_2$ and N(R$^{4d}$)R$^{4e}$),
aryl or
Het²;
$R^{5b}$ represents H or alkyl; and
$R^{5c}$ represents X²—R⁸.

5. A compound as claimed in claim 1, wherein X² represents C(O) or S(O)$_2$.

6. A compound as claimed in claim 1, wherein $R^8$ represents
H,
alkyl, cycloalkyl (which latter two groups are optionally substituted by one or more substituents selected from alkyl, cycloalkyl, aryl, Het¹, halo, OR$^{4a}$, S(O)$_n$R$^{4b}$, B¹—C(O)—B²—R$^{4c}$, N(H)—C(=NH)—NH$_2$ and N(R$^{4d}$)R$^{4e}$),
aryl,
Het²,
O-alkyl or
a structural fragment of the formula

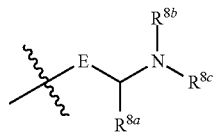

in which:
E represents a direct bond or 1,4-phenylene;
$R^{8a}$ represents
H,
alkyl, cycloalkyl (which latter two groups are optionally substituted by one or more substituents selected from alkyl, cycloalkyl, aryl, Het¹, halo, OR$^{4a}$, S(O)$_n$R$^{4b}$, B¹—C(O)—B²—R$^{4c}$, N(H)—C(=NH)—NH$_2$ and N(R$^{4d}$)R$^{4e}$),
aryl or
Het²; and
$R^{8b}$ and $R^{8c}$ independently represent
H,
alkyl, cycloalkyl (which latter two groups are optionally substituted by one or, more substituents selected from alkyl, cycloalkyl, aryl, Het¹, halo, OR$^{4a}$ and N(R$^{4d}$)R$^{4e}$)
aryl or
Het², or $R^{8b}$ and $R^{8c}$, together with the N-atom to which they are attached, represent a 5- or 6-membered fully saturated or wholly aromatic heterocyclic group containing a N-atom (the atom to which $R^{8b}$ and $R^{8c}$ are attached) and optionally containing one or two further heteroatoms selected from N, O and/or S, which heterocyclic group is optionally substituted by one or more substituents selected from alkyl and halo.

7. A compound as claimed in claim 1, wherein $R^3$ represents
alkyl optionally substituted by one cycloalkyl, aryl or Het¹ substituent,
cycloalkyl optionally substituted by one or two substituents selected from alkyl and halo,
aryl or
Het².

8. A compound as claimed in claim 1, wherein the compound is of formula Ia,

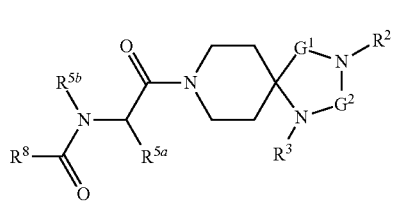

or an enantiomer, stereoisomer or diastereoisomer thereof, or a pharmaceutically acceptable salt thereof, wherein:
$R^{5a}$ represents
H,
$C_{1-4}$ alkyl,
methyl substituted by a phenyl (which latter group is optionally substituted by one or two substituents selected from trifluoromethyl, fluoro, chloro, methoxy and CN) or pyridinyl group or
phenyl optionally substituted by one or two substituents selected from trifluoromethyl, fluoro, chloro, methoxy and CN;
$R^{5b}$ represents H;
$R^8$ represents
$C_{1-4}$ alkyl optionally substituted by one or two substituents selected from piperidinyl, morpholinyl, piperazinyl, 4-methylpiperazinyl, imidazolyl, 1-methylimidazolyl, and N(R$^{4d}$)R$^{4e}$,
$C_{5-6}$ cycloalkyl,
pyrrolidinyl,
piperidinyl,
pyridinyl,
1,2,3,4-tetrahydroisoquinolinyl,
O—($C_{1-4}$ alkyl) or
a structural fragment of the formula

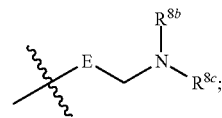

$R^{8b}$ represents H or methyl,
$R^{8c}$ represents
H,
$C_{1-4}$ alkyl,

C$_{1-2}$ alkyl substituted by a phenyl, OH, methoxy or NH$_2$ group or

C$_{5-6}$ cycloalkyl, or R$^{8b}$ and R$^{8c}$, together with the N-atom to which they are attached, represent a piperidin-1-yl, morpholin-1-yl, piperazin-1-yl, 4-methylpiperazin-1-yl or imidazol-1-yl group;

R$^{4c}$ represents

C$_{1-5}$ alkyl,

C$_{1-2}$ alkyl substituted by a phenyl (which latter group is optionally substituted by one or two substituents selected from C$_{1-2}$ alkyl and methoxy) or indolyl group, C$_{5-6}$ cycloalkyl or phenyl;

R$^{4d}$ represents, independently at each occurrence, H or C$_{1-2}$ alkyl;

R$^{4e}$ represents, independently at each occurrence,

H,

C$_{1-4}$ alkyl,

C$_{1-2}$ alkyl substituted by a phenyl (which latter group is optionally substituted by one or two halo groups), thienyl, OH or methoxy group or C$_{5-6}$ cycloalkyl;

R$^{14}$ represents H or methyl;

Het$^4$ represents piperazin-1-yl optionally substituted by C$_{1-2}$ alkyl;

R$^3$ represents methyl substituted by a phenyl or pyridinyl group,

C$_{5-6}$ cycloalkyl or phenyl optionally substituted by one or two chloro groups;

G$^2$ represents CH$_2$ or C(O).

9. A compound as claimed in claim 1, wherein the compound is of formula Ib,

Ib

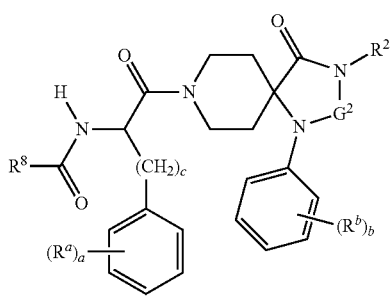

or an enantiomer, stereoisomer or diastereoisomer thereof, or a pharmaceutically acceptable salt thereof, wherein:

R$^a$ represents, independently at each occurrence, CN, trifluoromethyl, methoxy, fluoro or chloro;

R$^b$ represents, independently at each occurrence, fluoro or chloro;

a and b independently represent 0, 1 or 2;

c represents 0 or 1;

R$^8$ represents 1,2,3,4-tetrahydroisoquinolinyl or

C$_{2-4}$ alkyl terminally substituted by NH$_2$; and

G$^2$ represents CH$_2$ or C(O).

10. A compound as claimed in claim 1, wherein the compound is of formula Ic,

Ic

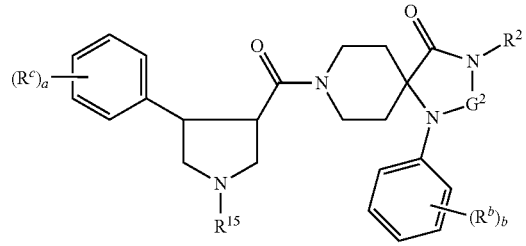

or an enantiomer, stereoisomer or diastereoisomer thereof, or a pharmaceutically acceptable salt thereof, wherein:

R$^b$ represents, independently at each occurrence, fluoro or chloro;

R$^c$ represents, independently at each occurrence, —OH, halo, alkyl or alkoxy;

a and b independently represent 0, 1 or 2;

R$^{15}$ represents alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), Het$^a$, halo, OR$^{12a}$, S(O)$_t$R$^{12b}$, CN, N$_3$, NO$_2$, =O, B$^9$—C(O)—B$^{10}$—R$^{12c}$, N(R$^{12d}$)R$^{12e}$ and N(OH)R$^{12f}$), phenyl (which latter group is optionally substituted by one or more substituents selected from OH, halo, alkyl and alkoxy), Het$^b$, halo, OR$^{13a}$, =O, S(O)$_u$R$^{13b}$, CN, N$_3$, NO$_2$, B$^{11}$—C(O)—B$^{12}$—R$^{13c}$, N(R$^{13d}$)R$^{13e}$ and N(OH)R$^{13f}$; and G$^2$ represents CH$_2$ or C(O).

11. A pharmaceutical composition comprising a compound as defined in claim 1 and a pharmaceutically acceptable carrier.

12. A compound of the formula:

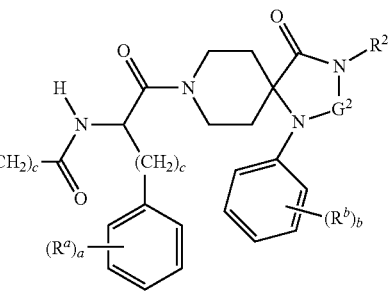

or an enantiomer, stereoisomer or diastereoisomer thereof, or a pharmaceutically acceptable salt thereof, wherein:

R$^a$ represents, independently at each occurrence, CN, trifluoromethyl, methoxy, fluoro or chloro;

R$^b$ represents, independently at each occurrence, fluoro or chloro;

a and b independently represent 0, 1 or 2;

c represents, independently at each occurrence, 0 or 1;

R$^2$ represents alkyl, alkenyl, alkynyl, cycloalkyl (which latter four groups are optionally substituted by one or more substituents selected from alkyl, alkenyl, alkynyl, cycloalkyl, aryl, Het$^1$, halo, OR$^{4a}$, S(O)$_n$R$^{4b}$, CN, N$_3$, NO$_2$, =O, B$^1$—C(O)—B$^2$—R$^{4c}$, N(H)—C(=NH)—NH$_2$, N(R$^{4d}$)R$^{4e}$ and N(OH)R$^{4f}$),
aryl or
Het$^2$;
R$^{4a}$ to R$^{4f}$ independently represent H, alkyl, alkenyl, alkynyl, cycloalkyl (which latter four groups are optionally substituted by one or more substituents selected from alkyl, alkenyl, alkynyl, cycloalkyl, aryl, Het$^3$, halo, OH, alkoxy, NH$_2$, N(H)alkyl and N(alkyl)$_2$), aryl or Het$^4$;
each aryl independently represents a C$_{6-14}$ carbocyclic aromatic group, which group may comprise one, two or three rings, at least one of which rings must be aromatic, and which aryl group is optionally substituted by one or more substituents selected from
  alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy) Het$^5$, halo, OR$^{10a}$, S(O)$_q$R$^{10b}$, CN, N$_3$, NO$_2$, =O, B$^5$—C(O)—B$^6$—R$^{10c}$, N(R$^{10d}$)R$^{10e}$ and N(OH)R$^{10f}$),
  phenyl (which latter group is optionally substituted by one or more substituents selected from OH, halo, alkyl and alkoxy),
  Het$^6$, halo, OR$^{11a}$, S(O)$_r$R$^{11b}$, CN, N$_3$, NO$_2$, B$^7$—C(O)—B$^8$—R$^{11c}$, N(R$^{11d}$)R$^{11e}$ and N(OH)R$^{11f}$;
R$^{10a}$ to R$^{10f}$ and R$^{11a}$ to R$^{11f}$ independently represent H,
  alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), halo, OH, alkoxy, NH$_2$, N(H)alkyl and N(alkyl)$_2$),
  phenyl (which latter group is optionally substituted by one or more substituents selected from OH, halo, alkyl and alkoxy) or
  Het$^7$;
Het$^1$ to Het$^7$ independently represent 4- to 14-membered heterocyclic groups containing one or more heteroatoms selected from O, N and/or S, which heterocyclic groups may comprise one, two or three rings and may be substituted by one or more substituents selected from
  alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), Het$^a$, halo, OR$^{12a}$, S(O)$_t$R$^{12b}$, CN, N$_3$, NO$_2$, =O, B$^9$—C(O)—B$^{10}$—R$^{12c}$, N(R$^{12d}$)R$^{12e}$ and N(OH)R$^{12f}$)
  phenyl (which latter group is optionally substituted by one or more substituents selected from OH, halo, alkyl and alkoxy),
  Het$^b$, halo, OR$^{13a}$, =O, S(O)$_u$R$^{13b}$, CN, N$_3$, NO$_2$, B$^{11}$—C(O)—B$^{12}$—R$^{13c}$, N(R$^{13d}$)R$^{13e}$ and N(OH)R$^{13f}$;
R$^{12a}$ to R$^{12f}$ and R$^{13a}$ to R$^{13f}$ independently represent H,
  alkyl, alkenyl, alkynyl, cycloalkyl (which latter four groups are optionally substituted by one or more substituents selected from alkyl, alkenyl, alkynyl, cycloalkyl, phenyl (which latter group is optionally substituted by one or more substituents selected from OH, halo, alkyl and alkoxy), Het$^c$, halo, OH, alkoxy, NH$_2$, N(H)alkyl and N(alkyl)$_2$),
  phenyl (which latter group is optionally substituted by one or more substituents selected from OH, halo, alkyl and alkoxy) or
  Het$^d$;
B$^1$ to B$^{12}$ independently represent a direct bond, O, S or N(R$^{14}$);
n, p, q, r, t and u independently represent 0, 1 or 2;
R$^{14}$ represents H, alkyl, phenyl (which latter group is optionally substituted by one or more substituents selected from OH, halo, alkyl and alkoxy), cycloalkyl (which latter group is optionally substituted by one or more substituents selected from OH, =O, halo, alkyl and alkoxy) or Het$^e$;
Het$^a$ to Het$^e$ independently represent 5- or 6-membered heterocyclic groups containing one to four heteroatoms selected from O, N and/or S, which heterocyclic groups may be substituted by one or more substituents selected from halo, =O and alkyl;
R$^8$ represents 1,2,3,4-tetrahydroisoquinolinyl;
G$^2$ represents CH$_2$ or C(O); and
unless otherwise specified alkyl, alkenyl, alkynyl and cycloalkyl groups, as well as the alkyl part of alkoxy groups, may be substituted by one or more halo atoms.

13. A compound as claimed in claim 12, wherein R$^2$ represents
  C$_{2-4}$ alkyl, C$_{5-6}$ cycloalkyl (which latter two groups are optionally substituted by one or more substituents selected from alkyl, cycloalkyl, aryl, Het$^1$, halo, OR$^{4a}$, S(O)$_n$R$^{4b}$, B$^1$—C(O)—B$^2$—R$^{4c}$ and N(R$^{4d}$)R$^{4e}$),
  aryl or
  Het$^2$.

14. A compound as claimed in claim 13, wherein G$^2$ is CH$_2$ and c is in each instance 1.

15. A compound as claimed in claim 12, wherein
R$^2$ is C$_{2-4}$ alkyl;
G$^2$ is CH$_2$; and
c is in each instance 1.

* * * * *